(12) United States Patent
Black et al.

(10) Patent No.: US 8,292,620 B2
(45) Date of Patent: Oct. 23, 2012

(54) INTRA-ORAL DEVICE AND METHOD

(75) Inventors: Brian P. Black, Mentone, CA (US);
John D. Van Ryn, Santa Barbara, CA (US)

(73) Assignee: Brian P. Black, Mentone, CA (US)

( * ) Notice: Subject to any disclaimer, the term of this patent is extended or adjusted under 35 U.S.C. 154(b) by 0 days.

(21) Appl. No.: 13/220,544

(22) Filed: Aug. 29, 2011

(65) Prior Publication Data
US 2011/0311942 A1    Dec. 22, 2011

Related U.S. Application Data

(62) Division of application No. 12/284,900, filed on Sep. 26, 2008, now Pat. No. 8,029,280.

(60) Provisional application No. 61/126,294, filed on May 2, 2008.

(51) Int. Cl.
*A61C 17/06* (2006.01)
*A61C 17/14* (2006.01)

(52) U.S. Cl. .............................. 433/93; 433/94; 433/140

(58) Field of Classification Search .............. 433/91–96, 433/140, 229; 285/361, 402; 128/859–860; 600/237–244
See application file for complete search history.

(56) References Cited

U.S. PATENT DOCUMENTS

| | | | |
|---|---|---|---|
| 2,111,859 A | 3/1938 | Kennedy | |
| 2,937,445 A | 5/1960 | Erickson | |
| 3,090,122 A | 5/1963 | Erickson | |
| 4,024,642 A | 5/1977 | Zorovich | |
| 4,167,814 A | 9/1979 | Schubert | |
| 4,259,067 A | 3/1981 | Nelson | |
| 4,425,911 A | 1/1984 | Luomanen et al. | |
| 4,583,527 A | 4/1986 | Musicant et al. | |
| 4,802,851 A | 2/1989 | Rhoades | |
| 4,906,188 A | 3/1990 | Moseley | |
| 4,975,057 A | 12/1990 | Dyfvermark | |

(Continued)

FOREIGN PATENT DOCUMENTS

GB    1017515    1/1966

(Continued)

OTHER PUBLICATIONS http://www.indentiv.com, Sep. 22, 2008, 3-pages.

(Continued)

*Primary Examiner* — Chris L Rodriguez
*Assistant Examiner* — Edward Moran
(74) *Attorney, Agent, or Firm* — Pillsbury Winthrop Shaw Pittman LLP

(57) ABSTRACT

An intra-oral device includes a tongue shield aspirator, a bite member, a bite grip, and an evacuation tube. The tongue shield aspirator may include a tongue retractor portion and a cheek retractor portion, and may be an open, unitary, and/or flexible component made of position-memory material. The bite member includes a conduit which receives the tongue shield aspirator through one end and the evacuation tube through the opposite end. The free end of the evacuation tube is connectable directly to a HVE valve to aspirate fluid/debris from the mouth. The device may be positioned in the mouth by bending the distal (free) end of the tongue shield aspirator, inserting the bite member into the mouth first, followed by the tongue shield aspirator as the device is moved towards the patient's cheek, releasing the free end of the tongue shield aspirator, and having the patient bite down on the bite member.

20 Claims, 46 Drawing Sheets

U.S. PATENT DOCUMENTS

| | | | |
|---|---|---|---|
| 5,152,686 A | 10/1992 | Duggan et al. |
| 5,232,362 A | 8/1993 | Kanas |
| 5,366,489 A | 11/1994 | Burgio et al. |
| 5,438,976 A | 8/1995 | Nash |
| 5,496,363 A | 3/1996 | Burgio et al. |
| 5,513,986 A | 5/1996 | Feltham et al. |
| 5,516,286 A | 5/1996 | Kushner |
| 5,588,836 A | 12/1996 | Landis et al. |
| 5,725,370 A | 3/1998 | Himeno et al. |
| 5,762,496 A | 6/1998 | Albertsson et al. |
| 5,873,718 A | 2/1999 | Sullivan |
| 5,924,866 A | 7/1999 | Eldreth |
| 6,022,214 A | 2/2000 | Hirsch et al. |
| 6,149,430 A | 11/2000 | Nemetz et al. |
| 6,213,772 B1 | 4/2001 | Costello |
| 6,244,866 B1 | 6/2001 | Campbell |
| 6,338,627 B2 | 1/2002 | Hirsch et al. |
| 6,379,147 B1 | 4/2002 | Georgakis et al. |
| 6,575,746 B2 | 6/2003 | Hirsch et al. |
| 6,634,884 B2 | 10/2003 | Phillips |
| 6,652,276 B2 | 11/2003 | Fischer et al. |
| 6,655,960 B2 | 12/2003 | Fischer |
| 6,939,134 B2 | 9/2005 | Sherry et al. |
| 6,974,321 B2 | 12/2005 | Hirsch et al. |
| 6,981,870 B2 | 1/2006 | Heasley |
| 7,293,990 B2 | 11/2007 | Hirsch et al. |
| 2004/0033468 A1 | 2/2004 | Fischer et al. |
| 2006/0063129 A1 | 3/2006 | Hirsch |
| 2007/0231773 A1 | 10/2007 | Pontynen et al. |
| 2007/0259307 A1 | 11/2007 | Quan et al. |
| 2008/0318183 A1 | 12/2008 | Suzman |

FOREIGN PATENT DOCUMENTS

WO   WO 2008/064904 A1   6/2008

OTHER PUBLICATIONS

Practicon Dental, 2-pages.
International Search Report and Written Opinion of the International Searching Authority, (PCT/US2009/000903), (8-pages) (Jul. 22, 2009).

INTRA-ORAL DEVICE AND METHOD

RELATED APPLICATION DATA

This application is a divisional of patent application Ser. No. 12/284,900, filed Sep. 26, 2008, now U.S. Pat. No. 8,029,280, which claims priority from Provisional Application Ser. No. 61/126,294, filed May 2, 2008, all of which are incorporated herein by reference in their entirety.

FIELD OF THE INVENTION

Aspects of embodiments of the present invention relate generally to dental devices and methods and, more specifically, to devices and methods for providing intra-oral operative isolation, fluid and debris aspiration, and tongue and cheek retraction.

BACKGROUND OF INVENTION

During dental and similar or related procedures, the patient's oral cavity is continually being filled with debris and fluids, including saliva and water sprayed into the mouth. Moreover, depending on the specific location of treatment, the patient's tongue and/or cheek are typically in the operator's way. To address these issues, separate tongue retractors, cheek retractors, and fluid-aspiration devices have been introduced that generally function as separate and discrete devices. As such, the dentist will usually need the help of an assistant in order to benefit from the advantages offered by such multiplicity of independent devices.

In order to address this issue, multi-unit devices have been introduced that combine two or more of the above-mentioned functionalities. Nevertheless, some of these devices have proven to be too cumbersome, as they require, e.g., special attachment units and tools for connecting the device to a vacuum unit. As a result, they are also quite expensive to manufacture and purchase. In addition, some devices are very complex, as they require, for example, both high-volume and low-volume suctioning capabilities, or an additional electrical connection. The latter creates not only a bulkier device, but also safety-related issues that must be dealt with.

SUMMARY OF THE INVENTION

Embodiments of the invention are directed to an intra-oral device comprising an open tongue shield aspirator including a first layer having a posterior side, an anterior side, a proximal edge, a distal edge, a bottom edge, and a top edge, a second layer having a posterior side, an anterior side, a proximal edge, a distal edge, a bottom edge, and a top edge, wherein the proximal edges of the first and second layers are substantially flush with each other, and the posterior side of the second layer is connected to the anterior side of the first layer by a plurality of walls such that the first and second layers are spaced apart from one another and define therebetween an axial passageway, with the passageway having a distal end that coincides with the second layer's distal edge and is configured to be directly exposed to a patient's oral cavity, and a hollow neck extending proximally from the proximal edges of the first and second layers and in fluid communication with the passageway, wherein the neck's proximal end constitutes the passageway's proximal end.

The intra-oral device may include an evacuation tube having a first end, and a second end that is configured to be coupled directly to a high-volume evacuation (HVE) valve, and a bite member that is configured to be disposed between the patient's upper and lower teeth. The bite member may include a conduit such that, at a distal end of the conduit, the bite member is configured to detachably mate with the neck of the tongue shield aspirator and, at a proximal end of the conduit, the bite member is configured to detachably mate with the first end of the evacuation tube, thereby providing fluid communication between the HVE valve and the patient's oral cavity via the evacuation tube, conduit, and passageway.

Embodiments of the invention are also directed to an intra-oral device comprising a unitary tongue shield aspirator including a first layer comprising a proximal flap that is configured to retract a patient's tongue, a second layer spaced apart from the first layer by a plurality of walls so as to define an axial passageway between the layers, with the passageway being in direct communication with the patient's oral cavity, and the plurality of walls forming at least one upper channel extending at an angle from the passageway to a top edge of the second layer and at least one lower channel extending at an angle from the passageway to the bottom edge of the second layer so as to provide fluid communication between the passageway and the patient's oral cavity, and a hollow neck extending proximally from the first and second layers and in fluid communication with the passageway.

The intra-oral device may include an evacuation tube that is configured to be coupled directly to a high-volume evacuation valve, a bite member having an oblique conduit such that, at its distal end, the conduit is configured to detachably receive the neck of the tongue shield aspirator and, at its proximal end, the conduit is configured to detachably receive an end of the evacuation tube. In embodiments of the invention, a bite grip may be included, wherein the bite grip has an upper member configured to fit over a top side of the bite member and engageable by the patient's upper teeth and a lower member configured to fit over a bottom side of the bite member and engageable by the patient's lower teeth.

Additional aspects and features of embodiments of the invention are described below and/or shown in the accompanying diagrams.

DETAILED DESCRIPTION

As described in more detail hereinbelow, embodiments of the present invention are directed to intra-oral devices used to aid dentists, hygienists, oral surgeons, other dental professionals, etc. (hereinafter referred to as "operator") in isolating the operative field, aspirating fluids and debris while working in the mouth, and maintaining patient comfort by holding the mouth open and protecting the tongue and cheek, thereby providing simultaneous intra-oral operative isolation, fluid and debris aspiration, and tongue and cheek retraction.

Figure 1:
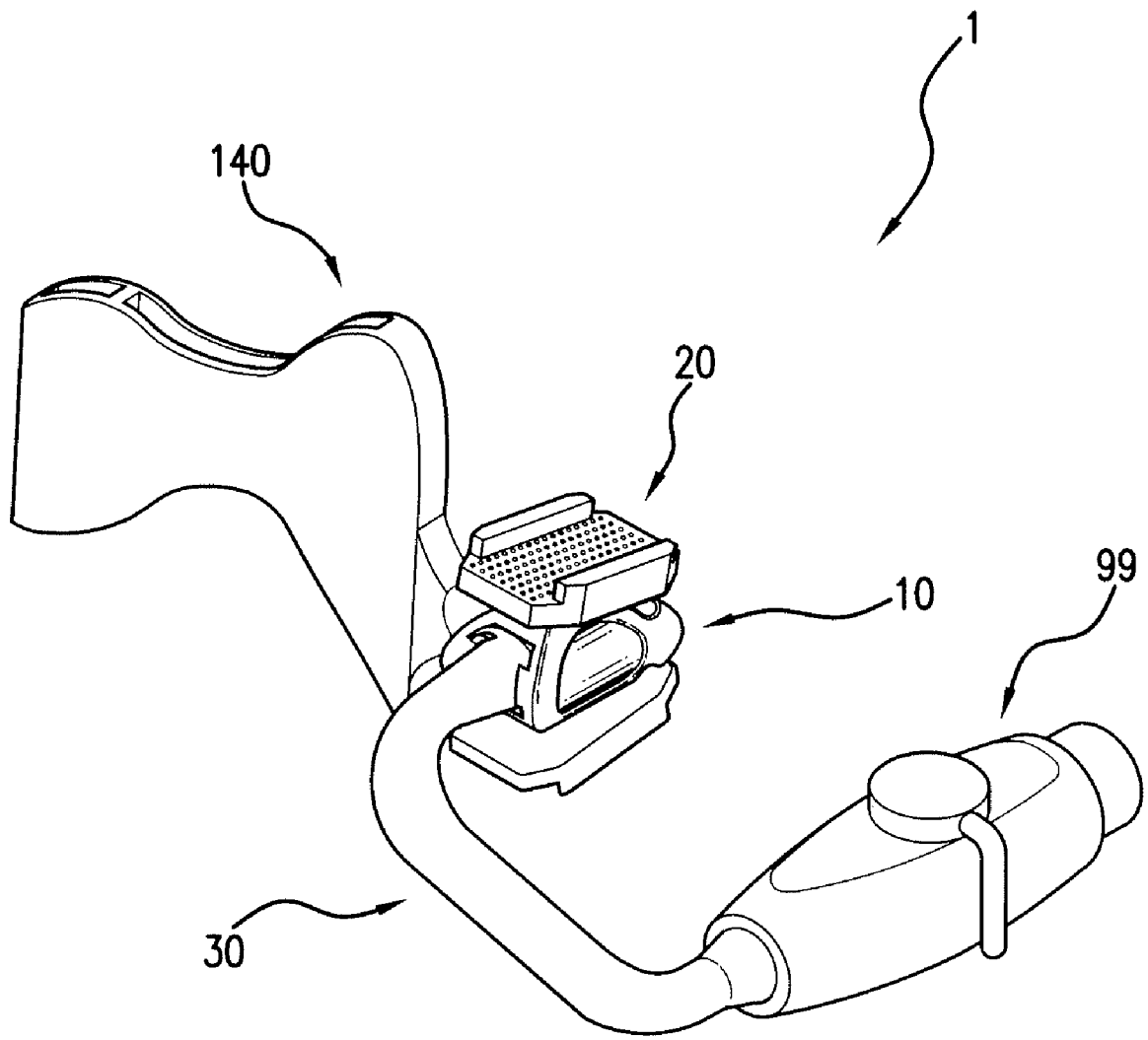
FIG. 1 is an assembled intra-oral device in accordance with an embodiment of the invention.
Figure 2:
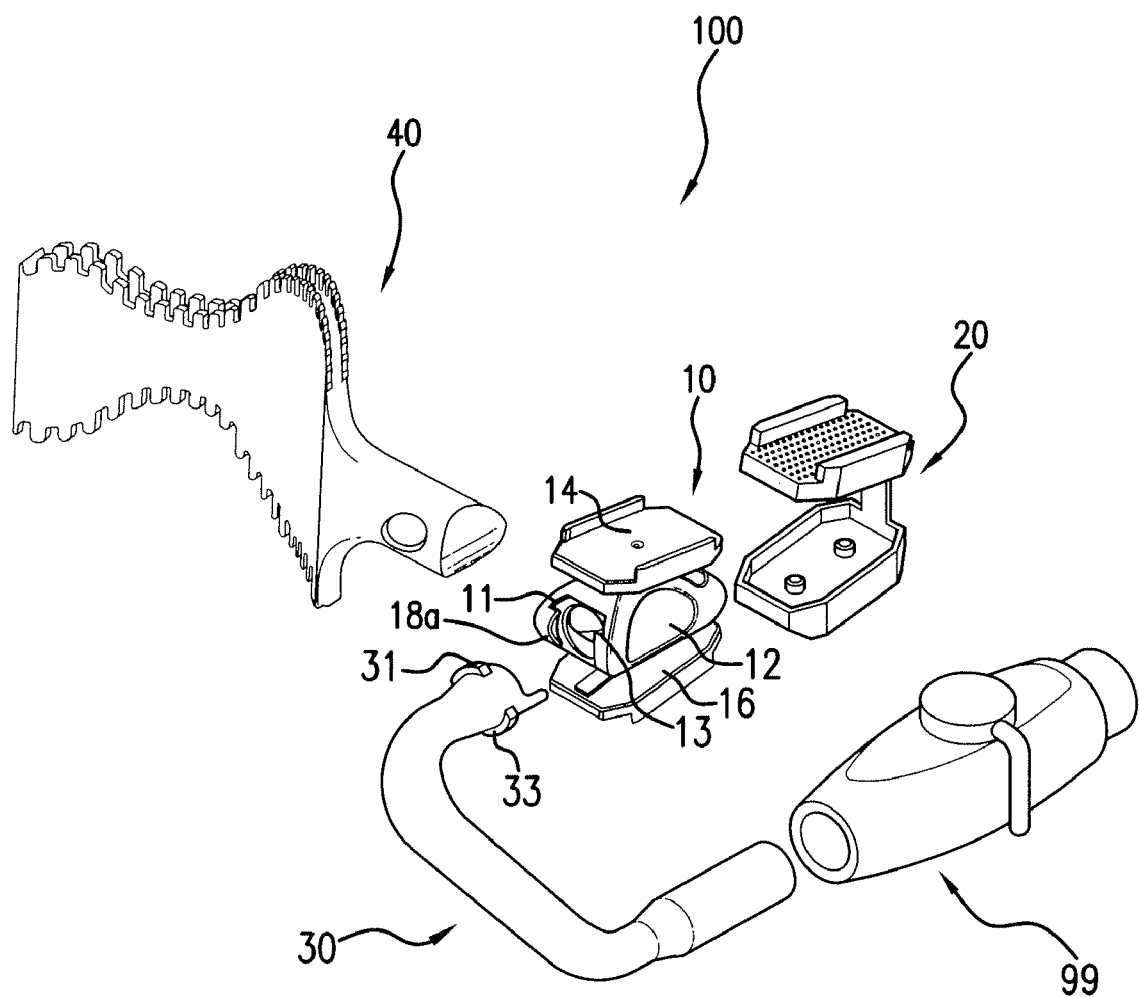
FIG. 2 is an exploded view of components of an intra-oral device in accordance with an embodiment of the invention.

FIG. 1 shows an assembled intra-oral device 1, and FIG. 2 shows an exploded view of components of a device 100, in accordance with embodiments of the present invention. As shown in FIGS. 1 and 2, embodiments of an intra-oral device may include four main components: a bite member 10, a bite grip 20, an evacuation tube 30, and a tongue shield aspirator 40, 140.

FIGS. 1-7, e.g., show various tongue shield aspirators in accordance with embodiments of the present invention. It is noted that any one or more of the tongue shield aspirators described in the ensuing discussion may be disposable. Moreover, any one or more of the tongue shield aspirators may be made of non-latex and/or non-silicone material, and may be adapted for manufacture in a range of sizes, including adult and pediatric sizes.

Figure 3A:
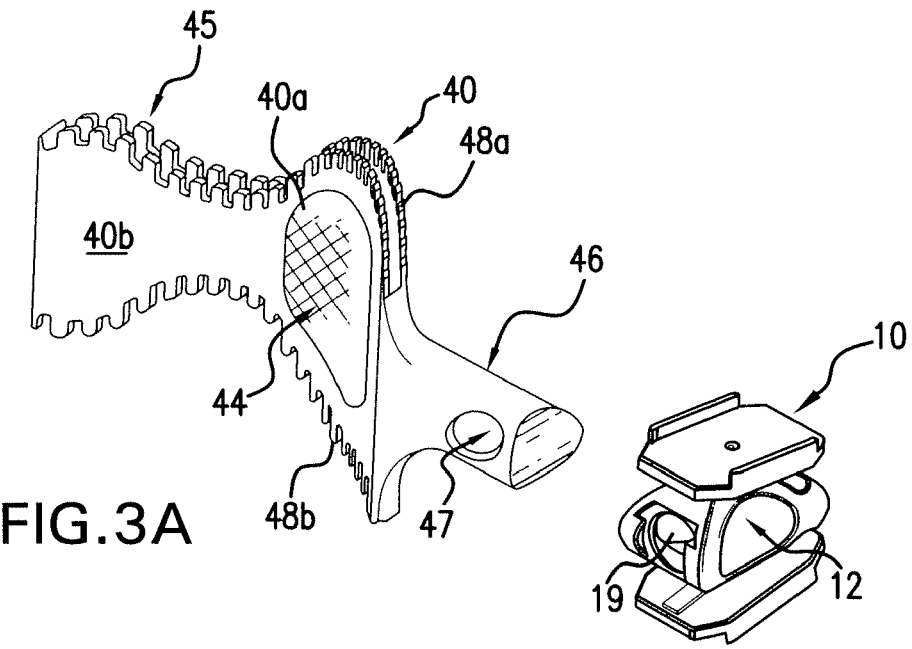
FIG. 3A is an exploded, perspective view of a bite member and a tongue shield aspirator in accordance with an embodiment of the invention.
Figure 3B:
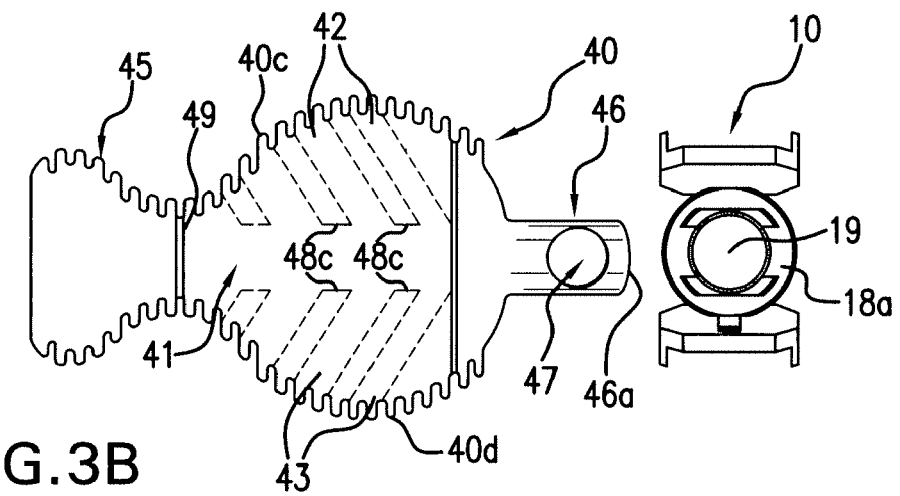
FIG. 3B is an exploded, anterior view of the bite member and a tongue shield aspirator shown in FIG. 3A.
Figure 3C:
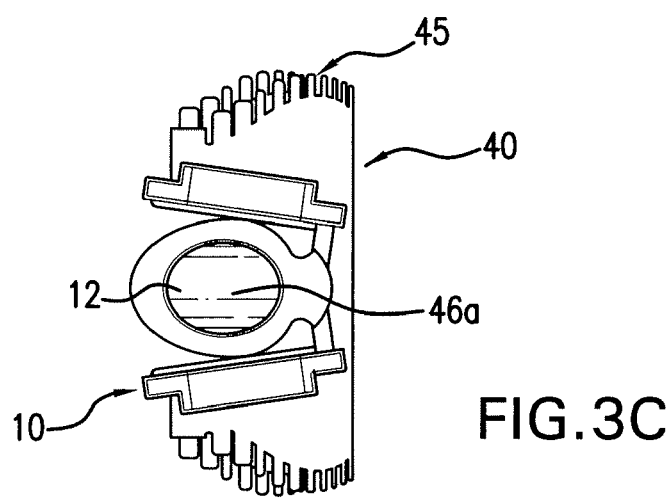
FIG. 3C is a lateral view of the bite member and tongue shield aspirator shown in FIG. 3A.

As shown in FIGS. 3A-3C, a posterior tongue shield aspirator 40 has a first (proximal) flap 40a, which is configured to retract a patient's tongue, and a second (distal) flap 40b, which is configured to retract a patient's cheek. The first and second flaps are joined to one another at a transition section 49 such that, when viewed from the perspectives shown in FIGS. 3A and 3B, the transition section 49 forms the narrowest section of the tongue shield aspirator 40, thereby forming an isthmus between the flaps 40a, 40b. It is noted that, although the flaps 40a, 40b are described herein as being "joined" at the transition section 49, this is simply for ease of reference. In practice, any of the tongue shield aspirators described herein in accordance with the various embodiments of the invention (e.g., the tongue shield aspirator 40) may be manufactured as a one-piece, or unitary, component, or the two flaps 40a, 40b may be manufactured separately, and then coupled to one another at the transition section 49.

The tongue shield aspirator 40 includes a longitudinal hollow lumen 41 that is in fluid communication with a multiplicity of branches, or channels, that may extend at an angle therefrom. More specifically, the proximal flap 40a and/or the distal flap 40b of the tongue shield aspirator 40 may be formed from a first (posterior) layer 48a and a second (anterior) layer 48b which are connected to, but spaced apart from, one another by transverse walls 48c. As shown, e.g., in FIG. 3B, each set of two consecutive walls 48c that are disposed above the longitudinal lumen 41 forms an upper channel 42 which extends from the longitudinal lumen 41 towards the top edge 40c of the proximal flap 40a. Similarly, each set of two consecutive walls 48c that are disposed below the longitudinal hollow lumen 41 forms a lower channel 43 which extends from the longitudinal lumen 41 towards the bottom edge 40d of the proximal flap 40a. With this construction, the longitudinal hollow lumen 41 itself is formed as a passageway having intermittent boundary sections that are defined by the ends of the transverse walls 48c that are closest to the longitudinal lumen 41. In this way, the channels 42, 43 provide a plurality of conduits for debris and fluid evacuation, thereby allowing for simultaneous aspiration of debris and fluid from top (palate of mouth) to bottom (floor of mouth), and through the longitudinal lumen 41, during dental procedures.

It is noted that, while, in the embodiment of FIGS. 3A-3C, the tongue shield aspirator 40 includes a plurality of upper channels and a plurality of lower channels, this is by way of illustration only. Thus, a tongue shield aspirator in accordance with embodiments of the invention may include one or more of each of the upper channel(s) 42 and lower channel(s) 43. In addition, the layers 48a, 48b and the transverse walls 48c may be made of flexible material so as to enable proper placement of the tongue shield aspirator in the patient's mouth. Thus, each of the walls 48c is "transverse" in that it is generally perpendicular to the inner surfaces of the first and second layers 48a, 48b when the tongue shield aspirator is laid flat, but flexes along with the first and second layers 48a, 48b when the tongue shield aspirator itself is flexed, e.g., for placement in the patient's mouth.

A tongue shield aspirator having the above-described construction may be considered an "open" tongue shield in the sense that the upper and lower edges of the tongue shield are open to, or in communication with, the patient's oral cavity. Thus, with reference to FIGS. 3A-3C, for example, each upper channel 42 extends to and through the top edge 40c of the proximal flap 40a, wherein the proximal flap may be formed by the proximal portions of the posterior layer 48a and the anterior layer 48b, and the top edge 40c of the proximal flap may be formed by the respective top edges of the posterior layer 48a and the anterior layer 48b. Similarly, each lower channel 43 extends to and through the bottom edge 40d of the proximal flap 40a, wherein the bottom edge 40d is formed by the respective bottom edges of the posterior layer 48a and the anterior layer 48b. In this way, each of the top edge 40c and the bottom edge 40d of the proximal flap 40a is open along the entirety of the length thereof.

In embodiments of the invention, the upper opening defined by the space between the top edges of the anterior and posterior layers, and the lower opening defined by the space between the bottom edges of the anterior and posterior layers may extend through an additional portion of the tongue shield aspirator. Thus, a tongue shield aspirator in accordance with embodiments of the invention may be open through a portion or all of (the top and bottom edges of) the transition section between the proximal and distal flaps. Alternatively, the tongue shield aspirator may be open through a portion or all of (the top and bottom edges of) the distal flap.

As described above in connection with the proximal flap 40a, in embodiments of the invention, the distal flap 40b may be formed by the distal portions of the posterior layer 48a and the anterior layer 48b. In alternative embodiments, however, one or both of the proximal and distal flaps may be formed by the respective portion of the posterior layer only. In some such embodiments, the anterior layer may exclude some or all of the proximal and/or distal portions thereof.

Returning to FIG. 3, the tongue shield aspirator 40 includes a neck 46 having a transverse anterior opening 47. In the embodiments shown in FIGS. 2 and 3, the longitudinal hollow lumen (or passageway) 41 extends from the transition section 49 through the neck 46 and to the anterior opening 47. As will be discussed hereinbelow, when assembled, the neck 46 is received within a lateral orifice of a bite member (such as, e.g., orifice 12 of bite member 10), such that the anterior opening 47 is aligned with an opening in an anterior face of the bite member. It is noted that, in the embodiment shown in FIGS. 3A-3C, the transition section may represent a closed end of the passageway. However, in embodiments of the invention, the longitudinal lumen 41 and the channels 42, 43 may extend through not only the first flap 40a, but also at least a portion of the second flap 40b.

In embodiments of the invention, one or both of the flaps 40a, 40b may include an internal wire mesh 44, thereby allowing the operator to mold the tongue shield aspirator 40 as needed for appropriate fit in the patient's mouth. In addition, as shown in FIGS. 2 and 3, one or more of the flaps 40a, 40b may include finger-like projections 45 on the bottom and/or top edge thereof, thereby creating a "one-size-fits-all" feature and providing a comfortable form-fitting seal within the patient's mouth.

Figure 4A:
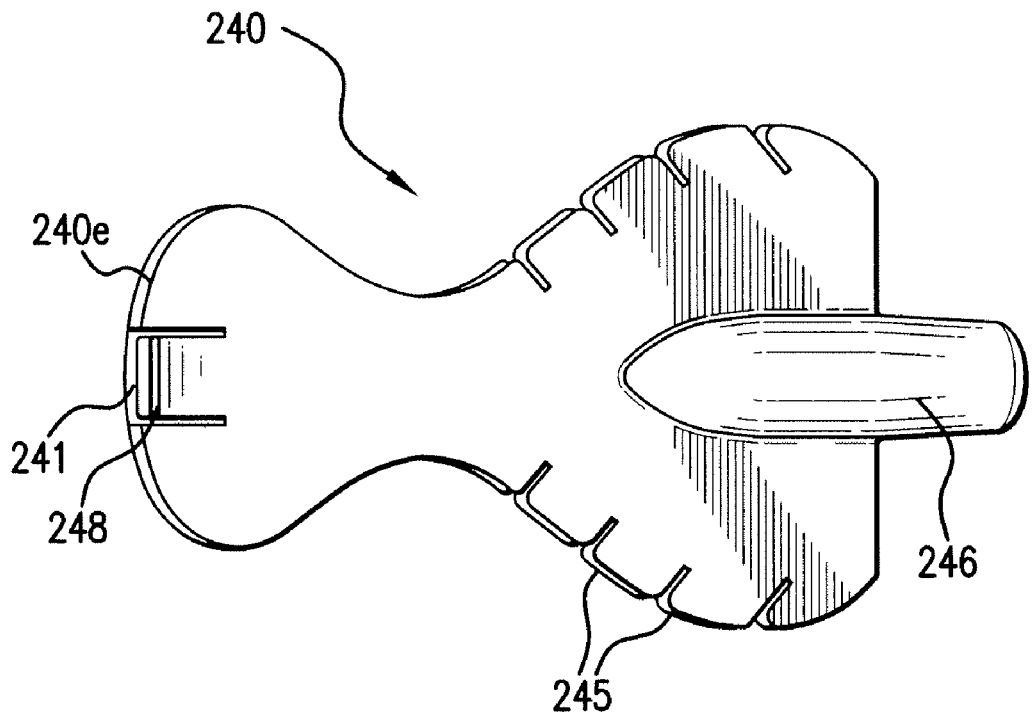
FIG. 4A is a posterior view of a tongue shield aspirator in accordance with an embodiment of the invention.
Figure 4B:
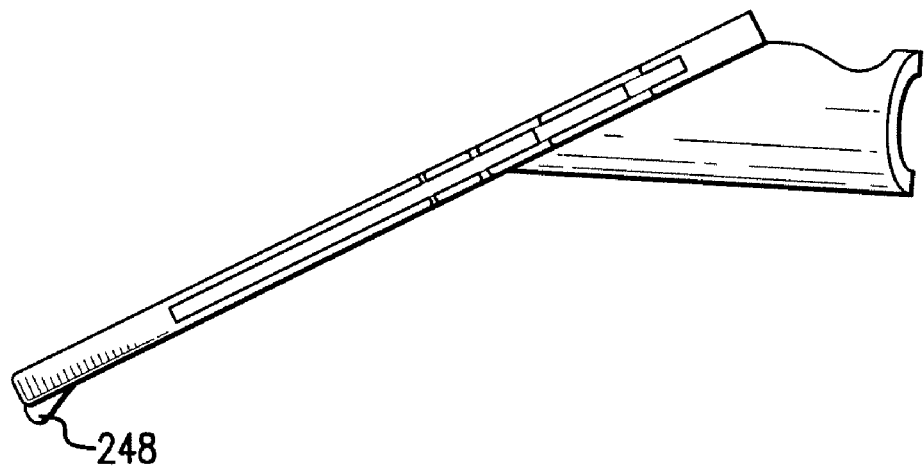
FIG. 4B is a top view of the tongue shield aspirator shown in FIG. 4A.
Figure 4C:
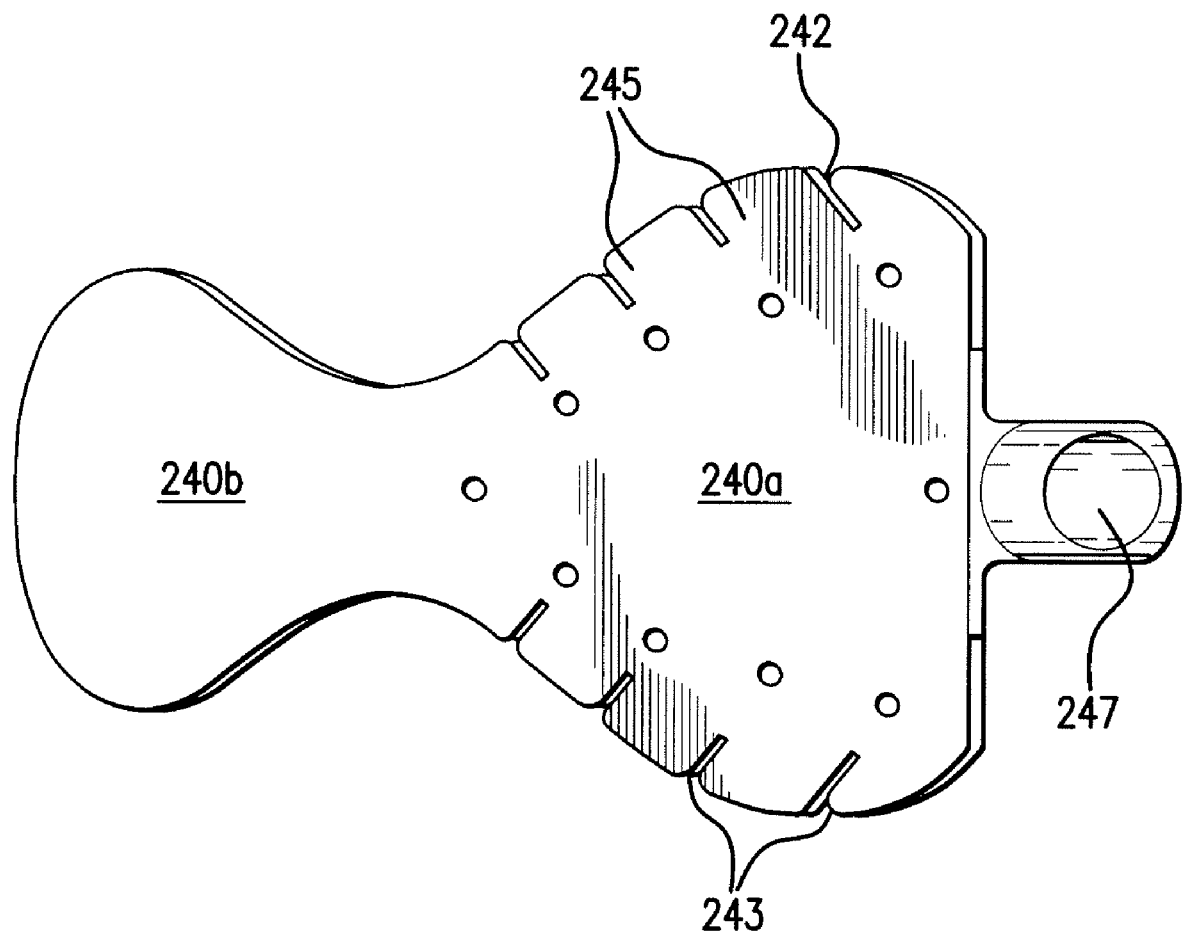
FIG. 4C is an anterior view of the tongue shield aspirator shown in FIG. 4A.

FIGS. 4A-4C show an alternative embodiment of the posterior tongue shield aspirator 240 having a first flap 240a, a second flap 240b, channels 242, 243 extending from a longitudinal lumen 241, and a neck 246 defining a transverse anterior opening 247 therethrough. These, as well as many other features of the tongue shield aspirator 240 resemble those of the tongue shield aspirator 40 discussed immediately above. However, in contrast with the latter, the tongue shield aspirator 240 may include finger-like projections 245 on only the first flap 240a. In addition, the longitudinal hollow lumen 241 of the tongue shield aspirator 240 extends from the anterior opening 247 to an outer edge 240e of the second flap 240b. Depending on the specific application, such a configuration may offer various advantages over the construction of the tongue shield aspirator 40 shown, e.g., in FIG. 3. In addition, the inclusion of a longitudinal lumen that extends through both flaps 240a, 240b allows for a simpler, more optimized manufacturing process.

In certain applications, aspiration from the distal side of the second flap 240b (i.e., the side that includes the edge 240e) may be either unnecessary and/or undesirable, as it may lead to loss of pressure (i.e., lower suctioning capability) through the channels 242, 243. For these applications, a compressible valve 248 may be included on the posterior side of the second flap 240b. Thus, when the tongue shield aspirator 240 is placed in a patient's mouth, with the second flap 240b retracting the patient's cheek, the force that is applied between the patient's cheek and the posterior side of the second flap 240b is sufficient to close the valve 248, thereby closing off an end of the longitudinal lumen 241.

It is important to note that, for ease of manufacturing, the tongue shield aspirator 240 may be manufactured as a "flat" piece, i.e., as shown in FIG. 4. However, such depiction in connection with this, or any other embodiments of the tongue shield aspirator discussed herein is by way of illustration, and not limitation. Moreover, regardless of whether any given tongue shield aspirator is manufactured as a flat or arcuate component, the tongue shield aspirator may be made of material that has position memory. In this way, in order to place the component into the patient's mouth, the two flaps (e.g., 40a and 40b, or 240a and 240b) are first brought towards one another. This results in a generally C-shaped tongue shield aspirator that is then inserted into the patient's mouth as discussed in more detail hereinbelow. Once inserted, the operator releases the force that was previously applied to the two flaps, at which point the first flap expands outwards (i.e., towards a 180° angle) to retract the patient's tongue, and the second flap expands outwards to retract the patient's cheek. It is noted that, in some embodiments, e.g., those in which the tongue shield aspirator is not, and/or is not manufactured as, a unitary component, only certain portions of the component, such as, e.g., the transition section between the first and second flaps may be made of material having position memory to provide the above-described functionality.

As noted, the primary function of the tongue shield aspirator is to aspirate from top (palate of mouth) to bottom (floor of mouth) simultaneously during dental procedures while, at the same time, retracting or shielding the tongue and cheek from the operator's instruments, aspirating fluids/debris from the operating site, and preventing fluid/debris aspiration by the patient during dental procedures. To this end, embodiments of the tongue shield aspirator may take on various shapes and configurations in order to accommodate different dental procedural needs.

Figure 5A:
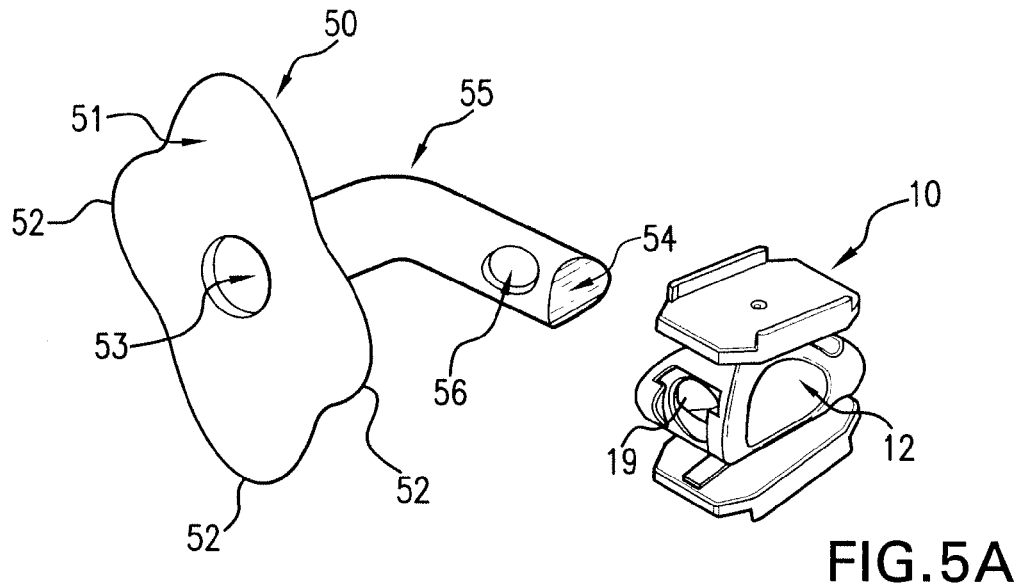
FIG. 5A is an exploded, perspective view of a bite member and a tongue shield aspirator in accordance with an alternative embodiment of the invention.
Figure 5B:
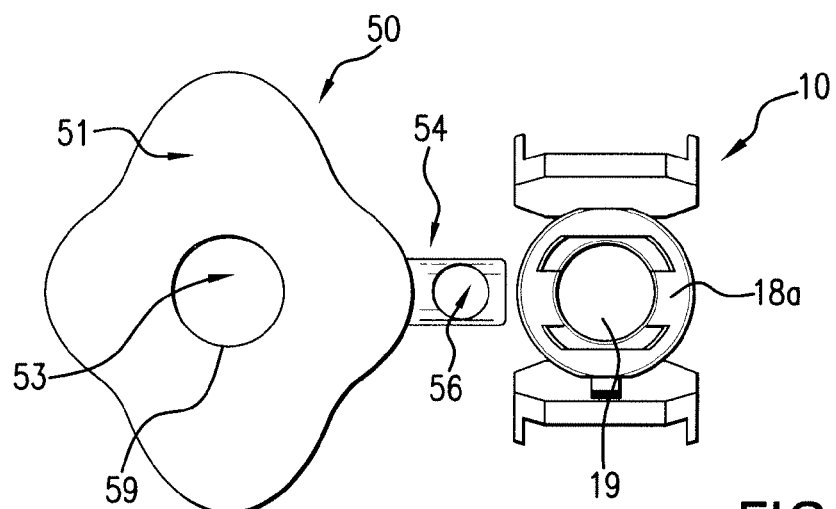
FIG. 5B is an exploded, anterior view of the bite member and tongue shield aspirator shown in FIG. 5A.
Figure 5C:
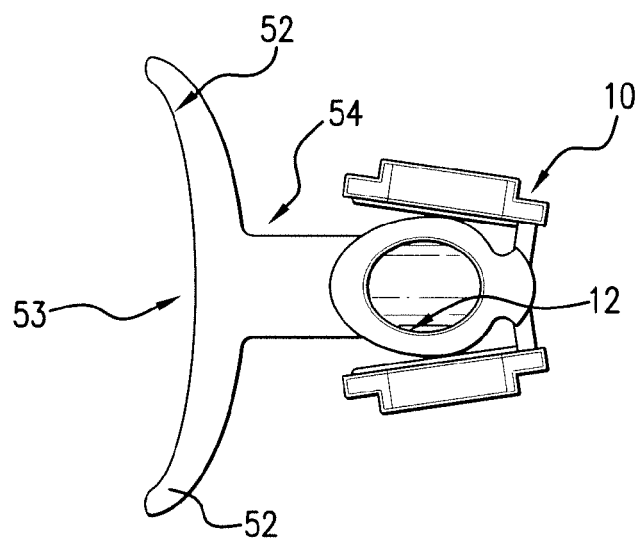
FIG. 5C is a lateral view of the bite member and tongue shield aspirator shown in FIG. 5A.

FIGS. 5A-5C show one alternative embodiment, in which an anterior tongue shield aspirator 50 has a single longitudinal hollow channel 53. In practice, this component may be used to aspirate from the posterior surfaces of upper (maxillary) and lower (mandibular) anterior teeth simultaneously while retracting or shielding the tongue from the operator's instruments, aspirating fluids/debris from the operating site, and preventing fluid/debris aspiration by the patient during dental procedures.

As shown in FIG. 5C, the tongue shield aspirator 50 has a generally cup-shaped, or trumpet-shaped, configuration when viewed laterally. In addition, when viewed anteriorly, the tongue shield 50 has a regularly-undulating periphery that may be described by a plurality of lobes 52 defining the anterior face 51 thereof. As before, this component has a neck 54 which, in this embodiment, extends posteriorly from a posterior face of the tongue shield, and then bends 55 at about a 90° angle, extending toward one side of the mouth.

The neck 54 defines a transverse anterior opening 56 therethrough. Thus, the longitudinal hollow channel 51 extends from an opening 59 in the anterior face 51, through the neck 54, and to the opening 56. When assembled, the neck 54 is received within a lateral orifice of a bite member (such as, e.g., orifice 12 of bite member 10), such that the anterior opening 56 is aligned with an opening in an anterior face of the bite member. This allows the tongue shield aspirator 50 to aspirate lingual or posterior surfaces of anterior teeth during tooth preparation. More specifically, the cup-shaped surface is configured to capture aerosol and debris as the operator prepares the teeth anterior to the tongue shield. Although this component may be adapted for manufacture in a variety of sizes, it also includes a "one-size-fits-all" feature in that its periphery can be trimmed for a more precise fit in the patient's mouth.

Figure 6A:
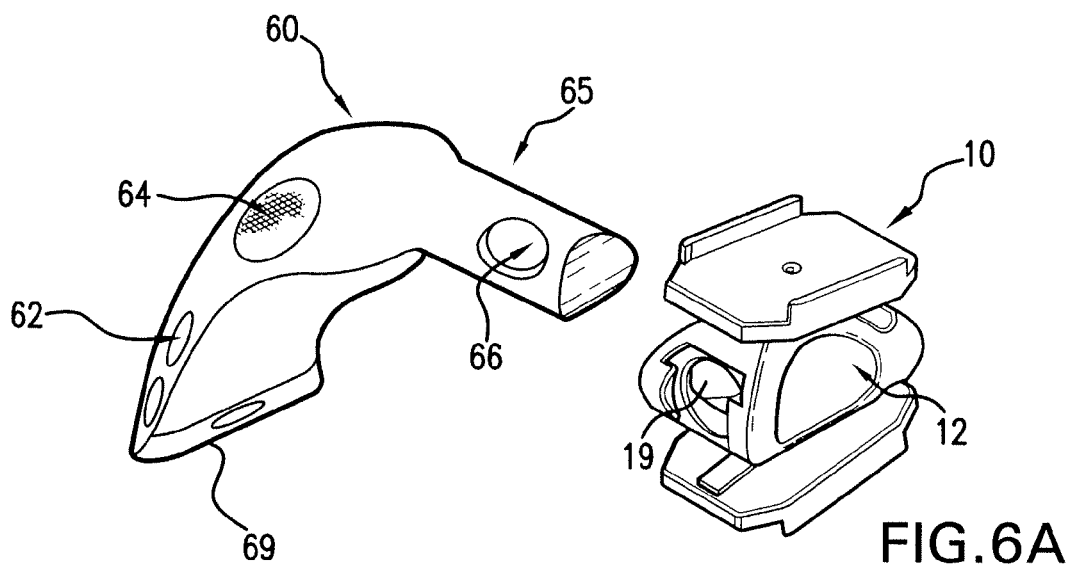
FIG. 6A is an exploded, perspective view of a bite member and tongue shield aspirator in accordance with an alternative embodiment of the invention.
Figure 6B:
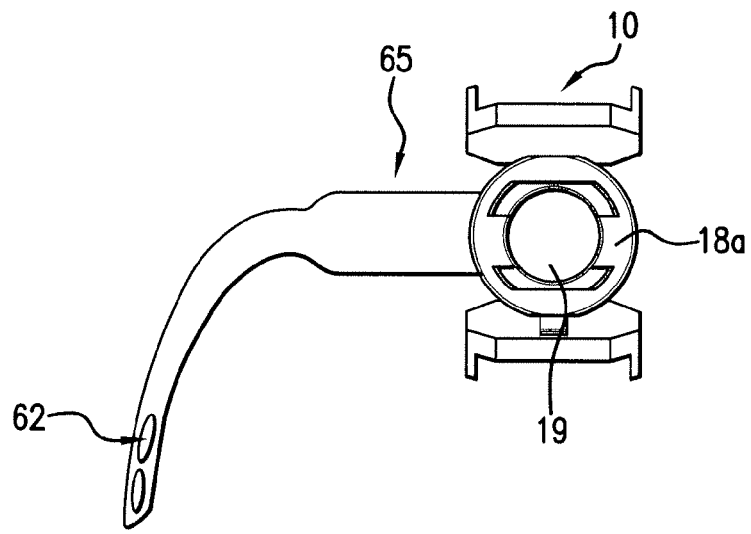
FIG. 6B is an anterior view of the bite member and tongue shield aspirator shown in FIG. 6A.
Figure 6C:
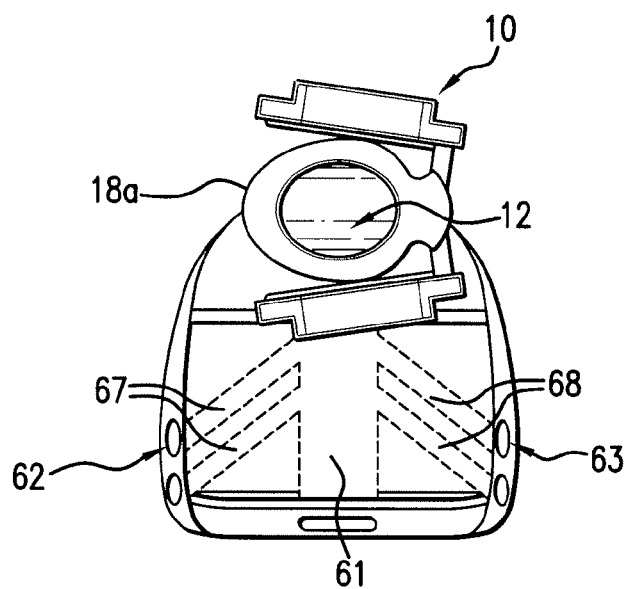
FIG. 6C is a lateral view of the bite member and tongue shield aspirator shown in FIG. 6A.

FIGS. 6A-6C show a generally paddle-shaped surgeon's tongue shield aspirator 60, which is configured such that, in use, an anterior edge 62 thereof is oriented anteriorly, and a bottom edge 69 thereof is positioned proximate the floor of the mouth. The tongue shield aspirator 60 has a longitudinal hollow lumen 61 that is in fluid communication with a multiplicity of branches, or channels, that extend at an angle therefrom. As shown in FIG. 6C, one set of branches 67 extends from the longitudinal lumen 61 to the anterior edge 62 of the tongue shield, and another set of branches 68 extends from the longitudinal lumen 61 to the posterior edge 63 of the tongue shield. In addition, the longitudinal lumen 61 itself extends to and through the bottom edge 69.

In this way, the longitudinal lumen 61 and the channels 67, 68 provide a plurality of conduits for debris and fluid evacuation, thereby allowing for simultaneous aspiration of fluids/debris from the operating site from side to side and the floor of the mouth during dental procedures and oral surgery (e.g., tooth extractions). At the same time, the tongue shield aspirator 60 retracts and/or shields the lateral surface of the tongue from the operator's instruments while, at the same time, preventing fluid/debris aspiration by the patient during dental procedures.

The tongue shield aspirator 60 includes a neck 65 having a transverse anterior opening 66. As noted, in this embodiment, the longitudinal hollow lumen 61 extends from the bottom edge 69 through the neck 65 and to the anterior opening 66. When assembled, the neck 65 is received within a lateral orifice of a bite member (such as, e.g., orifice 12 of bite member 10), such that the anterior opening 66 is aligned with an opening in an anterior face of the bite member.

In embodiments of the invention, the tongue shield aspirator 60 may include an internal wire mesh 64, thereby allowing the operator to mold the tongue shield aspirator as needed for appropriate fit in the patient's mouth. Although this component may be adapted for manufacture in a variety of sizes, it does nevertheless include a "one-size-fits-all" feature, whereby the tongue shield may be trimmed to shorten its length or depth of placement into the floor of the mouth. This component may be disposable and may be made of material other than latex or silicone.

Figure 7A:
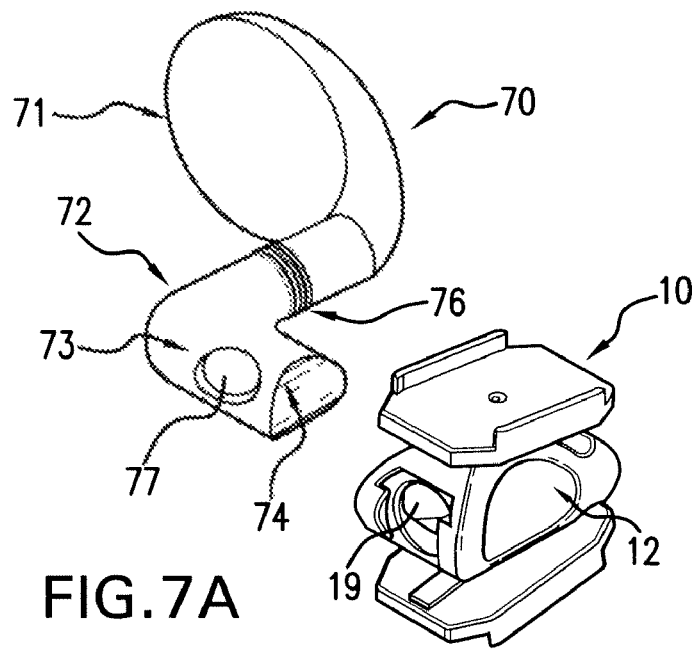
FIG. 7A is an exploded, perspective view of a bite member and tongue shield aspirator in accordance with an alternative embodiment of the invention.
Figure 7B:
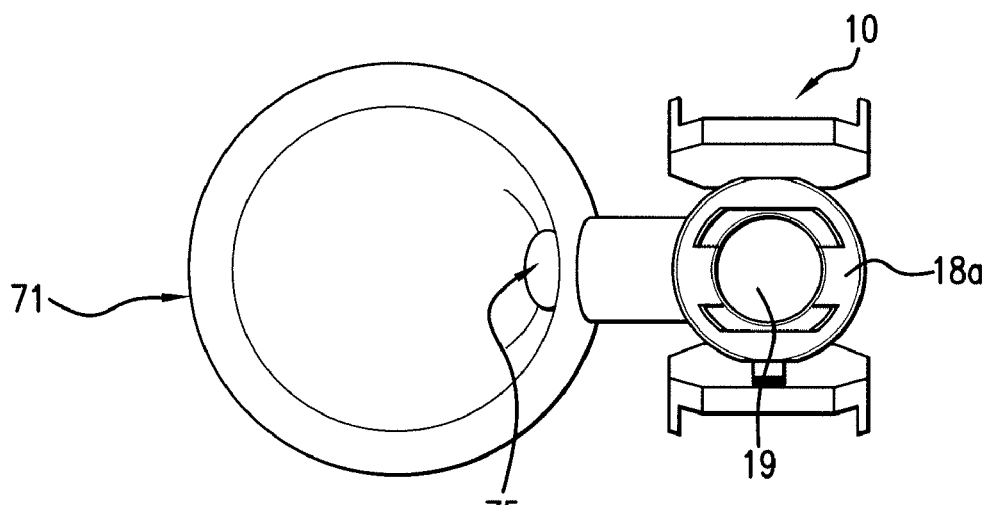
FIG. 7B is an anterior view of the bite member and tongue shield aspirator shown in FIG. 7A.
Figure 7C:
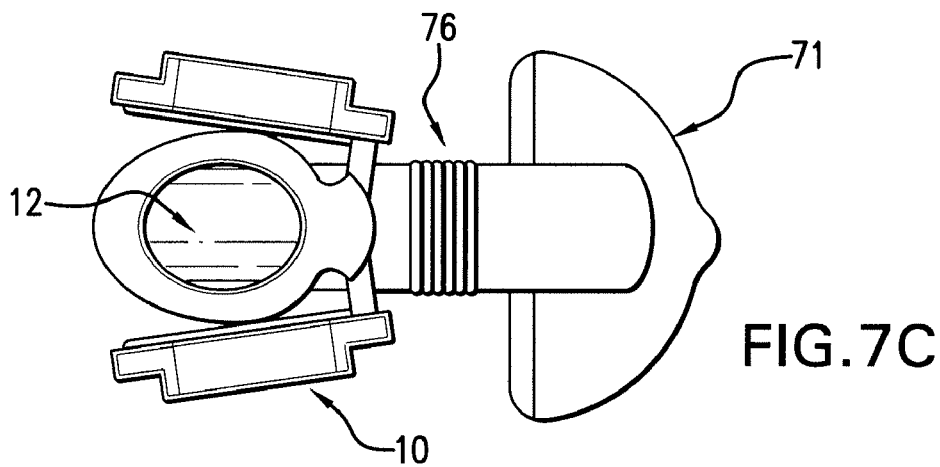
FIG. 7C is a lateral view of the bite member and tongue shield aspirator shown in FIG. 7A.

In yet another alternative embodiment, FIGS. 7A-7C show a general anesthesia (GA) tongue shield aspirator 70. The GA tongue shield aspirator 70 includes a cup 71 that may be a disposable component and may be made of material other than latex or silicone. The cup 71 is joined to a conduit 72 which extends substantially anteriorly from the cup 71, and then bends 73, at about a 90° angle, into a neck 74. In one embodiment, the conduit 72 may be made of bendable and/or moldable material, such as, e.g., plastic, and may include ribs 76 that allow the length of the conduit to be expanded or contracted as needed, thereby providing a "one-size-fits-all" feature. Again, the GA tongue shield aspirator 70 may be adapted for manufacture in a variety of sizes. It is also important to note that, while the conduit 72 may be manufactured as a separate component and then joined, or coupled, to the cup 71, this is by no means a requirement of the invention. Thus, for example, the cup 71 and conduit 72 may be manufactured as a unitary or integrated component.

The conduit 72 defines therethrough a longitudinal lumen that extends from an opening 75 in the cup 71 to a transverse anterior opening 77. Thus, when assembled, the neck 74 is received within a lateral orifice of a bite member (such as, e.g., orifice 12 of bite member 10), such that the anterior opening 77 is aligned with an opening in an anterior face of the bite member. In this way, in use, the GA tongue shield aspirator 70 may be configured to hold surgical gauze arranged as a "throat pack" and trap debris while aspirating fluid/debris. In addition, given that, during dental procedures in which the patient is placed under general anesthesia, the patient's normal responses to fluid/debris in the throat area are suppressed, the GA tongue shield aspirator is also configured to prevent fluid/debris aspiration by the patient.

As noted previously, the tongue shield aspirator (e.g., any one of the tongue shield aspirators 40, 50, 60, 70, 140, 240, or those described hereinafter) may be used in an intra-oral device in conjunction with a bite member, a bite grip, and an evacuation tube, any one or more of which may be made of disposable material (e.g., plastic). As will be evident from the ensuing discussion, the bite member is generally configured to hold the upper and lower jaws separate during dental procedures and/or similar procedures that require intubation. As such, this component is fully symmetrical and capable of bilateral use in the mouth. In addition, the bite member may be used independently of a tongue shield aspirator or an evacuation tube.

In general, the bite member may be made of metallic material, and may be adapted for manufacture in a variety of sizes, including adult and pediatric sizes. Alternatively, the bite member may be made of other materials. In embodiments of the invention, the bite member may preferably be made of an autoclavable material, including an autoclavable resin, such as, e.g., an amorphous thermoplastic polyetherimide (PEI) available under the name ULTEM®. Generally, the bite member may be made of material, and in such a way, that when coupled to a bite grip, allows the combination to be soft and compressible between the upper and lower teeth in an elastic manner, thereby providing a spring-like quality. In embodiments, therefore, the bite member may be referred to as the bite spring.

Figure 8:
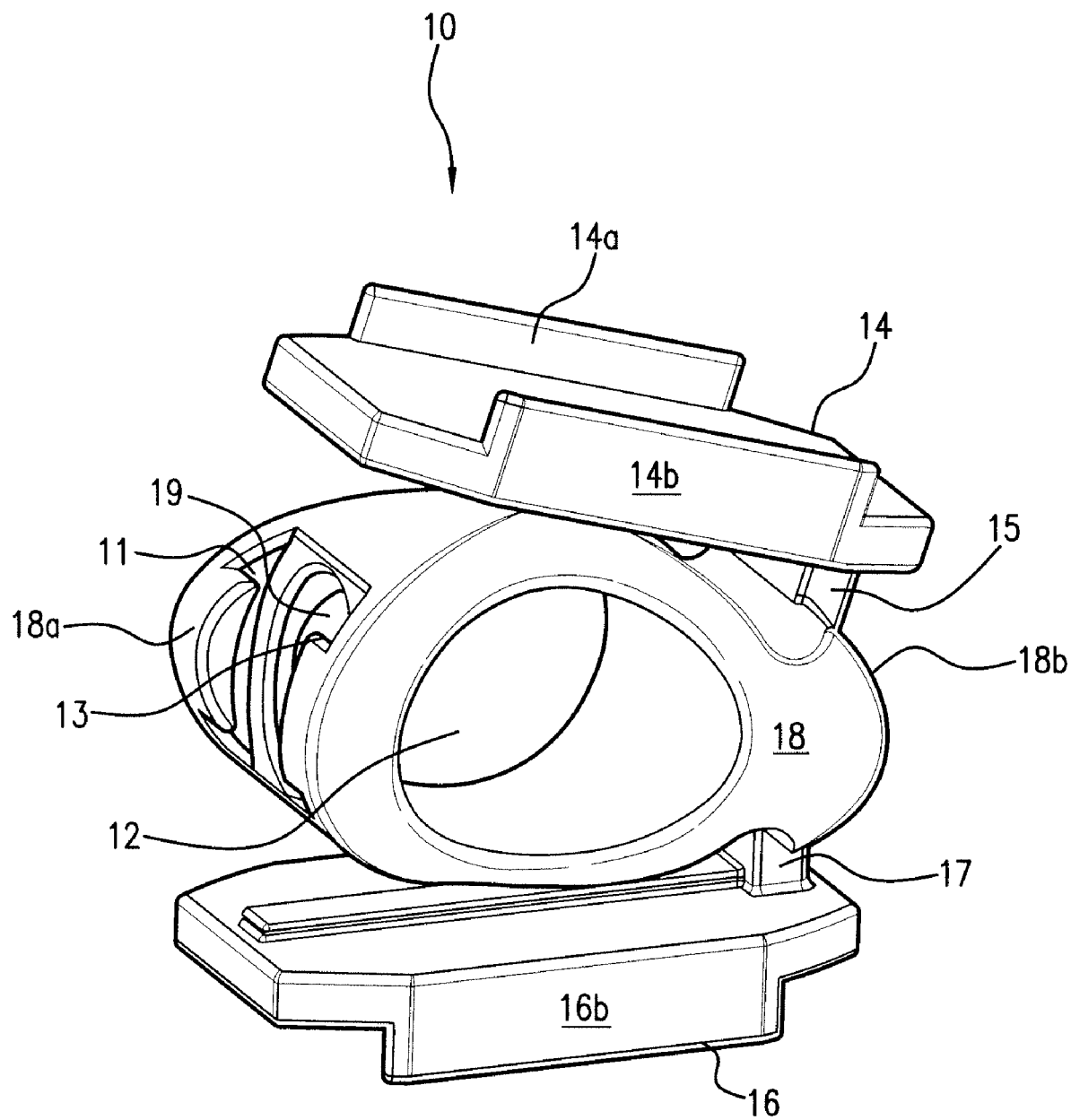
FIG. 8 is a perspective view of a bite member in accordance with an embodiment of the invention.

As shown, e.g., in FIG. 8, in embodiments of the invention, a bite member 10 may be a re-usable (autoclavable) component having an upper member 14 and a lower member 16. The upper and lower members 14, 16 are connected to an intermediate member 18 via respective connection sections 15, 17 proximate a posterior end 18b of the intermediate member 18. The intermediate member 18 also includes a lateral orifice 12 which, as discussed above, may accommodate therethrough a variety of tongue shield aspirators to assist the practitioner in a multitude of differing procedures. In addition, the intermediate member 18 defines an anterior opening 19 through the anterior face 18a thereof, for accommodating an end of an evacuation tube such as, e.g., evacuation tube 30, 230 (see below).

Figure 9:
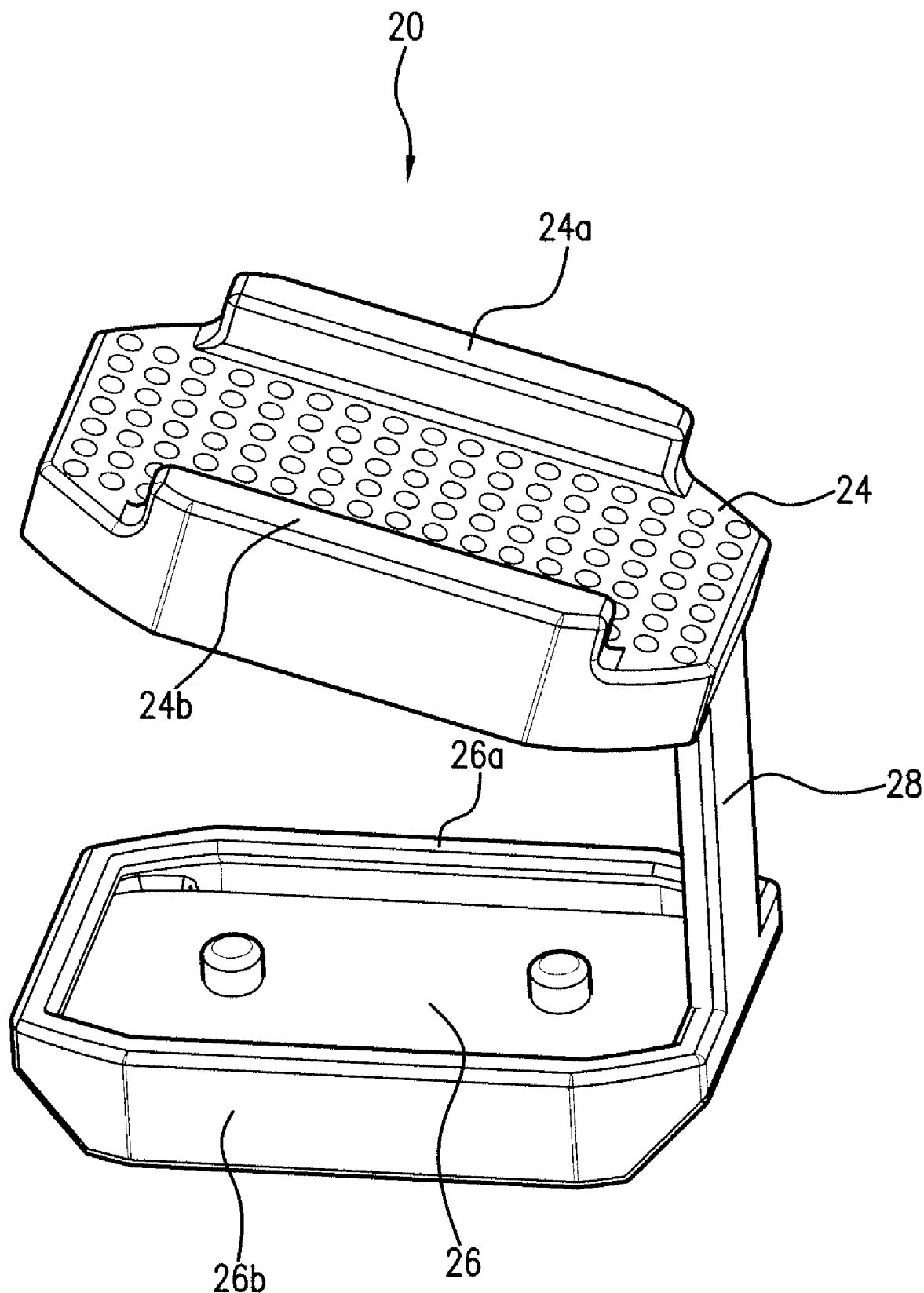
FIG. 9 is a perspective view of a bite grip in accordance with an embodiment of the invention.

FIG. 9 shows a bite grip 20 in accordance with an embodiment of the present invention. The bite grip 20 may generally be a disposable component that is used to cover the upper member 14 and the lower member 16 of the bite member 10, thereby cushioning the patient's teeth from the bite member. To this end, the bite grip 20 includes an upper member 24 and a lower member 26 that are joined to one another by a vertical spine 28. As shown in FIG. 9, the upper member 24 includes opposing pockets 24a, 24b which are configured to receive, respectively, mating protrusions 14a, 14b which project from the upper member 14 of the bite member 10. Similarly, the lower member 26 includes opposing pockets 26a, 26b, which are configured to receive, respectively, mating protrusions 16a (not shown), 16b which project from the lower member 16 of the bite member 10.

In embodiments of the invention, the bite grip 20 may also serve as a retention feature for dental impression material if desired to obtain a "custom" fit to the patient's dental anatomy. The bite grip 20 may be made of a non-latex and/or non-silicone material, and is adapted for manufacture in a variety of sizes, including adult and pediatric sizes.

The purpose of an evacuation tube is to provide fluid communication between the dental chair high-volume vacuum hose and the tongue shield aspirator via the bite grip/bite member combination so as to enable aspiration of fluids and/or debris during dental procedures. Thus, as described more fully below, the evacuation tube extends from within the bite member and out for connection to the industry standard-sized high-volume evacuation (HVE)—and solely the HVE—valve 99 at the dental auxiliary unit. In embodiments of the invention, the evacuation tube may be made of metallic material. Alternatively, the evacuation tube may be made of other materials. In embodiments of the invention, the evacuation tube may preferably be made of an autoclavable material, including an autoclavable resin, such as, e.g., an amorphous thermoplastic polyetherimide (PEI) available under the name ULTEM®.

Figure 10:
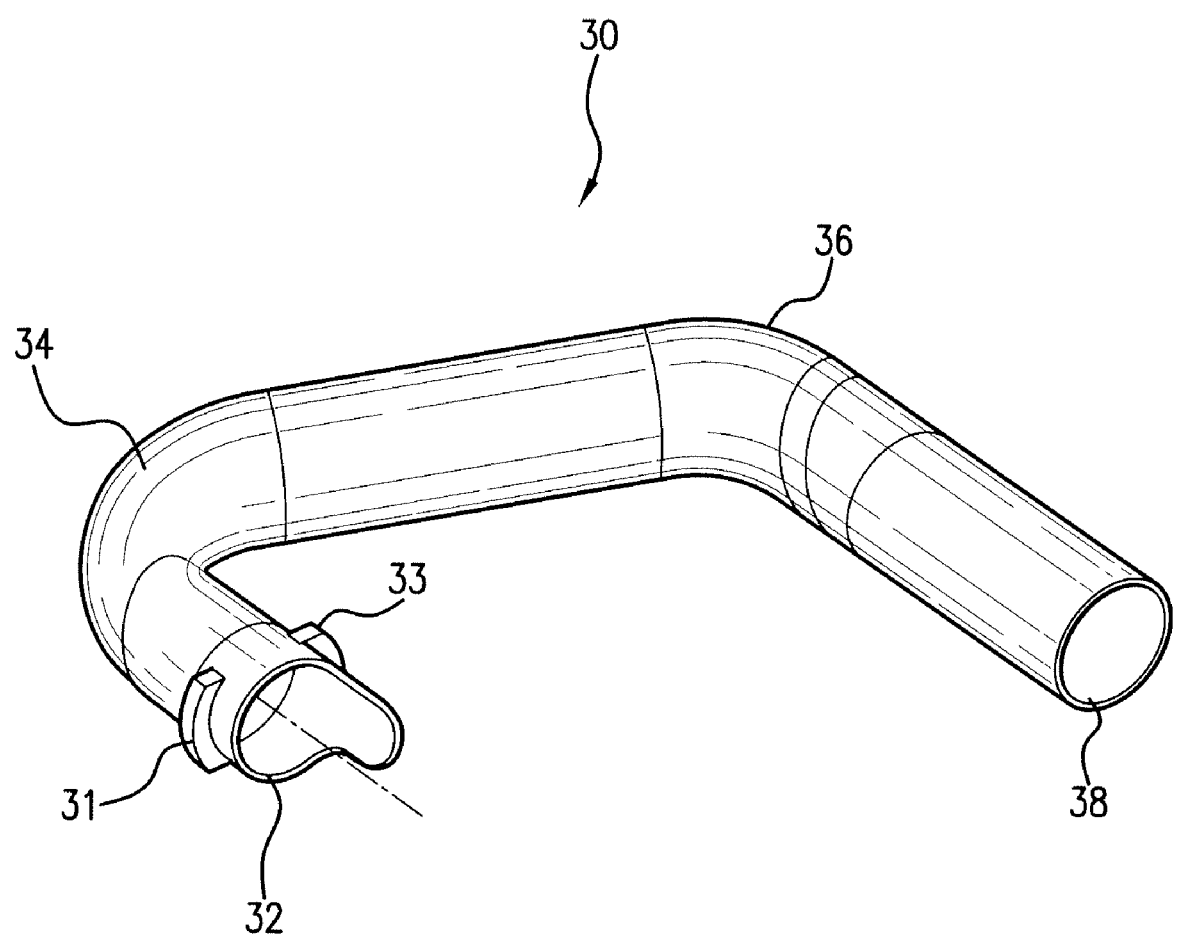
FIG. 10 is a perspective view of an evacuation tube in accordance with an embodiment of the invention.
Figure 11:
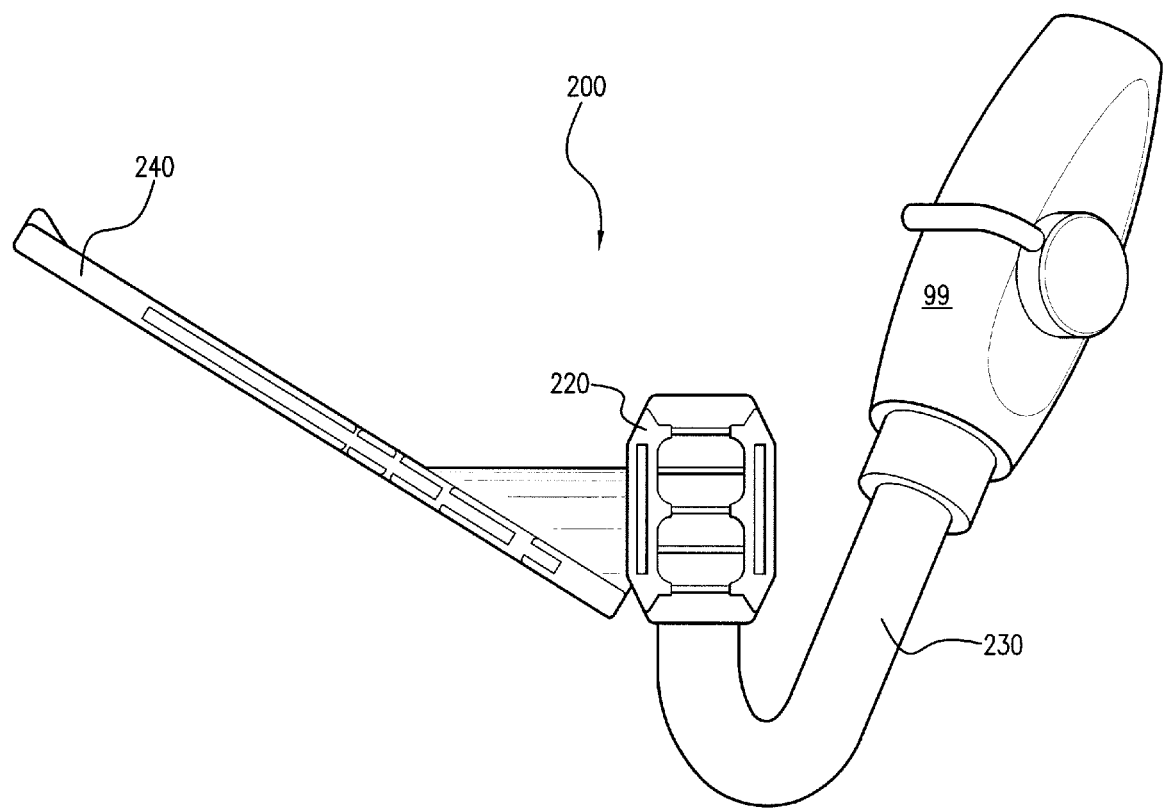
FIG. 11 is a top view of an assembled intra-oral device in accordance with an alternative embodiment of the invention.

FIG. 10 shows an evacuation tube 30 in accordance with an embodiment of the invention. As noted, the evacuation tube 30 may be a re-usable (autoclavable) component which, in embodiments of the invention, may have a "U"-shaped configuration, so as to form a "U tube". The evacuation tube 30 is affixed (i.e., removably attached) to the anterior face 18a of the bite member 10 via a locking mechanism wherein two radial flanges 31, 33 extend from a first end portion 32 of the evacuation tube 30 and are adapted to rotate within two respective mating sockets 11, 13 defined within the anterior face 18a of the bite member 10, thereby interlocking the evacuation tube 30 and the bite member 10. In this way, the evacuation tube 30 is rendered inseparable from the bite spring 10 when pulled in an anterior direction. In addition, when locked, the first end portion 32 of the evacuation tube 30 is in (fluid) communication with the transverse anterior orifice and, therefore, with the longitudinal hollow lumen, of a tongue shield aspirator. When assembled, the connection between the evacuation tube 30 and the transverse anterior orifice of the tongue shield aspirator preferably creates a seal such that no air, fluid, or debris leaks as it travels through the longitudinal hollow lumen and into the evacuation tube.

With the above construction, the evacuation tube exits the patient's mouth anteriorly rather than laterally, thereby creating greater patient comfort and increased operative area for the operator's hands and instruments. As shown, the evacuation tube includes a first bend 34 and a second bend 36, such that its second end 38 may then be attached to the HVE valve 99. See also FIGS. 1 and 2. As shown in these Figures, the evacuation tube 30, and indeed, the overall intra-oral device 1, 100, may be used bilaterally in the mouth.

FIGS. 11-14 show an intra-oral device 200 in accordance with an alternative embodiment of the invention. As shown, the device 200 includes the same overall components that were discussed above, namely, a bite member 210, a bite grip 220, a tongue shield aspirator 240, and an evacuation tube 230 that, at one end, is attached to a HVE valve 99. FIGS. 15-17 provide further details of these components.

Figure 12:
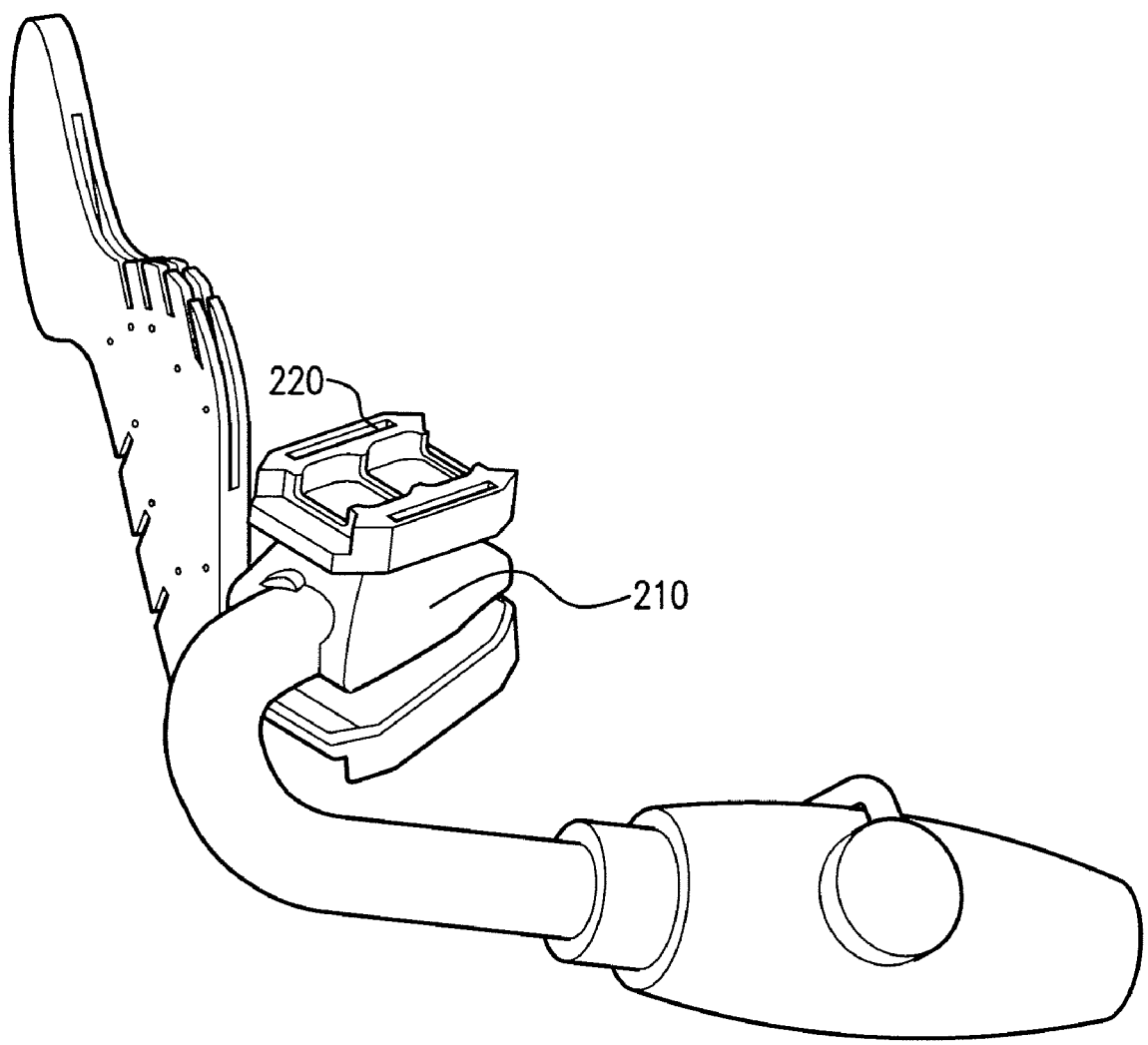
FIG. 12 is a perspective view of the intra-oral device shown in FIG. 11.
Figure 13:
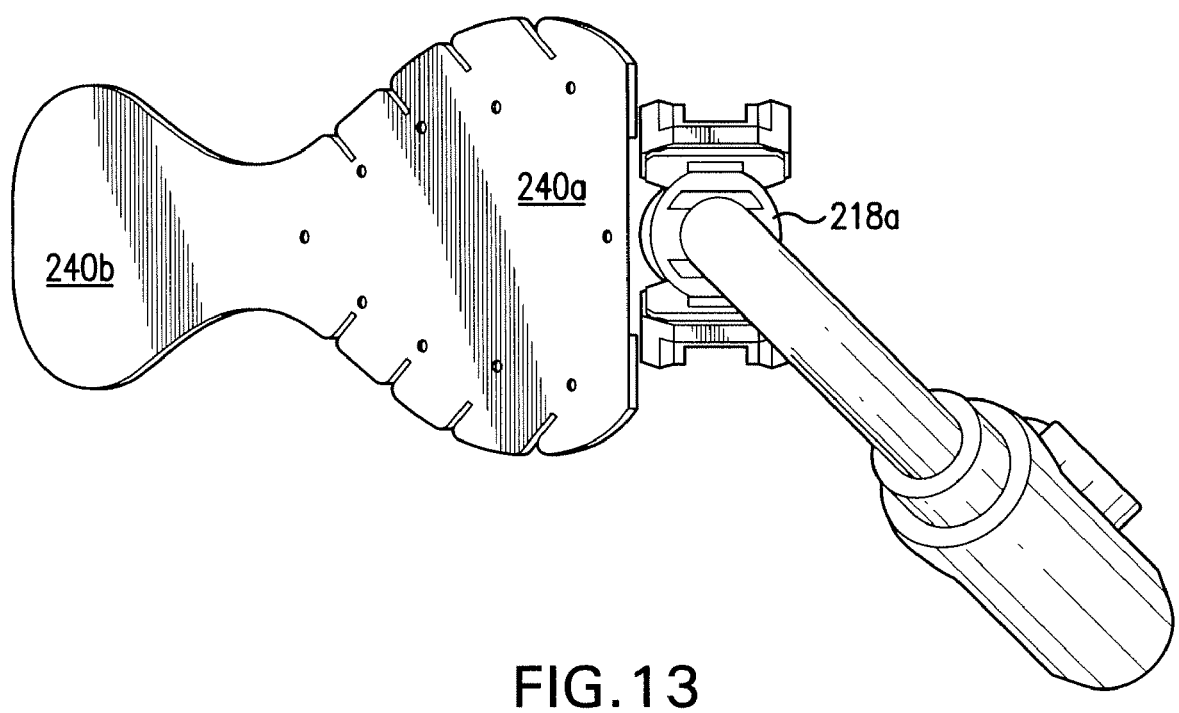
FIG. 13 is an anterior view of the intra-oral device shown in FIG. 11.
Figure 14:
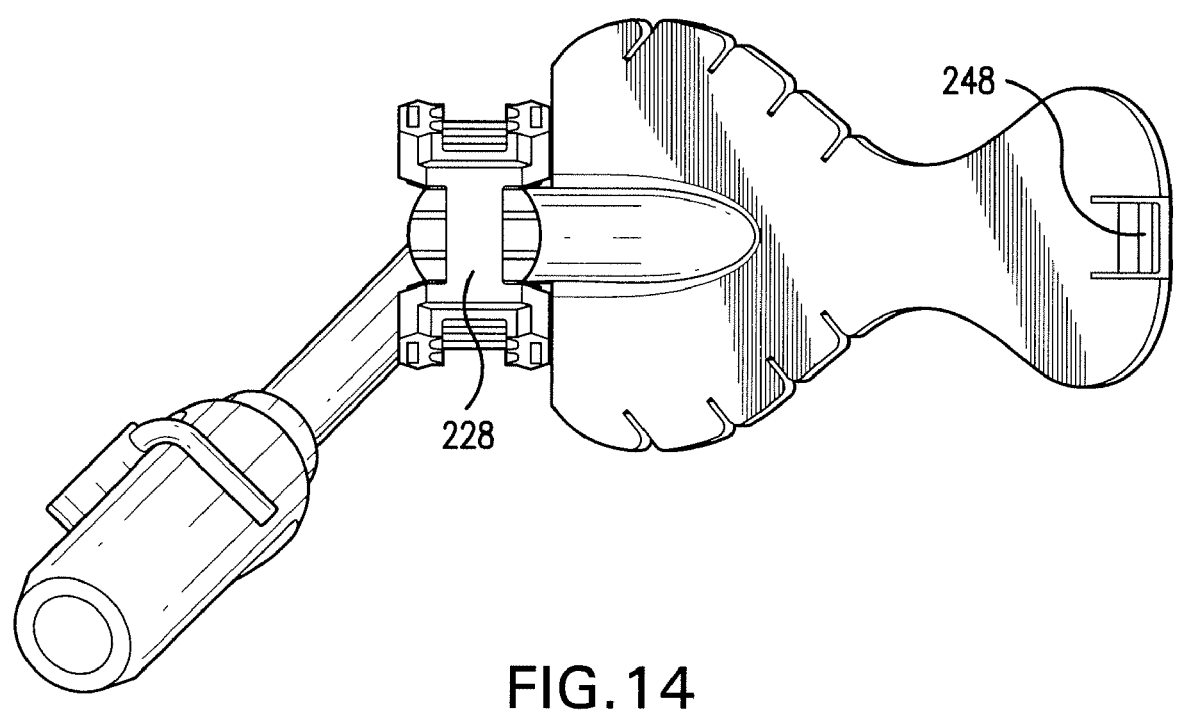
FIG. 14 is a posterior view of the intra-oral device shown in FIG. 11.
Figure 15A:
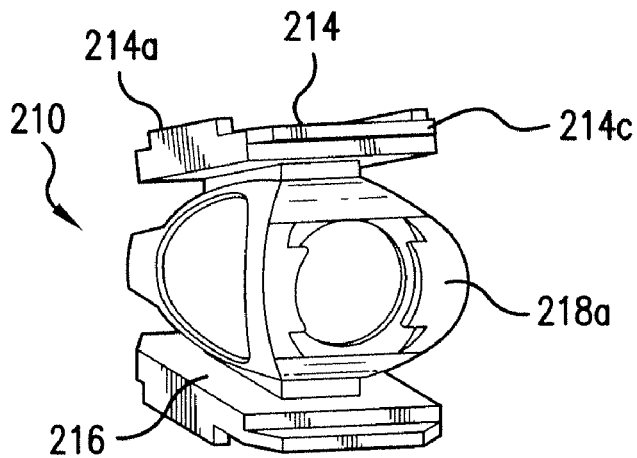
FIG. 15A is a perspective view of a bite member in accordance with an alternative embodiment of the invention.
Figure 15B:
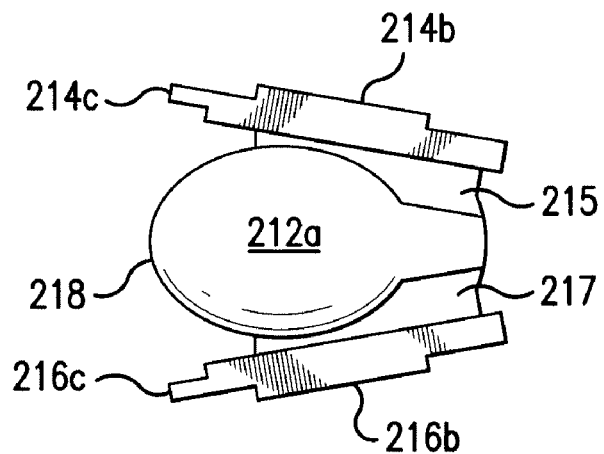
FIG. 15B is a side view of the bite member shown in FIG. 15A.
Figure 15C:
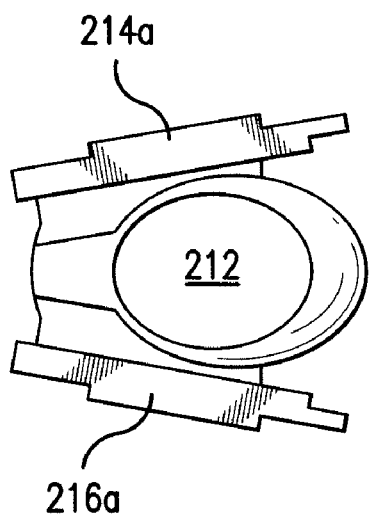
FIG. 15C is a view from an opposite side of the bite member shown in FIG. 15B.

As shown in FIGS. 15A-15C, the bite member 210 includes an upper member 214 and a lower member 216, wherein the anterior edge 214c of the upper member 214 and the anterior edge 216c of the lower member 216 are beveled. In addition, as compared with the bite member 10, wherein the upper member 14 and the lower member 16 are connected to an intermediate member 18 via respective connection sections 15, 17 proximate a posterior end 18b of the intermediate member 18, in the embodiment shown in FIGS. 15A-15C, the connection sections 215, 217 extend anteriorly through at least the longitudinal midpoint of the intermediate member 218 so as to fill a portion of the space between the intermediate member 218 and the upper and lower members 214, 216. As shown in FIGS. 12, 15B, and 15C, the intermediate member 218 includes a lateral orifice 212 to allow insertion of a tongue shield aspirator into the body of the intermediate member 218. However, in contrast with the embodiments shown in FIG. 1-8, the orifice 212 opens on only one side of the intermediate member 218, and is closed off on the opposite side 212a.

Figure 16A:
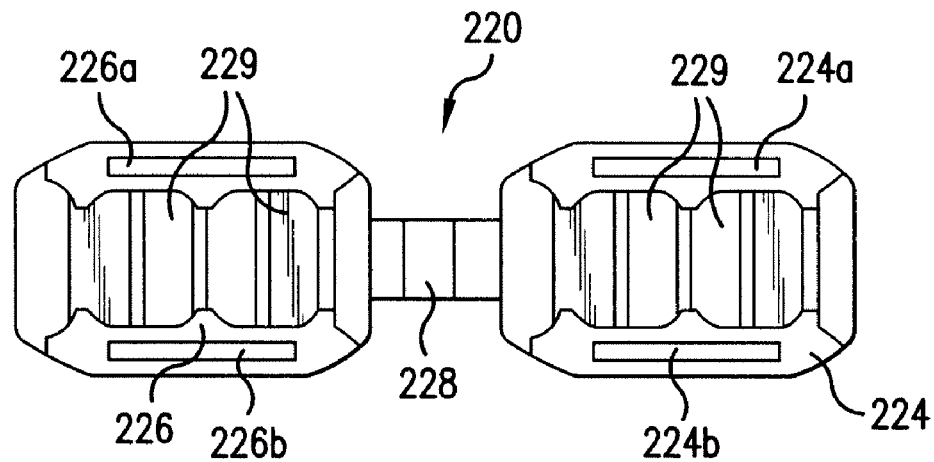
FIG. 16A is a top plan view of an opened bite grip in accordance with an alternative embodiment of the invention.
Figure 16B:
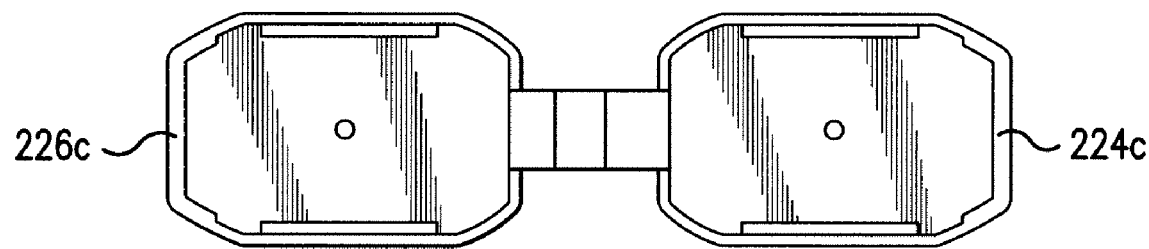
FIG. 16B is a bottom plan view of the bite grip shown in FIG. 16A.

The bite grip 220 shown in FIGS. 16A and 16B includes an upper member 224 that is connected to a lower member 226 via a spine 228; each of the upper and lower members includes respective pockets 224a, 224b and 226a, 226b for receiving therein respective protrusions 214a, 214b and 216a, 216b on the upper and lower members 214, 216 of the bite member 210. In addition, at a respective anterior edge thereof, the upper member 224 includes a lip 224c, and the lower member 226 includes a lip 226c, wherein the former is configured to fit around the beveled edge 214c, and the latter is configured to fit around the beveled edge 216c, of the bite member 210. Moreover, each of the upper member 224 and the lower member 226 includes, on its respective outer surface, shaped regions 229, which are adapted to serve as "molar" guides for a more secure fit between the patient's upper and lower jaws.

Figure 17A:
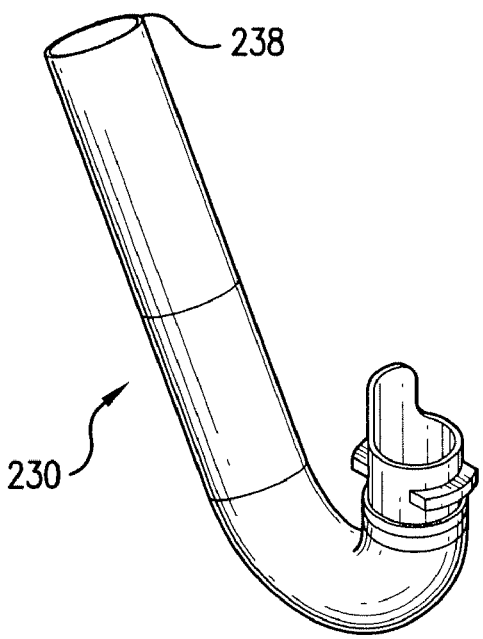
FIG. 17A is a perspective view of an evacuation tube in accordance with an alternative embodiment of the invention.
Figure 17B:
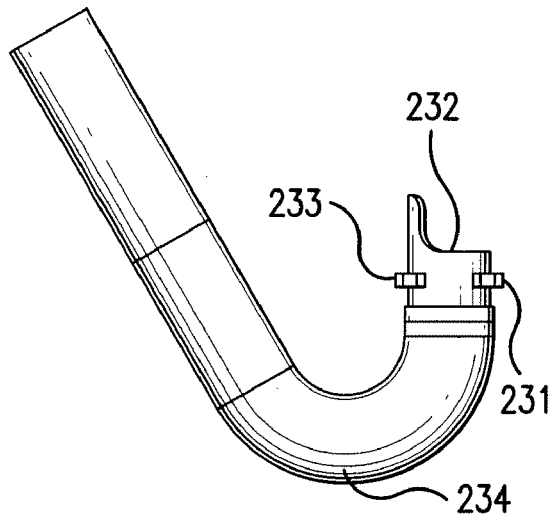
FIG. 17B is a side elevational view of the evacuation tube shown in FIG. 17A.
Figure 17C:
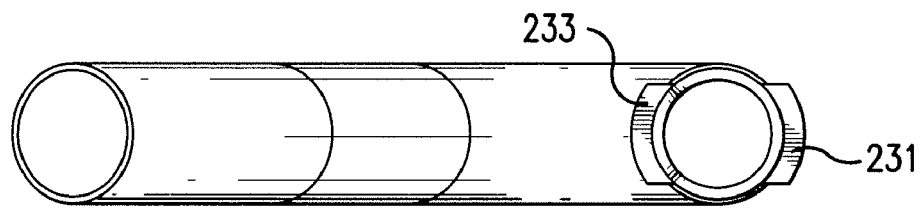
FIG. 17C is an end view of the evacuation tube shown in FIG. 17A.

FIGS. 17A-17C show an evacuation tube 230 having a first end portion 232, a second end 238, and two radial flanges 231, 233 which extend from the first end portion 232 and are adapted to rotate within two respective mating sockets defined within the anterior face 218a of the bite member 210. In this embodiment, the evacuation tube 230 includes a single bend 234. Nevertheless, given that, when assembled, the first end portion 232 is affixed (i.e., removably attached) to the anterior face 218a of the bite member 210, the evacuation tube 230 still exits the patient's mouth anteriorly rather than laterally, thereby creating greater patient comfort and increased operative area for the operator's hands and instruments.

Figure 18:
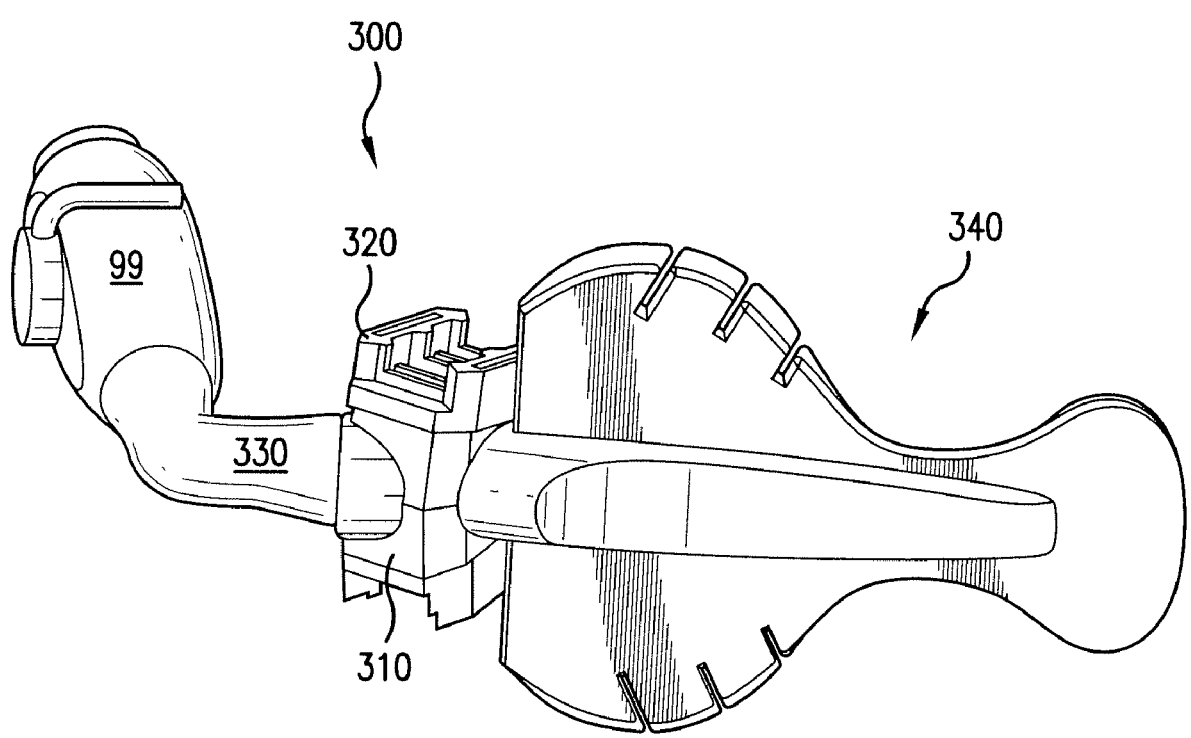
FIG. 18 is an anterior view of an assembled intra-oral device in accordance with an embodiment of the invention.
Figure 19:
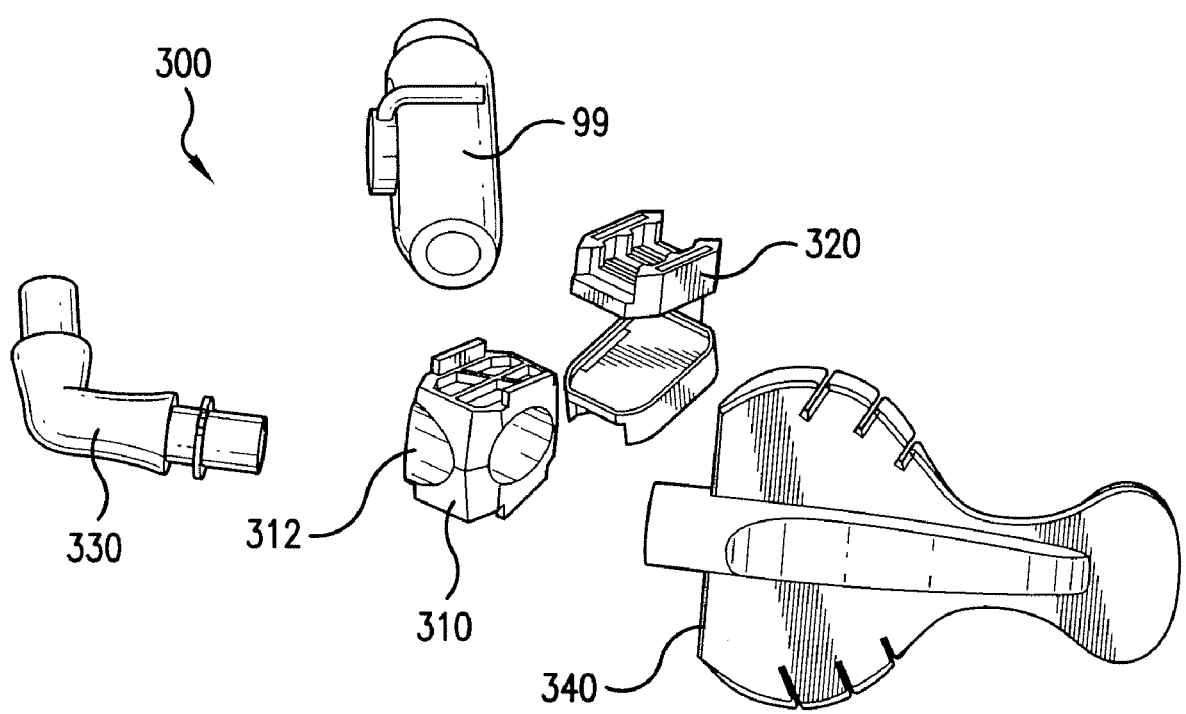
FIG. 19 is an exploded view of components of the intra-oral device shown in FIG. 18.

FIGS. 18-19 show an intra-oral device 300 in accordance with another embodiment of the invention. As shown, the device 300 includes the same overall components that were discussed above, namely, a bite member 310, a bite grip 320, a tongue shield aspirator 340, and an evacuation tube 330 that, at one end, is attached to a HVE valve 99. FIGS. 20-23 provide further details of these components.

As shown in FIGS. 20A-20E, the bite member 310 includes a top side 314 and a bottom side 316, wherein the anterior edge 314c of the top side 314 and the anterior edge 316c of the bottom side 316 may be beveled. In addition, the top side 314 and bottom side 316 of the bite member 310 lie in divergent planes, i.e., respective planes that diverge from one another at an acute angle so as to accommodate a patient's mouth in the open position. In this way, the patient's mouth may be maintained open at various angles depending on the actual position of the bite member when placed in the mouth. For example, given the acute angle between the divergent planes of the top side 314 and bottom side 316, the father back (i.e., posteriorly) in the mouth the bite member is placed, the more open (i.e., the larger the opening of) the mouth. Obviously, the extent of such opening will be limited by the patient's anatomy.

As shown in FIGS. 19 and 20, the bite member 310 includes a conduit 312 to allow insertion of a tongue shield aspirator and an evacuation tube into the body of the bite member. However, in contrast with the embodiments described previously, the conduit 312 extends through the bite member 310 at an oblique angle with respect to the vertical. Thus, the conduit has a distal end 312a that is coplanar with a distal side 315 of the bite member 310 and is configured to matingly receive a neck of a tongue shield aspirator, and a proximal end 312b that extends through the corner that connects the bite member's proximal side 317 and anterior side (i.e., anterior face) 318 and is configured to receive an end of an evacuation tube. As will be described below, offsetting of the conduit—and, therefore, of the distal end 312a thereof—at an oblique angle decreases resistance to airflow through the tongue shield aspirator-bite member combination.

As has been noted previously, the bite members described herein may be generally made of material, and in such a way, that when coupled to a bite grip, may create a spring-like quality. In this regard, the top side 314 of the bite member 310 includes cavities (or core-outs) 314d that allow for and/or enhance the spring effect when covered with an upper member of a bite grip. Similarly, the bottom side 316 of the bite member 310 includes cavities 316d that allow for and/or enhance the spring-like quality when covered with a lower member of a bite grip.

Figure 21A:
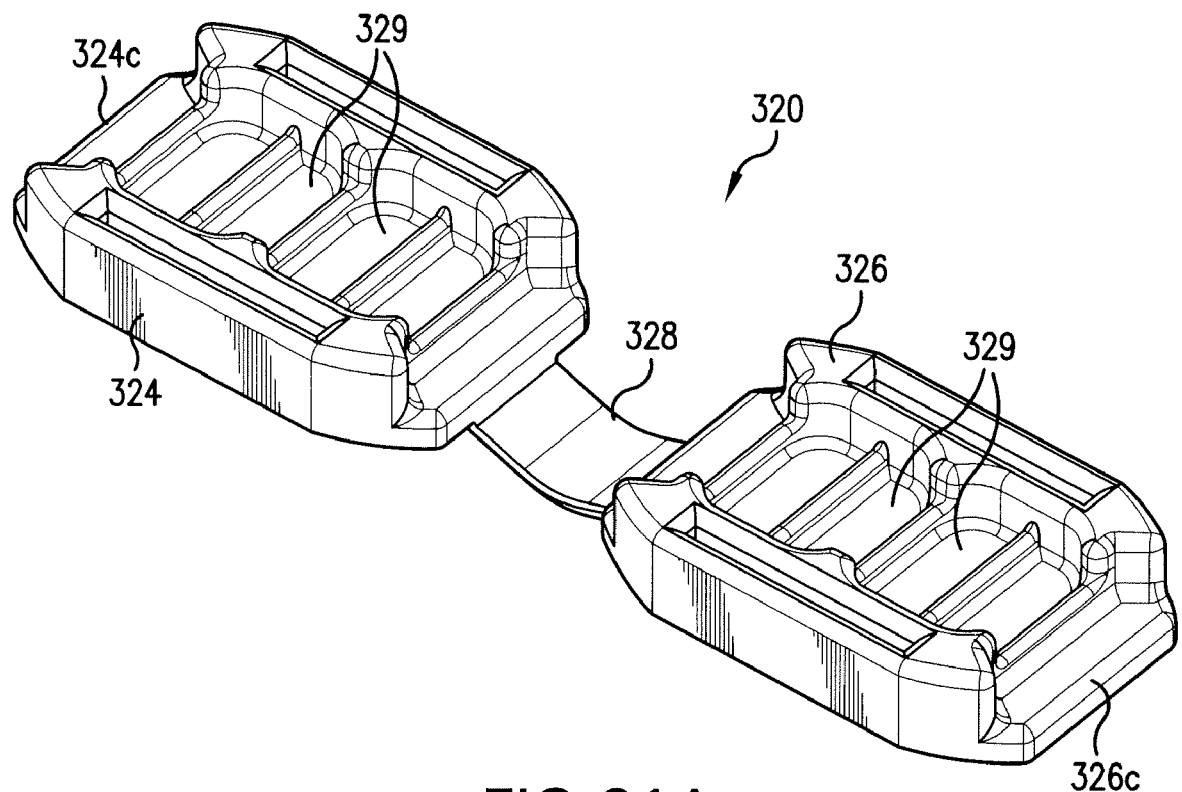
FIG. 21A is a top perspective view of a bite grip in accordance with an embodiment of the invention.
Figure 21B:
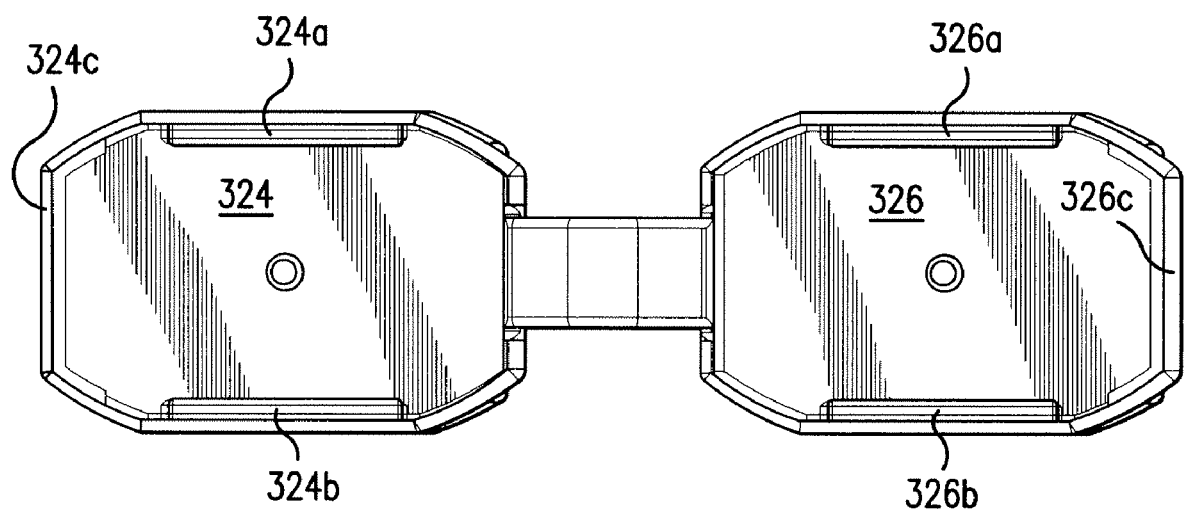
FIG. 21B is a bottom plan view of the bite grip shown in FIG. 21A.

The bite grip 320 shown in FIGS. 21A and 21B is substantially identical to the bite grip 220 shown in FIGS. 16A and 16B. Thus, as described previously, the bite grip 320 includes an upper member 324 that is connected to a lower member 326 via a spine 328. The upper member 324 includes pockets 324a, 324b for receiving therein respective protrusions 314a, 314b on the top member 314 of the bite member 310. Similarly, the lower member 326 includes pockets 326a, 326b for receiving therein respective protrusions 316a, 316b on the bottom member 316 of the bite member 310. In addition, at a respective anterior edge thereof, the upper member 324 may include a lip 324c, and the lower member 326 may include a lip 326c, with the former being configured to fit around the beveled edge 314c, and the latter being configured to fit around the beveled edge 316c, of the bite member 310. Moreover, each of the upper member 324 and the lower member 326 may include, on its respective outer surface, shaped regions 329, which are adapted to serve as "tooth" or "molar" guides for a more secure fit between the patient's upper and lower jaws.

Figure 22A:
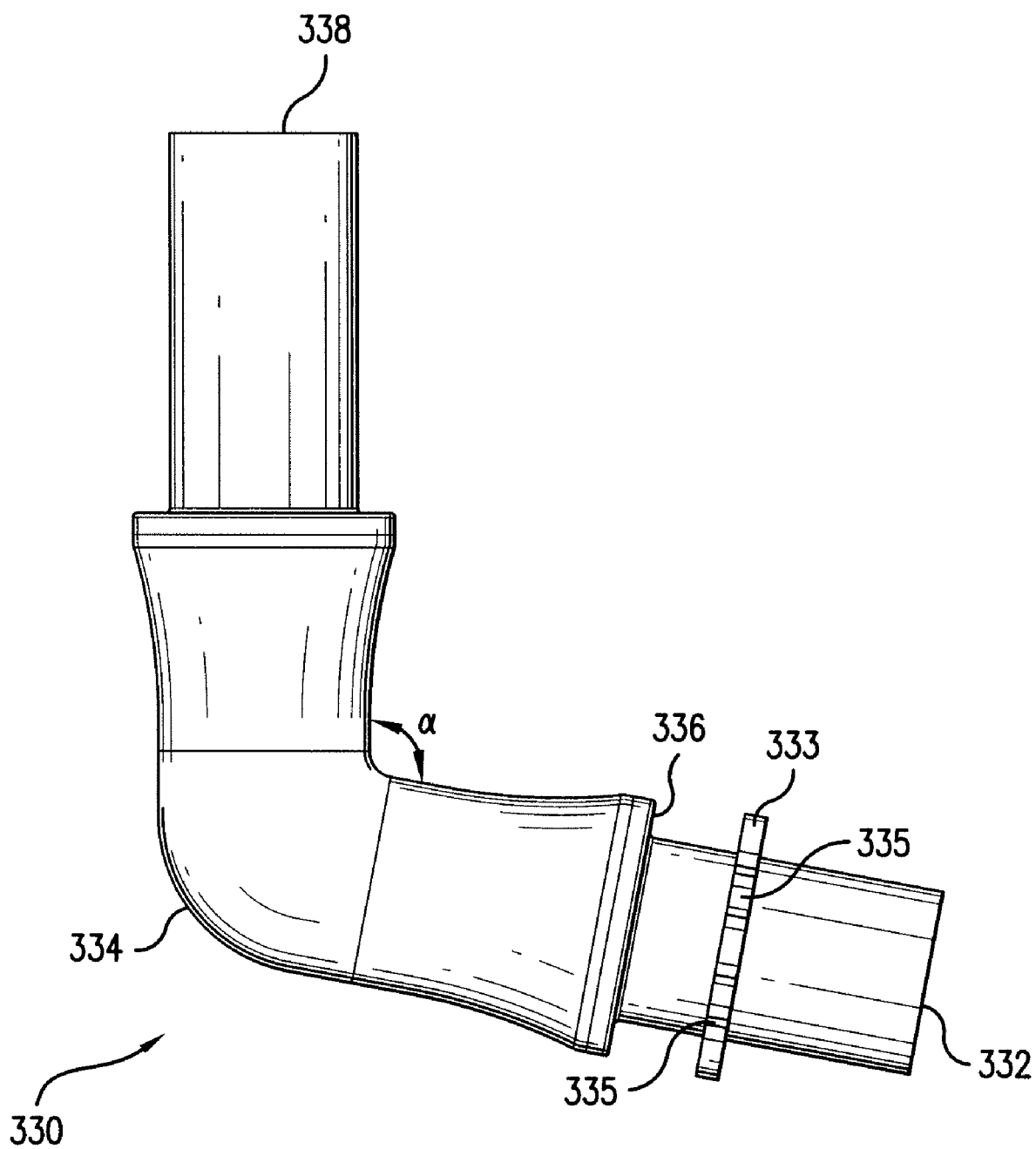
FIG. 22A is a side elevational view of an evacuation tube in accordance with an embodiment of the invention.
Figure 22B:
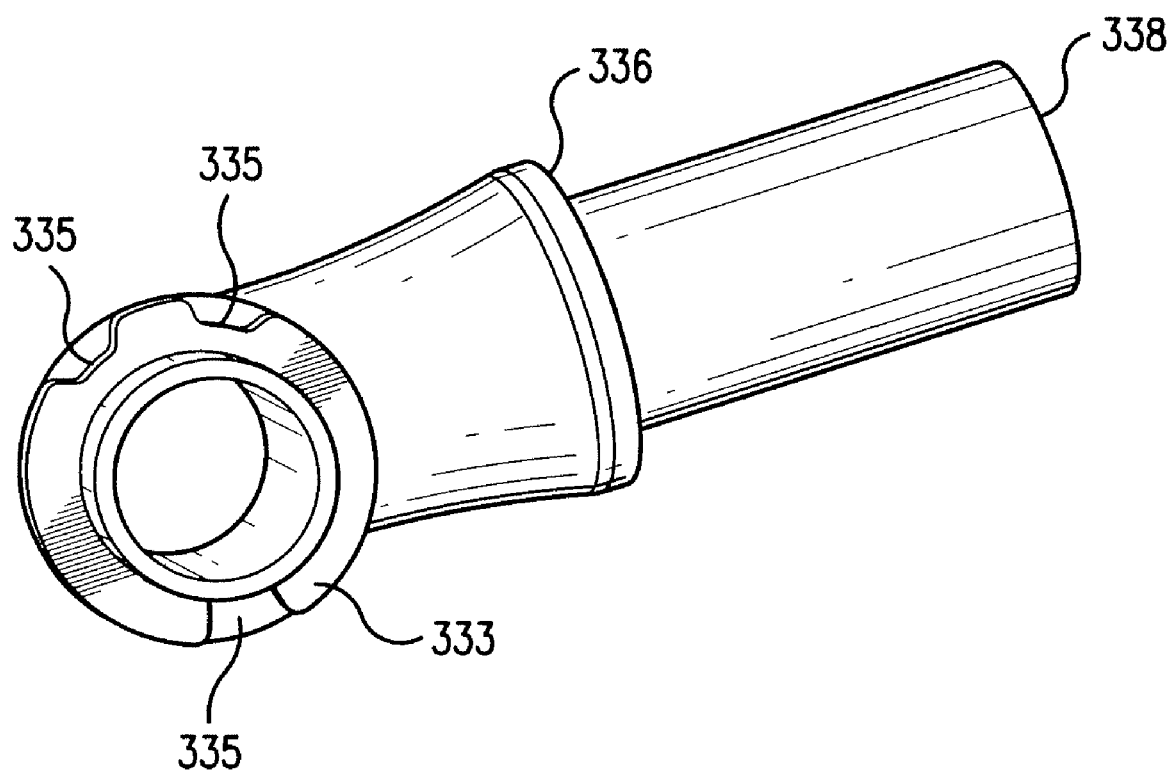
FIG. 22B is an end view of the evacuation tube shown in FIG. 22A.

FIGS. 22A and 22B show an evacuation tube 330 having a first end 332, which is configured for slideable insertion through the proximal end 312b of the bite member 310, and a second end 338, which is configured to be removably coupled directly to a high-volume evacuation (HVE) valve. As shown, the evacuation tube 330 may include a single bend 334 so as to be generally L-shaped, with an inner angle α approximately equal to 100°. In embodiments of the invention, the angle α may be between about 85° and about 110°.

Proximate its first end 332, the evacuation tube 330 may include a radial flange 333 which, in turn, includes one or more radial indentation(s) 335. In the illustrative embodiment shown in FIGS. 22A and 22B, the radial flange 333 includes three such indentations, which are circumferentially spaced apart at irregular intervals. As shown, e.g., in FIG. 20E, the bite member 310 may include one or more internal (radial) protrusion(s) 313 which extend radially inwards, towards the central axis of the conduit 312, and extend longitudinally from the proximal end 312b of the conduit 312 towards its distal end 312a. In the illustrative embodiment shown, the bite member 310 includes three such protrusions, which are also circumferentially spaced apart at irregular intervals, but disposed such that, in a given orientation, and only in that orientation, the protrusions 313 will be aligned with the indentations 335 of the evacuation tube 330.

The above-described combination of indentation(s) and protrusion(s) provides a lock-and-key locking mechanism for maintaining the evacuation tube 330 in a longitudinally-locked, but rotatable relationship relative to the bite member 310. In practice, in order to detachably secure the evacuation tube 330 to the bite member 310 when the latter is held between a patient's upper and lower teeth (e.g., in the position shown in FIG. 20E), the indentations 335 are first lined up with the protrusions 313, and the first end 332 of the evacuation tube 330 is moved inwardly through the proximal end 312b of the conduit 312. Once the edge 336 of the evacuation tube 330 has reached the protrusions 313, the evacuation tube 330 is rotated, either clockwise or counter-clockwise, to lock the evacuation tube 330 with respect to the bite member 310. In order to remove the evacuation tube, the above-described process is reversed, wherein the evacuation tube is turned until the indentations 335 are again aligned with the protrusions 313, and then the evacuation tube is pulled outwardly.

Figure 20A:
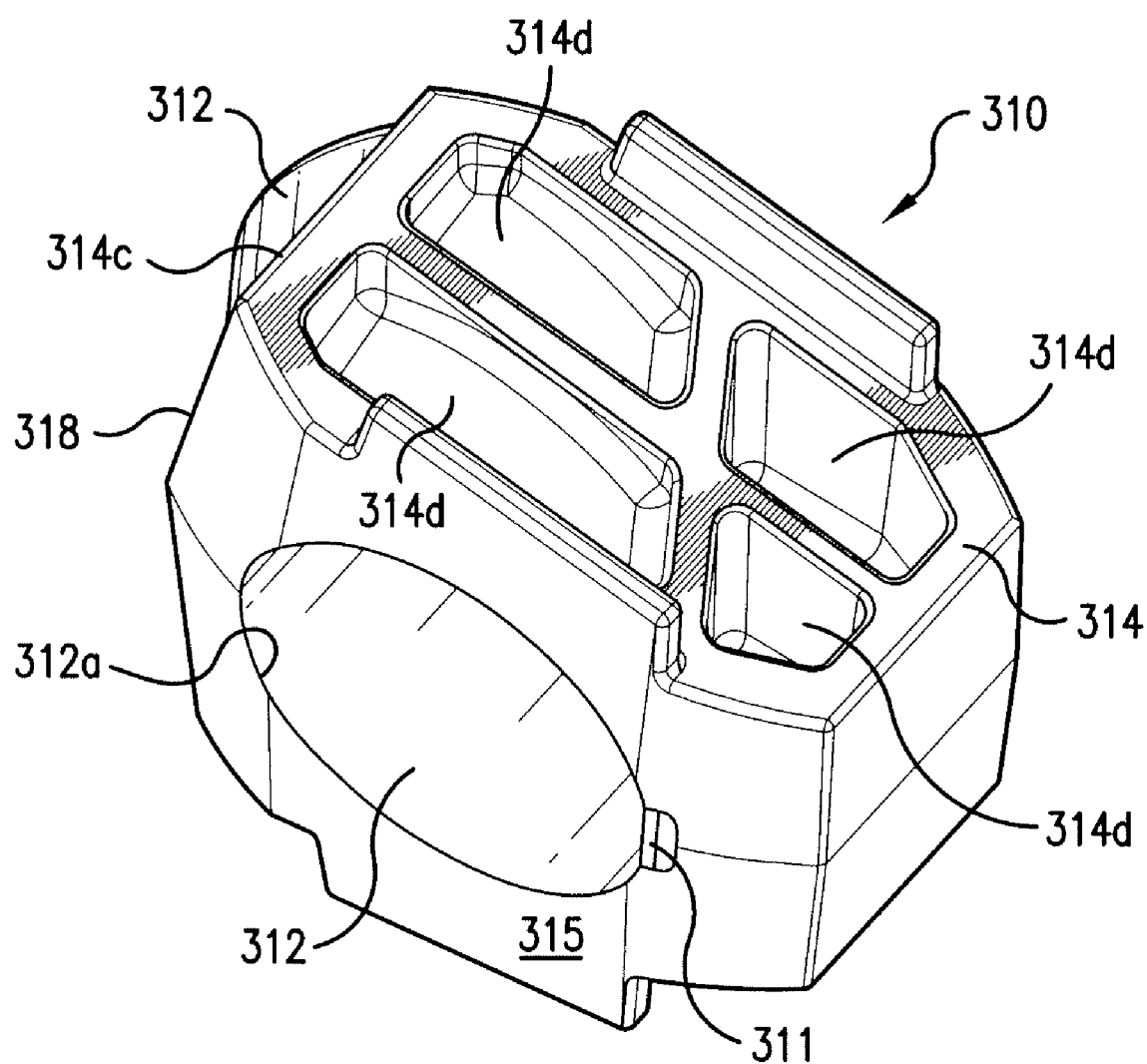
FIG. 20A is a top perspective view of a bite member in accordance with an embodiment of the invention.
Figure 20B:
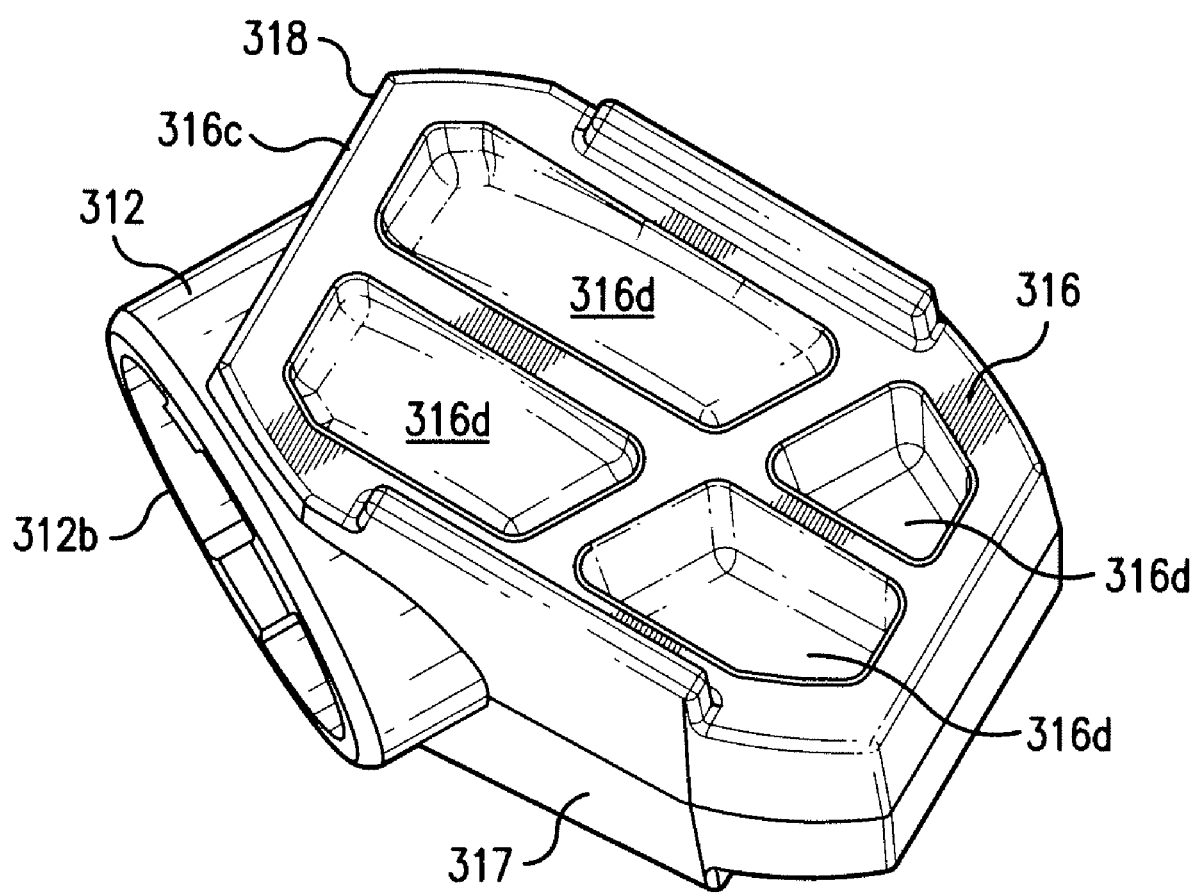
FIG. 20B is bottom perspective view of the bite member shown in FIG. 20A.
Figure 20C:
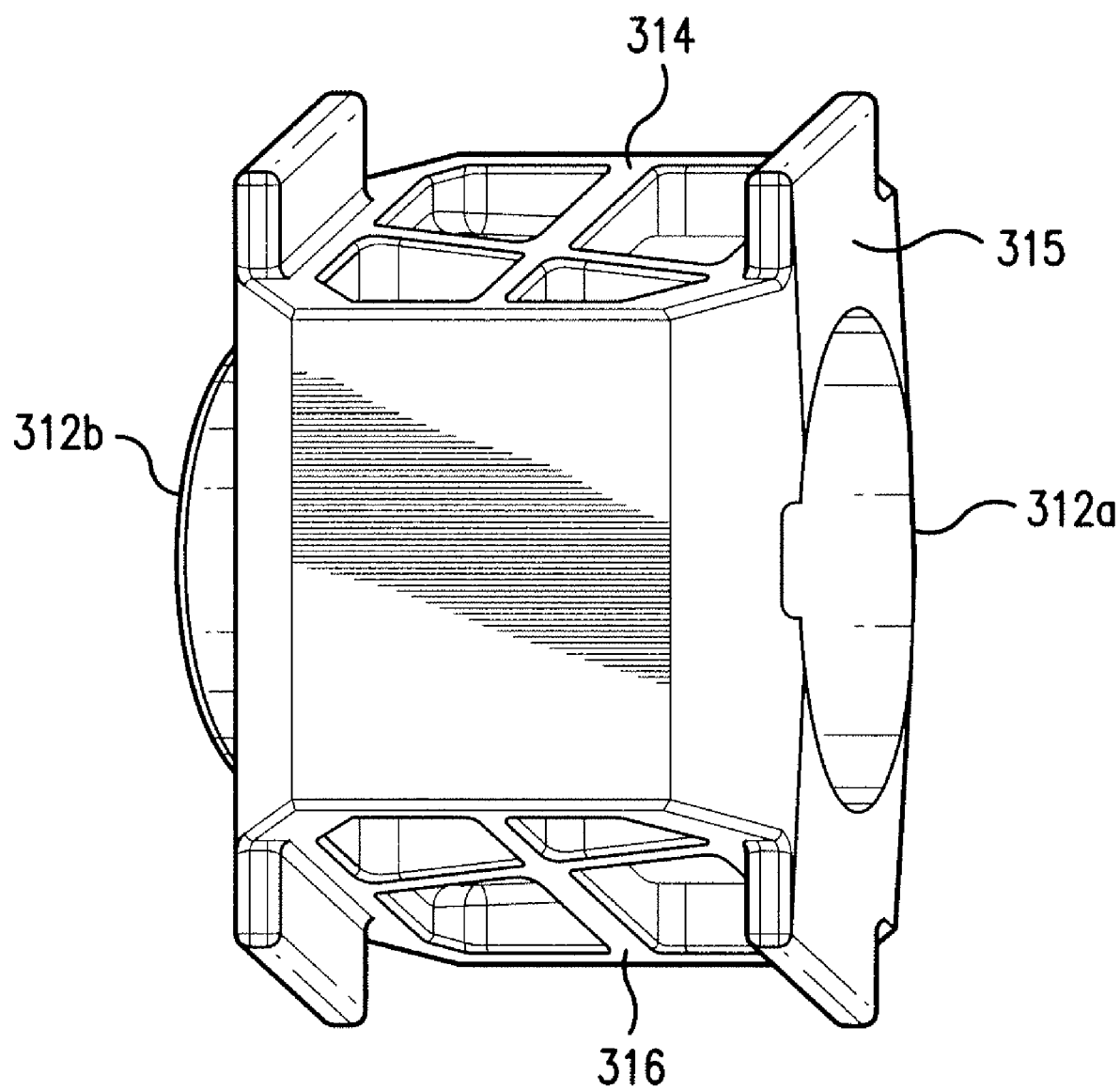
FIG. 20C is a posterior view of the bite member shown in FIG. 20A.
Figure 20D:
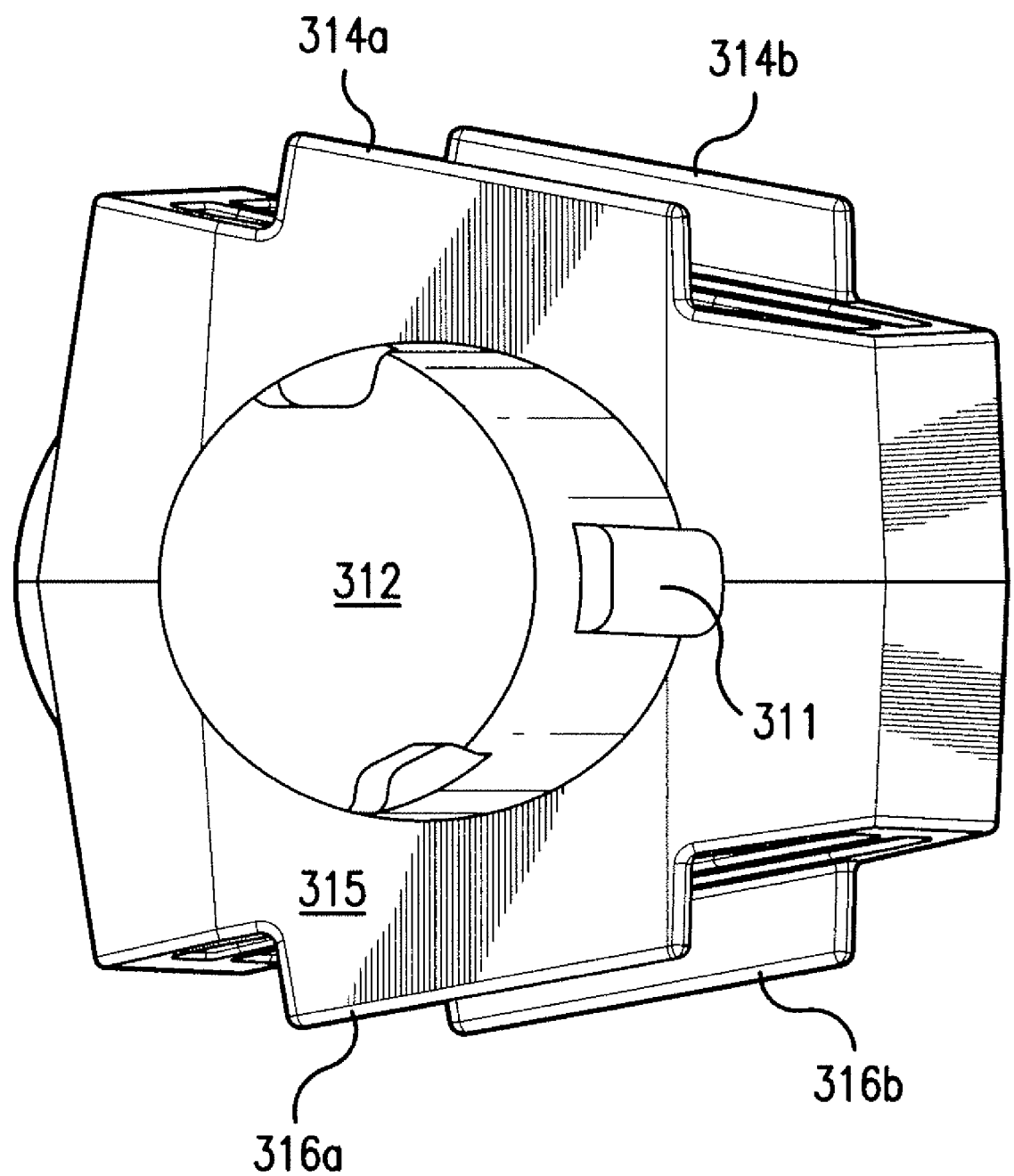
FIG. 20D is a distal side view of the bite member shown in FIG. 20A.
Figure 20E:
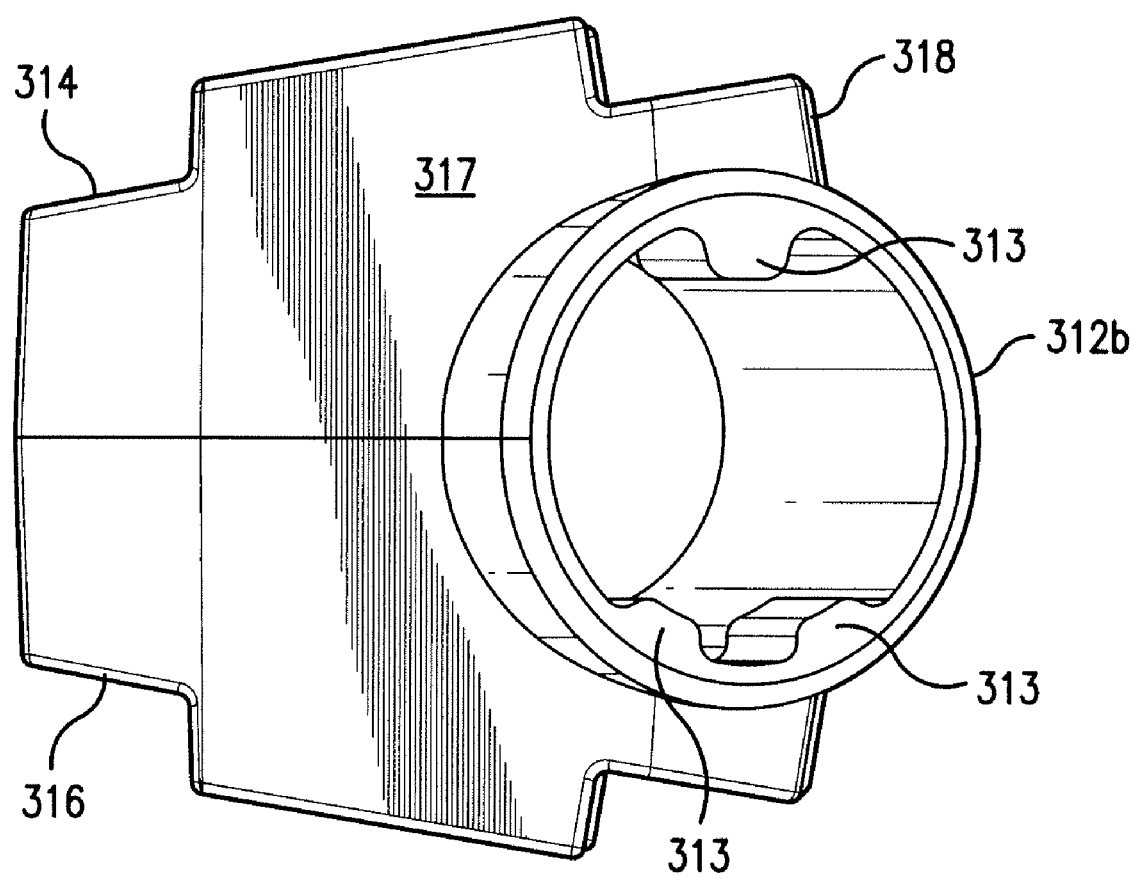
FIG. 20E is a proximal side view of the bite member shown in FIG. 20A.

In embodiments of the invention, the protrusions 313 and indentations 335 may be positioned such that the evacuation tube 330 can be inserted into, and removed from, the bite member 310 only when rotated in the anterior position. Thus, by way of example, FIG. 20E shows the position of the bite member 310 as it would be held between a patient's right-hand upper and lower teeth. The perspective of FIG. 20E is therefore that of one looking at the patient's right profile. With reference to FIG. 18, the evacuation tube must be connected to the bite member 310 shown in FIG. 20E such that, in use, the second end 338 of the evacuation tube points generally to the left of the diagram, i.e., away from the patient's mouth. For ease of discussion, this may be referred to as "Position 2". However, given the placement of the protrusions 313, the latter will be aligned with the indentations 335 only when the evacuation tube 330 is oriented such that its second end 338 points generally to the right of the diagram. For ease of discussion, this may be referred to as "Position 1". In practice, therefore, once the protrusions and mating indentations have been aligned and the first end 332 of the evacuation tube is inserted into the conduit 312, the evacuation tube 330 is rotated about 180° so as to be placed in Position 2. Given that the evacuation tube may be separated from the bite member only in Position 1, the lock-and-key mechanism ensures that the evacuation tube will not detach from the bite member during use, even if the evacuation tube-HVE valve assembly happens to be rotated by a few degrees, as long as the evacuation tube is not rotated all the way back to Position 1. In addition, given the configuration of the conduit 312 and the evacuation tube 330, during use, the evacuation tube 330 exits the patient's mouth at the conduit's oblique angle, rather than laterally, and then bends at an angle α, thereby creating greater patient comfort and increased operating space for the operator's hands and instruments.

Figure 23A:
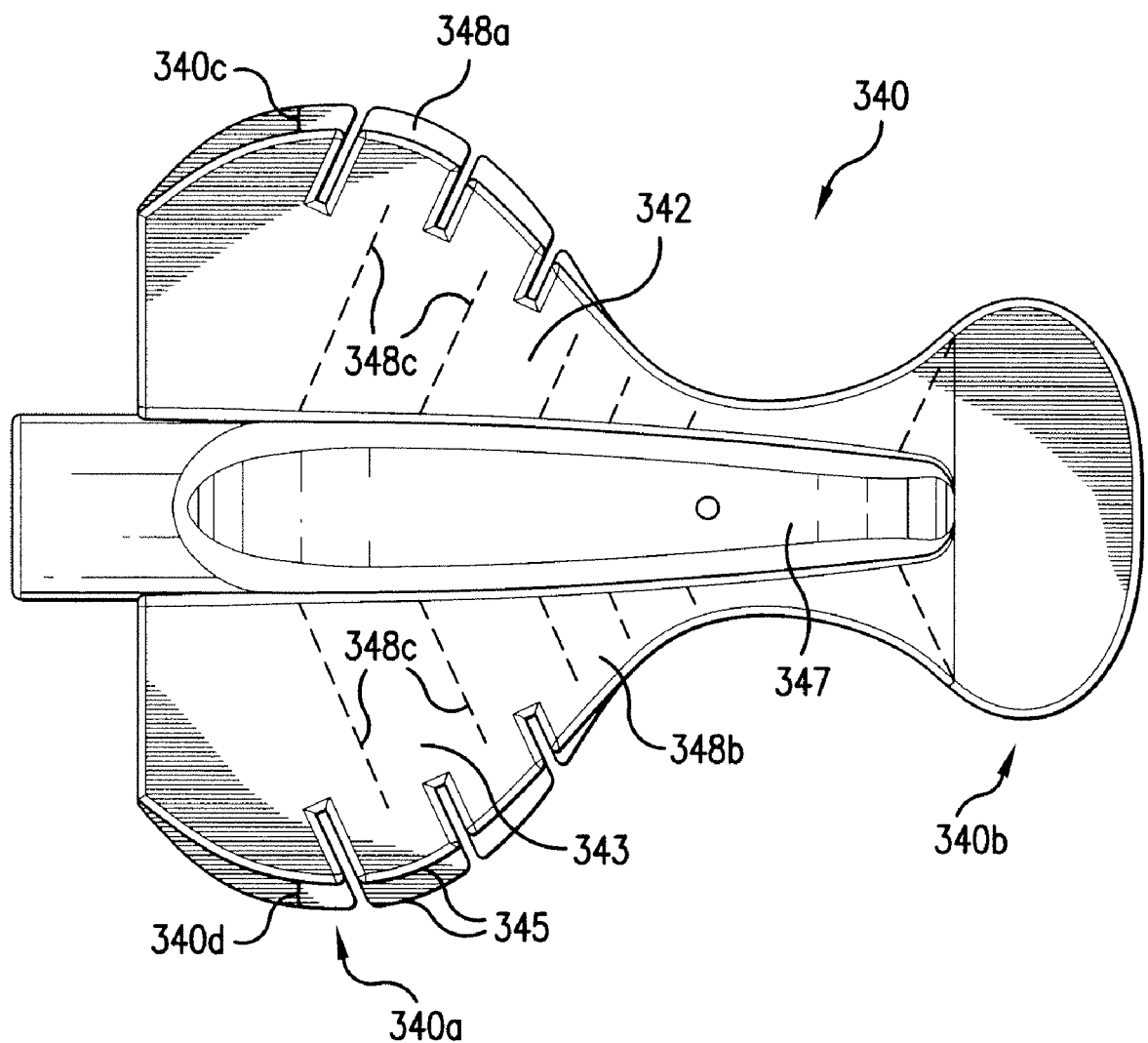
FIG. 23A is an anterior view of a tongue shield aspirator in accordance with an embodiment of the invention.
Figure 23B:
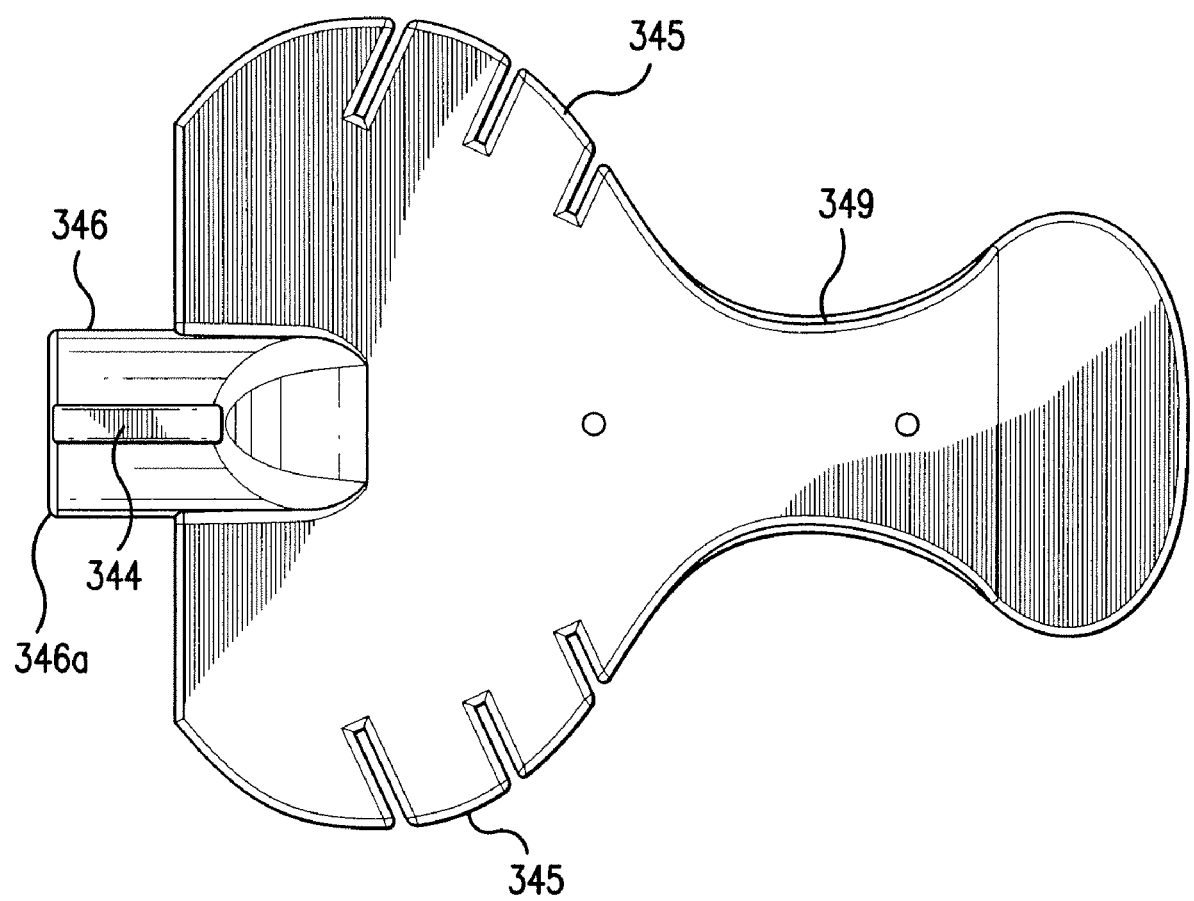
FIG. 23B is a posterior view of the tongue shield aspirator shown in FIG. 23A.
Figure 23C:
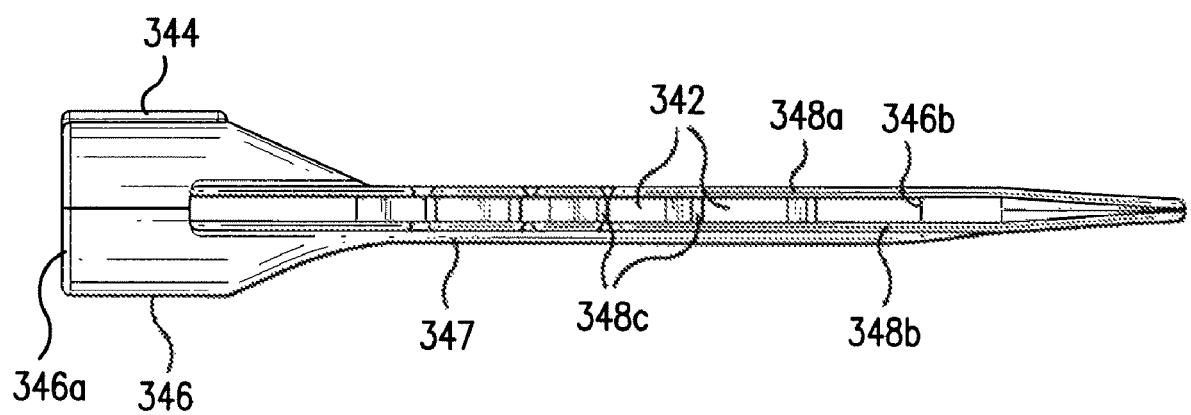
FIG. 23C is a top side view of the tongue shield aspirator shown in FIG. 23A.

FIGS. 23A-C show a tongue shield aspirator 340 in accordance with an embodiment of the present invention. The tongue shield aspirator 340 includes features that are similar to those described above in connection with the tongue shield aspirators 40, 240 shown in FIGS. 3 and 4. Specifically, the tongue shield aspirator 340 has a first (proximal) flap 340a, which is configured to retract a patient's tongue, and a second (distal) flap 340b, which is configured to retract a patient's cheek. The first and second flaps are joined to one another at a transition section 349 such that, when viewed from the perspectives shown in FIGS. 23A and 23B, the transition section 349 forms the narrowest section of the tongue shield aspirator 340, thereby forming an isthmus between the flaps 340a, 340b. As before, it is noted that, although the flaps 340a, 340b are described as being "joined" at the transition section 349, this is simply for ease of reference. In practice, the tongue shield aspirator 340 may be manufactured as a one-piece, or unitary, component, or the two flaps 340a, 340b may be manufactured separately, and then coupled to one another at the transition section 349.

The tongue shield aspirator 340 includes a longitudinal hollow lumen (not shown, but substantially identical to the longitudinal hollow lumen 41 shown in FIG. 3) that is in fluid communication with a multiplicity of channels that may extend at an angle therefrom. More specifically, the proximal flap 340a and/or the distal flap 340b of the tongue shield aspirator 340 may be formed from a first (posterior) layer 348a and a second (anterior) layer 348b which are connected to, but spaced apart from, one another by transverse walls 348c (shown in phantom in FIG. 23A). As shown, e.g., in FIG. 23C, each set of two consecutive walls 348c that are disposed above the longitudinal lumen forms an upper channel 342 which extends from the longitudinal lumen towards the top edge 340c of the proximal flap 340a. Similarly, each set of two consecutive walls 348c that are disposed below the longitudinal hollow lumen forms a lower channel 343 which extends from the longitudinal lumen towards the bottom edge 340d of the proximal flap 340a. With this construction, the longitudinal hollow lumen itself is formed as an axial passageway having intermittent boundary sections that are defined by the ends of the transverse walls 348c that are closest to the longitudinal lumen. In this way, the channels 342, 343 provide a plurality of conduits for debris and fluid evacuation, thereby allowing for simultaneous aspiration of debris and fluid from top (palate of mouth) to bottom (floor of mouth), and through the passageway, during dental procedures.

It is again noted that, while, in the embodiment of FIGS. 23A-C, the tongue shield aspirator 340 is shown to include a plurality of upper channels and a plurality of lower channels, this is by way of illustration only. Thus, a tongue shield aspirator in accordance with embodiments of the invention may include one or more of each of the upper channel(s) 342 and lower channel(s) 343. In addition, the posterior and anterior layers 348a, 348b and the transverse walls 348c may be made of flexible material so as to enable proper placement of the tongue shield aspirator in the patient's mouth. Thus, each of the walls 348c is "transverse" in that it is generally perpendicular to the inner surfaces of the posterior and anterior layers 348a, 348b when the tongue shield aspirator is laid flat (i.e., as shown in the figures) but flexes along with these layers 348a, 348b when the tongue shield aspirator itself is flexed, e.g., for placement in the patient's mouth.

As discussed previously in connection with the embodiments of FIGS. 3 and 4, a tongue shield aspirator having the above-described construction may be considered an "open" tongue shield in the sense that the upper and lower edges of the tongue shield are open to, or in communication with, the patient's oral cavity. Thus, with reference to FIGS. 23A-C, each upper channel 342 extends towards the open top edge 340c of the proximal flap 340a, wherein the top edge 340c is formed by the respective top edges of the posterior layer 348a and the anterior layer 348b in the region of the proximal flap 340a. Similarly, each lower channel 343 extends towards the open bottom edge 340d of the proximal flap 340a, wherein the bottom edge 340d is formed by the respective bottom edges of the posterior layer 348a and the anterior layer 348b in the region of the proximal flap 340a. In this way, each of the top edge 340c and the bottom edge 340d of the proximal flap 340a is open along the entirety of the length thereof. In embodiments of the invention, the upper opening defined by the space between the top edges of the anterior and posterior layers, and the lower opening defined by the space between the bottom edges of the anterior and posterior layers may extend through the transition section 349 (as shown, e.g., in FIG. 23C), as well as at least a portion of the distal flap 340b.

FIG. 23C also shows a hollow neck 346 that is symmetrical with respect to the planes of the posterior and anterior layers 348a, 348b. Thus, in contrast to the embodiments shown in FIGS. 3 and 4, where the necks 46, 246 extend at an angle from the respective planes of the tongue shield aspirators 40, 240, the neck 346 of the tongue shield aspirator 340 shares the central axis of the longitudinal passageway defined therethrough. Thus, the passageway extends from a distal end 346b, through the proximal flap 340a, and through the proximal end 346a of the neck 346. As such, the proximal end of the passageway coincides with the proximal end of the hollow neck. In embodiments of the invention, the distal end 346b of the passageway may be located at a point along a longitudinal portion of the proximal flap 340a, the transition section 349, or the distal flap 340b.

With reference to FIGS. 18-20, the neck 346 is configured to be matingly received through the distal end 312a of the bite member's conduit 312. In this regard, on its posterior side, the neck 346 may include a longitudinal projection 344 that mates with a groove 311 defined within a wall of the conduit 312. Specifically, as shown, e.g., in FIGS. 20A and 20D, the groove 311 starts from the distal end 312a and extends longitudinally through a portion of the conduit 312. Thus, when assembling the device 300, the projection 344 aids in correctly orienting the tongue shield aspirator 340 with respect to the bite member 310. In addition, when assembled, the combination of the projection 344 and the groove 311 prevents rotation of the tongue shield aspirator 340. As such, in embodiments of the invention, the tongue shield aspirator mates with the bite member in a non-rotational, as well as a non-pivotable, manner.

Referring back to FIGS. 23A-C, in embodiments of the invention, one or both of the flaps 340a, 340b may include finger-like projections 345 on the bottom and/or top edge thereof, thereby creating a "one-size-fits-all" feature and providing a comfortable form-fitting seal within the patient's mouth. Thus, in the embodiment shown, each of the posterior and anterior layers includes projections 345 on each of its top and bottom edges in the region of the proximal flap 340a, with the posterior layer having a profile that extends beyond the profile of the anterior layer, i.e., the top and bottom edges of the posterior layer extend beyond the respective top and bottom edges of the anterior layer. Moreover, the tongue shield aspirator 340 may include a longitudinal stiffener 347 on the anterior layer 348b to prevent kinking when the tongue shield aspirator is flexed and/or bent for placement within the patient's oral cavity.

It is also noted that the first end 332 of the evacuation tube 330 is configured to fit within the hollow neck 346 of the tongue shield aspirator 340. Thus, when assembled, the tongue shield aspirator's neck receives therein the first end 332 of the evacuation tube so as to form a friction fit within the bite member's conduit 312, thereby decreasing the likelihood of leakage and improving stability of the assembled device. In connection with the assembled device, as mentioned previously, offsetting of the conduit—and, therefore, of the distal end 312a thereof—at an oblique angle decreases resistance to airflow through the tongue shield aspirator-bite member combination. This goal is also furthered by the symmetrical, rather than angled, placement of the neck 346 with respect to the planes of the posterior and anterior layers 348a, 348b.

FIGS. 24A-D show a tongue shield aspirator 440 in accordance with an alternative embodiment of the invention. As shown in the Figures, the tongue shield aspirator 440 is substantially similar to the tongue shield aspirator 340 discussed immediately above. Thus, tongue shield aspirator 440 is an open component having a first (proximal) flap 440a, which is configured to retract a patient's tongue, a transition section 449, a second (distal) flap 440b, which is configured to retract a patient's cheek, and a longitudinal passageway 441 that is in fluid communication with one or more channels that may extend at an angle from the passageway.

Figure 24A:
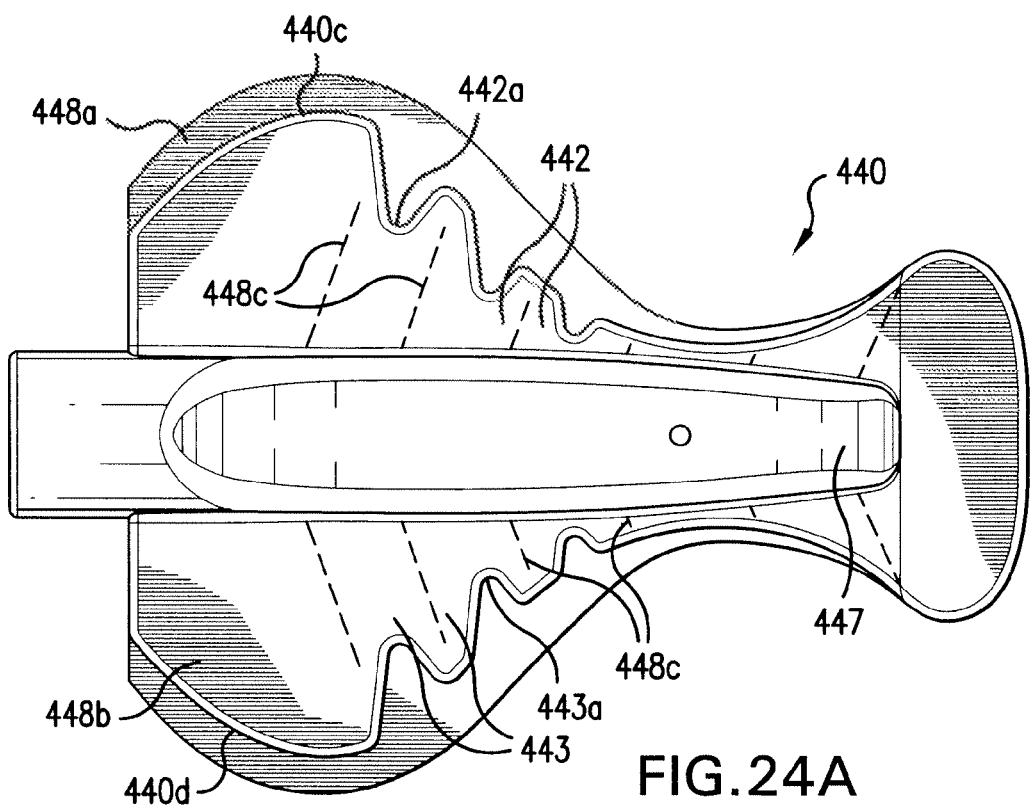
FIG. 24A is an anterior view of a tongue shield aspirator in accordance with another embodiment of the invention.
Figure 24B:
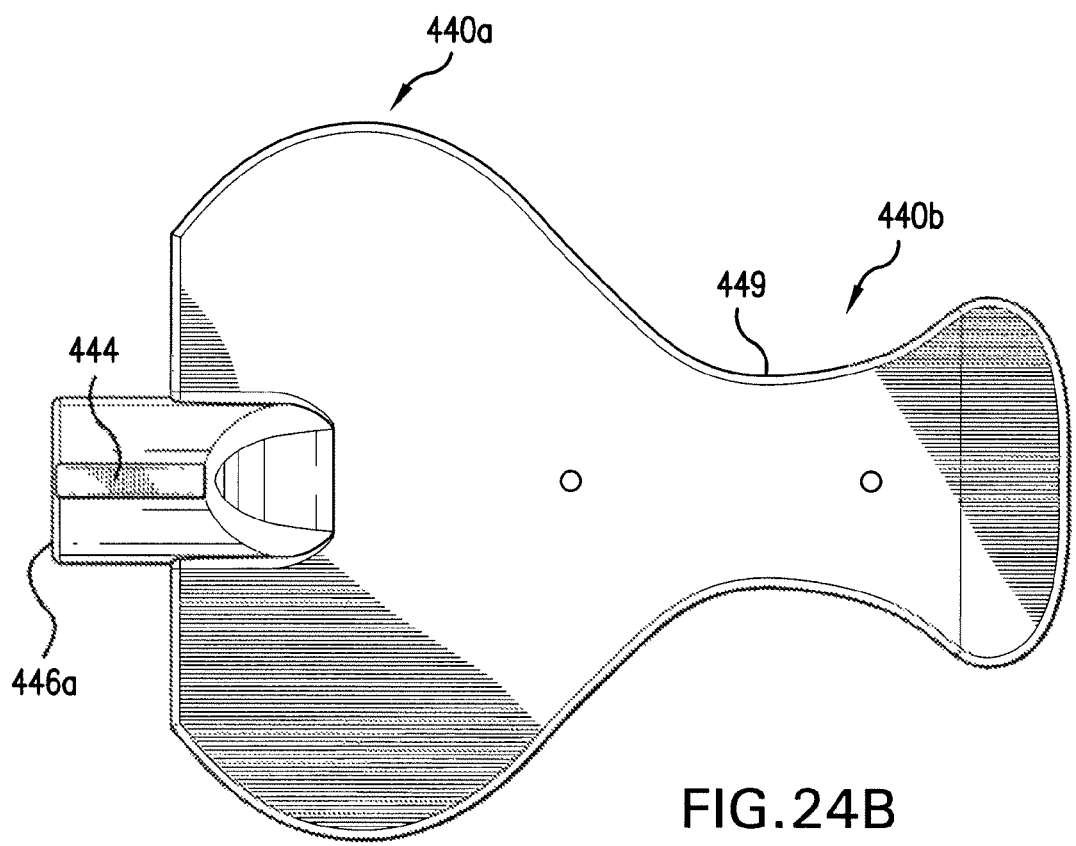
FIG. 24B is a posterior view of the tongue shield aspirator shown in FIG. 24A.
Figure 24C:
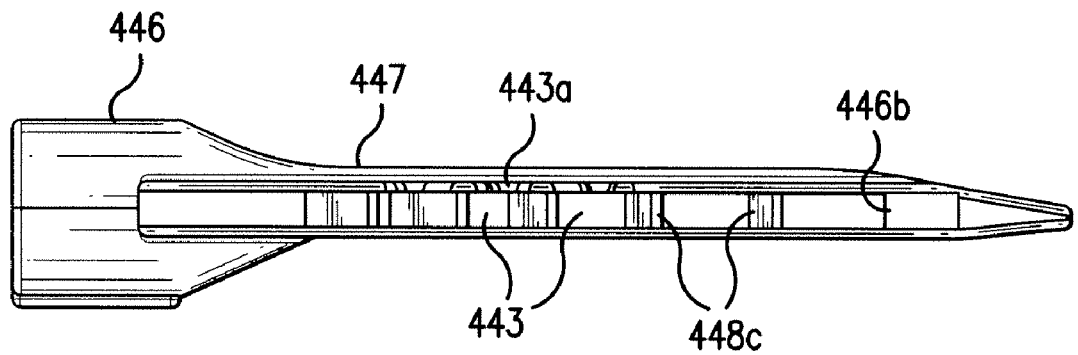
FIG. 24C is a bottom side view of the tongue shield aspirator shown in FIG. 24A.
Figure 24D:
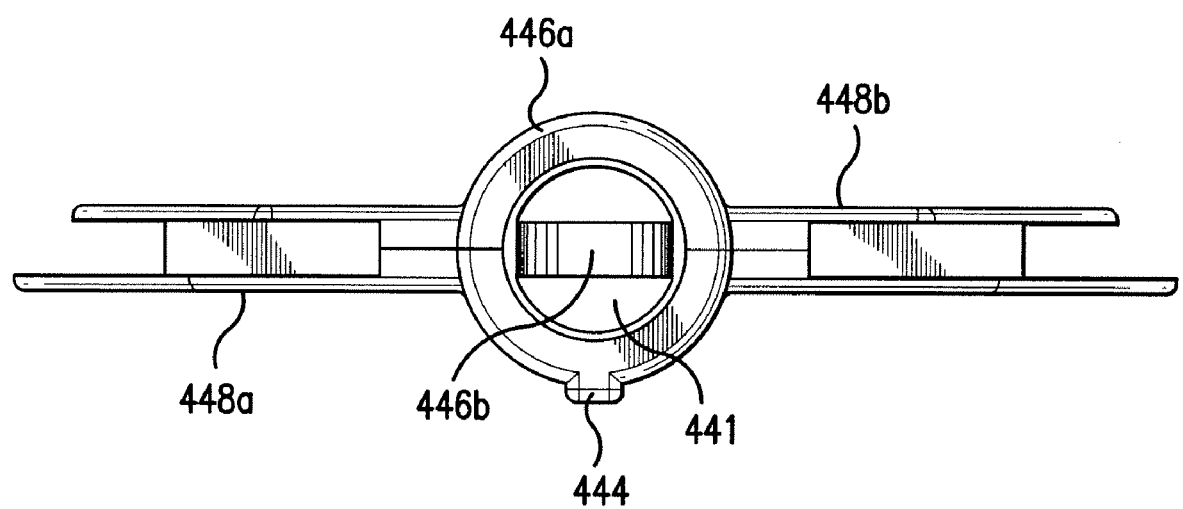
FIG. 24D is a back-end view of the tongue shield aspirator shown in FIG. 24A.

The proximal flap 440a and/or the distal flap 440b of the tongue shield aspirator 440 may be formed from a first (posterior) layer 448a and a second (anterior) layer 448b which are connected to, but spaced apart from, one another by walls 448c (shown in phantom in FIG. 24A). As shown, e.g., in FIGS. 24A and 24C, each set of two consecutive walls 448c that are disposed above the passageway forms an upper channel 442 which extends from the passageway towards the top edge 440c of the proximal flap 440a. Similarly, each set of two consecutive walls 448c that are disposed below the longitudinal hollow lumen forms a lower channel 443 which extends from the longitudinal lumen towards the bottom edge 440d of the proximal flap 440a.

The tongue shield aspirator 440 also includes a hollow neck 446 that is symmetrical with respect to the planes of the posterior and anterior layers 448a, 448b, such that the passageway 441 extends from a distal end 446b, through the proximal flap 440a, and through the proximal end 446a of the neck 446. As such, the proximal end of the passageway coincides with the proximal end of the hollow neck. In embodiments of the invention, the distal end 446b of the passageway may be located at a point along a longitudinal portion of the proximal flap 440a, the transition section 449, or the distal flap 440b.

The hollow neck 446 is configured to receive therein the first end 332 of the evacuation tube 310 so as to form a friction fit within the bite member's conduit 312. In addition, on its posterior side, the neck 446 may include a longitudinal projection 444 that mates with the groove 311. The tongue shield aspirator 440 may also include a longitudinal stiffener 447 on the anterior layer 448b to prevent kinking when the tongue shield aspirator is flexed and/or bent for placement within the patient's oral cavity.

As with the embodiment shown in FIG. 23, the posterior layer 448a may have a profile that extends beyond the profile of the anterior layer 448b, i.e., the top and bottom edges of the posterior layer extend beyond the respective top and bottom edges of the anterior layer. However, in contrast with the tongue shield aspirator 340, the tongue shield aspirator 440 has no projections (i.e., similar to projections 345) on the posterior layer 448a, and the anterior layer 448b now includes a cut-out pattern along at least a portion of each of its top and bottom edges in the region of the proximal flap 440a. Specifically, with reference to FIG. 24A, each upper channel 442 has a lower end that is in direct fluid communication with the passageway 441, and an upper end towards the top edge of the anterior layer 448b. Similarly, each lower channel 443 has an upper end that is in direct fluid communication with the passageway 441, and a lower end towards the lower edge of the anterior layer 448b. In turn, the top edge of the anterior layer 448b includes an indentation 442a proximate the upper end of one or more of the upper channel(s) 442, and the bottom edge of the anterior layer 448b includes an indentation 443a proximate the lower end of one or more of the lower channel(s) 443.

Thus, in the illustrative embodiment shown in FIG. 24A, there are three such indentations 442a, 442b on each of the top and bottom edges of the anterior layer 448b in the region of the proximal flap 440a. Together, the three top indentations 442a comprise a top cut-out pattern, and the three bottom indentations 443a comprise a bottom cut-out pattern, each of which aids in enhancing debris and fluid aspiration from the patient's oral cavity. It is noted that, in embodiments of the invention, each of the top and bottom edges of the anterior layer 448b may include one or more such indentations, which indentations may be disposed further (distally) along the tongue shield, e.g., in and/or around the transition section 449.

Figure 25A:
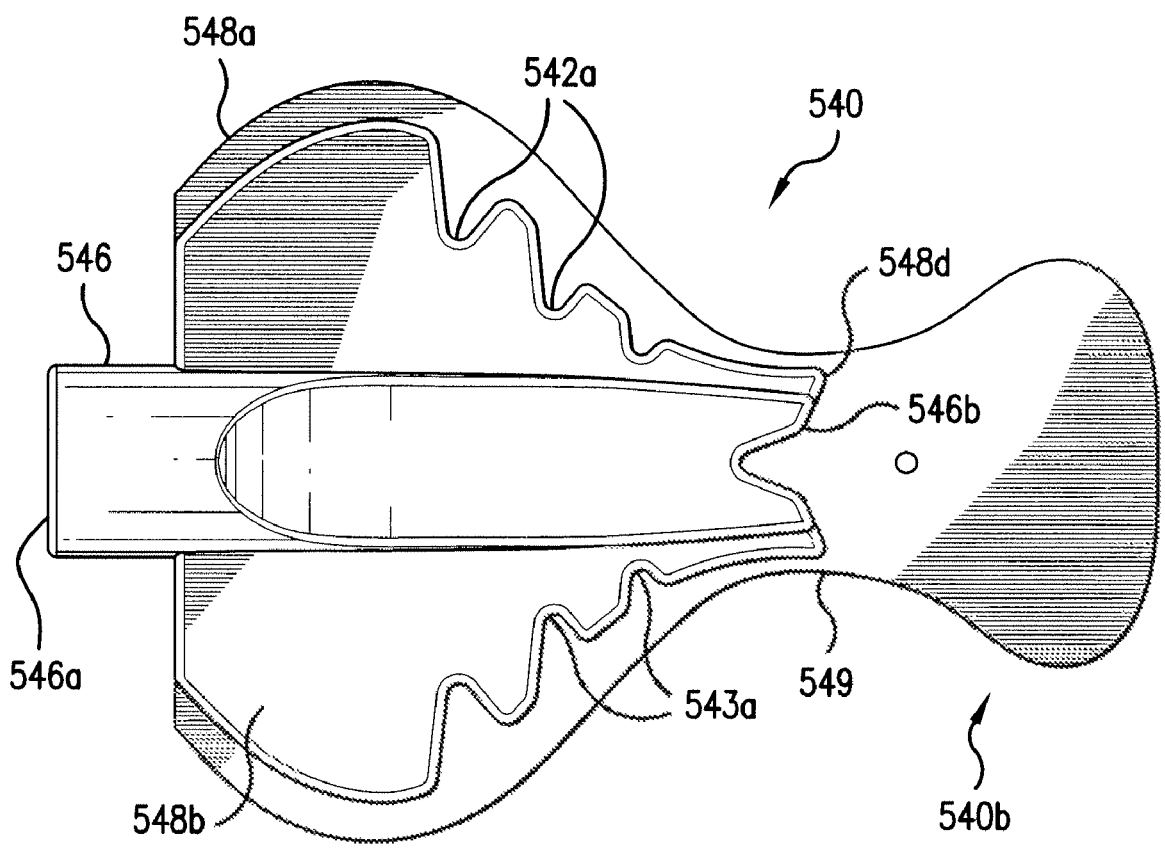
FIG. 25A is an anterior view of a tongue shield aspirator in accordance with another embodiment of the invention.
Figure 25B:
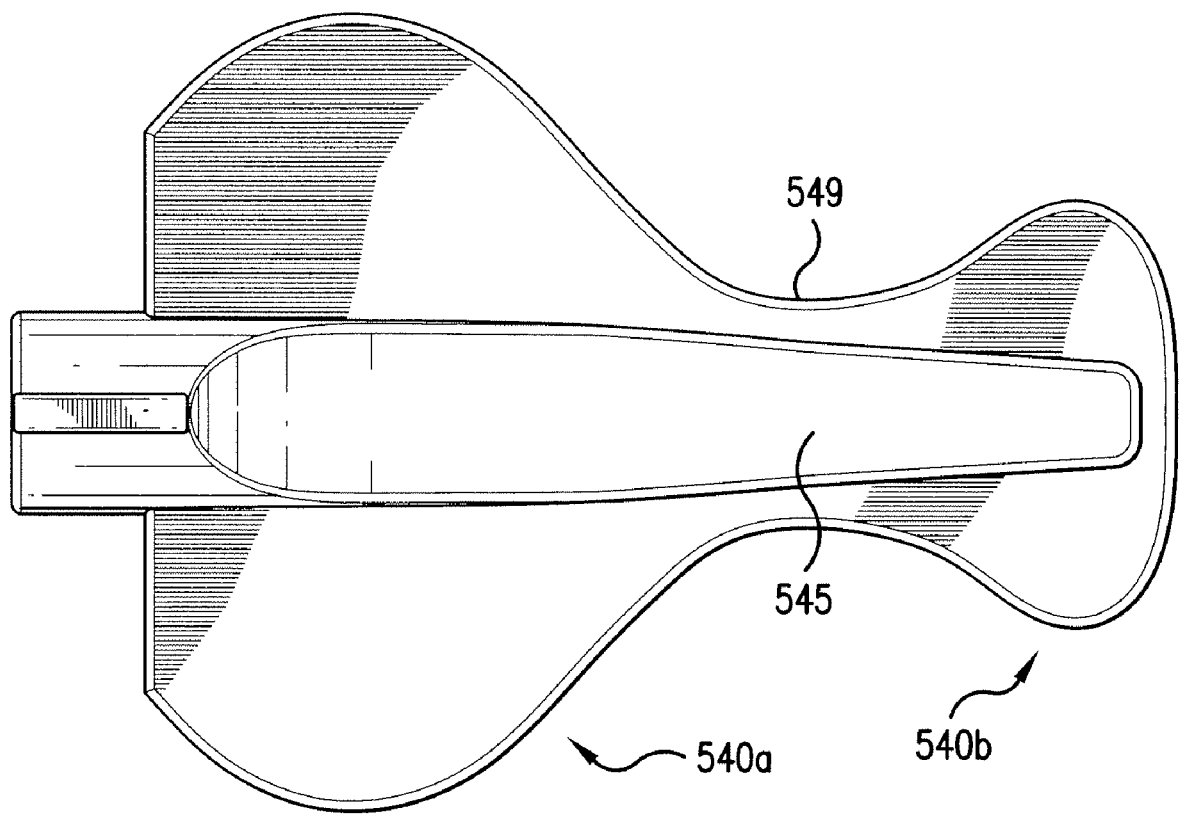
FIG. 25B is a posterior view of the tongue shield aspirator shown in FIG. 25A.
Figure 25C:
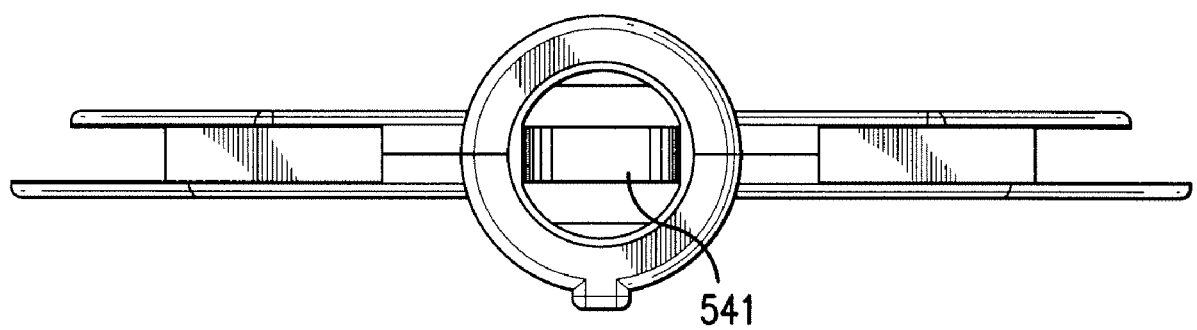
FIG. 25C is a back-end view of the tongue shield aspirator shown in FIG. 25A.
Figure 25D:
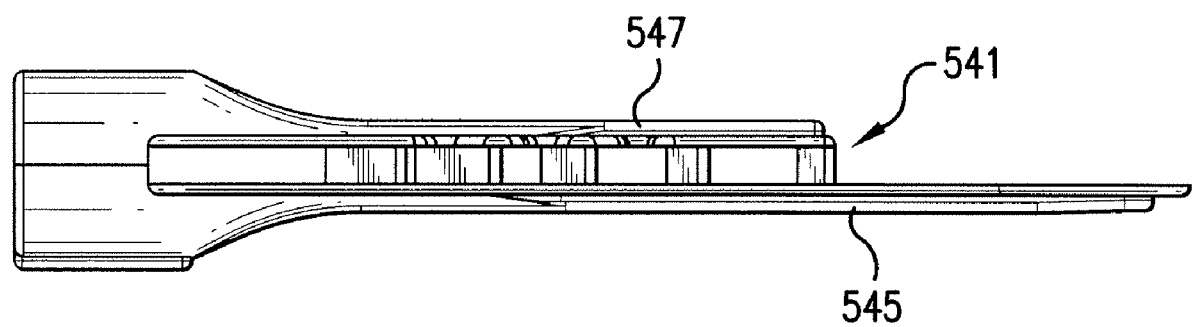
FIG. 25D is a bottom side view of the tongue shield aspirator shown in FIG. 25A.

FIGS. 25A-D show an open tongue shield aspirator 540 in accordance with an alternative embodiment of the invention. As shown in the figures, the tongue shield aspirator 540 is substantially similar to the tongue shield aspirator 440 discussed immediately above, except for the following differences. First, as shown in FIGS. 25A and 25D, the anterior layer 548b does not extend as far distally as the posterior layer 548a. Rather, in this embodiment, the anterior layer 548b is longitudinally shorter than the posterior layer 548a, such that the distal edge 548d of the anterior layer 548b is located proximally to the distal edge of the posterior layer 548a (i.e., located proximally to the distal edge of the distal flap 540b).

The tongue shield aspirator 540 also includes a hollow neck 546 that is symmetrical with respect to the planes of the posterior and anterior layers 548a, 548b, such that the passageway 541 extends from a distal end 546b, through the proximal flap 540a, and through the proximal end 546a of the neck 546. As such, the proximal end of the passageway coincides with the proximal end 546a of the hollow neck, and the distal end 546b of the passageway coincides with the distal end 548d of the anterior layer 548b. Thus, in the embodiment shown in FIGS. 25A-25D, the tongue shield aspirator 540 is open in the sense that, in addition to the upper and lower edges of the tongue shield, the distal end of the passageway is also open to, or in communication with, the patient's oral cavity. This provides various advantages, including enhanced fluid and debris aspiration, as well as facilitated bending at or around the transition section 549.

Second, in addition to the anterior longitudinal stiffener 547, the tongue shield aspirator 540 may also include a posterior longitudinal stiffener 545 on the back (i.e., posterior) side of the posterior layer 548a for added support, e.g., when the tongue shield aspirator is flexed and/or bent for placement within the patient's oral cavity. In the embodiment of FIG. 25, the anterior stiffener 547 is integral with the neck 546, and has a distal end that coincides with the distal end of the anterior layer 548b. The posterior stiffener 545 is also integral with (a posterior side of) the neck 546, but extends longitudinally past the transition section 549, as shown in FIG. 25B.

As mentioned, the tongue shield aspirator 540 is substantially similar to the tongue shield aspirator 440. Thus, for example, the tongue shield aspirator 540 may include one or more top indentations 542a and one or more bottom indentations 543a. In addition, as shown in FIG. 25A, the distal edge 548d of the anterior layer 548b and/or the distal edge of the anterior stiffener 547 may include a longitudinal indentation to further enhance debris and fluid aspiration from the patient's oral cavity.

Figure 25E:
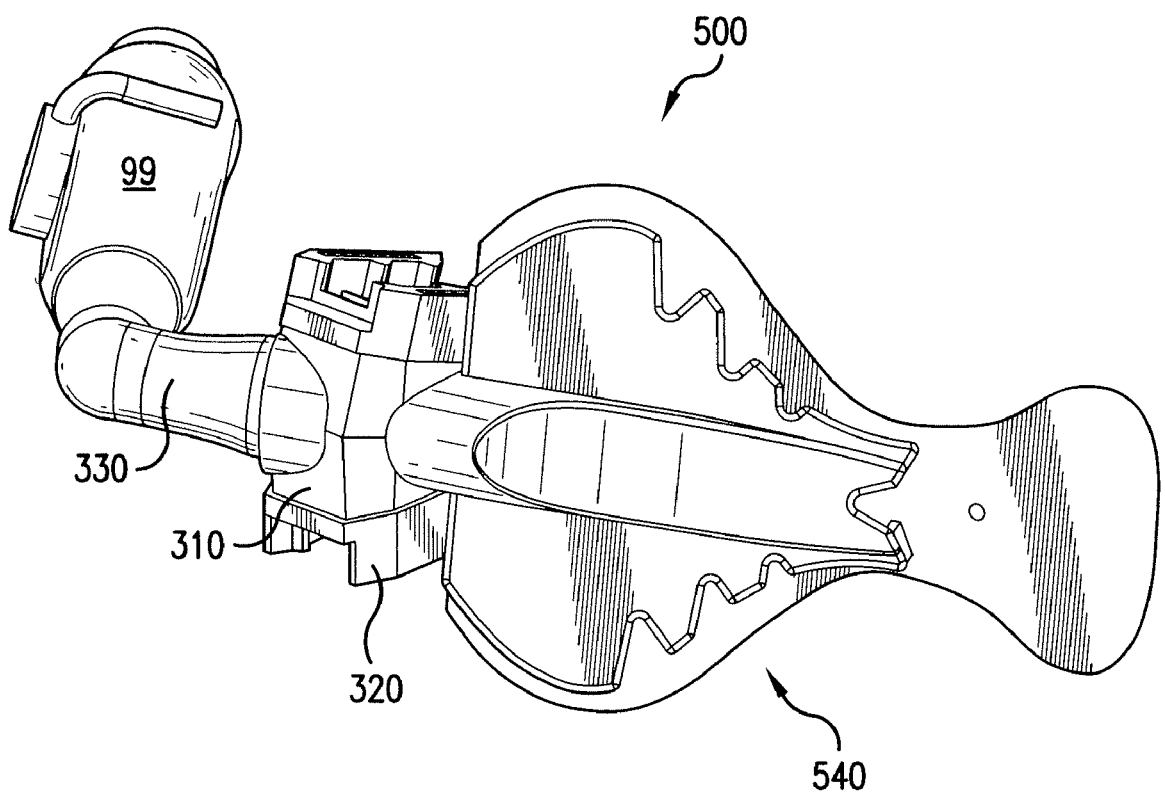
FIG. 25E is a perspective view of an assembled intra-oral device in accordance with an embodiment of the invention.

FIG. 25E shows an intra-oral device 500 in accordance with this embodiment of the invention. As shown, in addition to the tongue shield aspirator 540, the device 500 includes the same overall components that were discussed above in connection with FIG. 18, namely, a bite member 310, a bite grip 320, and an evacuation tube 330 that, at one end, is attached to a HVE valve 99.

Figure 26A:
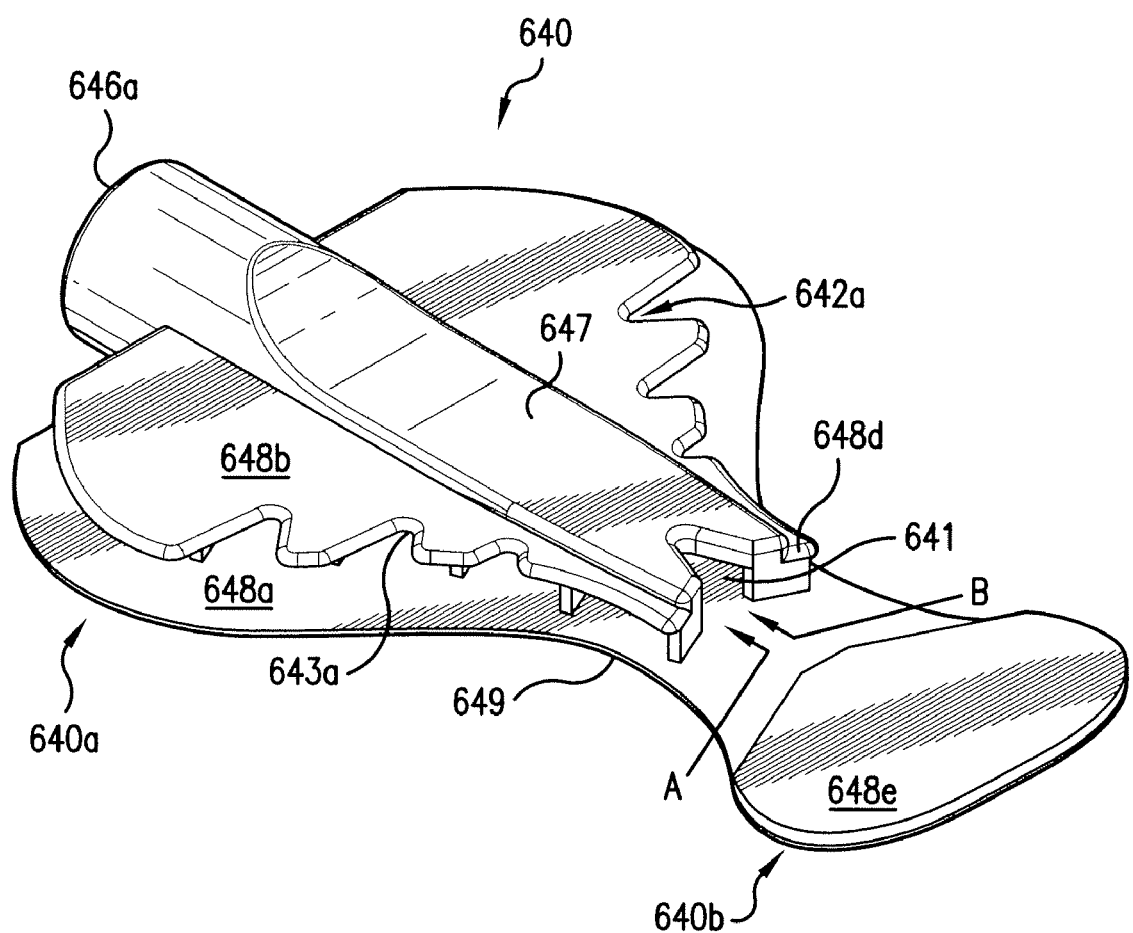
FIG. 26A is a perspective view of a tongue shield aspirator in accordance with another embodiment of the invention.
Figure 26B:
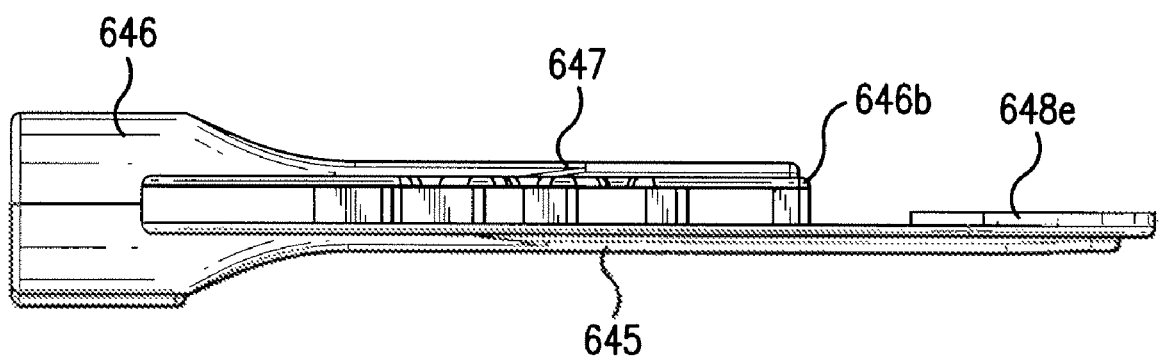
FIG. 26B is a bottom side view of the tongue shield aspirator shown in FIG. 26A.

FIGS. 26A-26B show an open tongue shield aspirator 640 in accordance with an alternative embodiment of the invention. As shown in the figures, the tongue shield aspirator 640 is substantially similar to the tongue shield aspirator 540 discussed above, except that the tongue shield aspirator 640 now includes a raised portion 648e on the distal flap 640b. Thus, as in FIGS. 25A and 25D, the anterior layer 648b is longitudinally shorter than the posterior layer 648a, such that the distal edge 648d of the anterior layer 648b is located proximally to the distal edge of the posterior layer 648a (i.e., located proximally to the distal edge of the distal flap 640b). The tongue shield aspirator 640 also includes a hollow neck 646 that is symmetrical with respect to the planes of the posterior and anterior layers 648a, 648b, such that the passageway 641 extends from a distal end 646b, through the proximal flap 640a, and through the proximal end 646a of the neck 646. As such, the proximal end of the passageway coincides with the proximal end 646a of the hollow neck, and the distal end 646b of the passageway coincides with the distal end 648d of the anterior layer 648b. Thus, the tongue shield aspirator 640 is open to, or in communication with, the patient's oral cavity through the distal end of the passageway as well as the upper and lower edges of the tongue shield.

Also, in addition to the anterior longitudinal stiffener 647, the tongue shield aspirator 640 may also include a posterior longitudinal stiffener 645 on the back (i.e., posterior) side of the posterior layer 648a for added support. As before, the anterior stiffener 647 may be integral with the neck 646, and has a distal end that coincides with the distal end of the anterior layer 648b. The posterior stiffener 645 may also be integral with (a posterior side of) the neck 646, and may extend longitudinally past the transition section 649.

Moreover, the tongue shield aspirator 640 may include one or more top indentations 642a and one or more bottom indentations 643a. In addition, the distal edge 648d of the anterior layer 648b and/or the distal edge of the anterior stiffener 647 may include a longitudinal indentation to further enhance debris and fluid aspiration from the patient's oral cavity.

As shown in FIGS. 26A-26B, however, on its anterior side, the posterior layer 648a includes a raised portion 648e that, distally, may abut the distal end of the distal flap 640b. Proximally, however, the raised portion 648e may be shaped so as to guide fluid and debris towards the distal end 646b of the passageway 641. Thus, in the exemplary embodiment shown in FIG. 26A, the proximal side of the raised portion 646e is shaped like a truncated triangle, such that, when placed in a patient's oral cavity, fluid and/or debris from a top side of the cavity is directed towards the passageway 641 along the Arrow "B", while fluid and/or debris from a bottom side of the cavity is directed towards the passageway 641 along the Arrow "A". As noted, however, other shapes and configurations may also be used, so long as the proximal side of the raised portion 648e helps guide fluid/debris towards the passageway 641.

It is noted that, in embodiments of the invention, such as those shown, e.g., in FIGS. 23-24, the anterior stiffener (e.g., stiffener 347) may extend distally from the anterior side of the hollow neck. In other embodiments, however, the stiffener may be physically separate from the neck, may be comprised of a series of spaced-apart, smaller stiffeners, and/or may be disposed on the anterior layer at various points along the longitudinal axis of the tongue shield aspirator. Similarly, in FIGS. 25-26, e.g., the posterior stiffener (e.g., the stiffener 545) is shown to extend distally from the posterior side of the hollow neck. In other embodiments, however, the posterior stiffener may be physically separate from the neck, may be comprised of a series of spaced-apart, smaller stiffeners, and/or may be disposed on the posterior layer at various points along the longitudinal axis of the tongue shield aspirator.

Figure 27A:
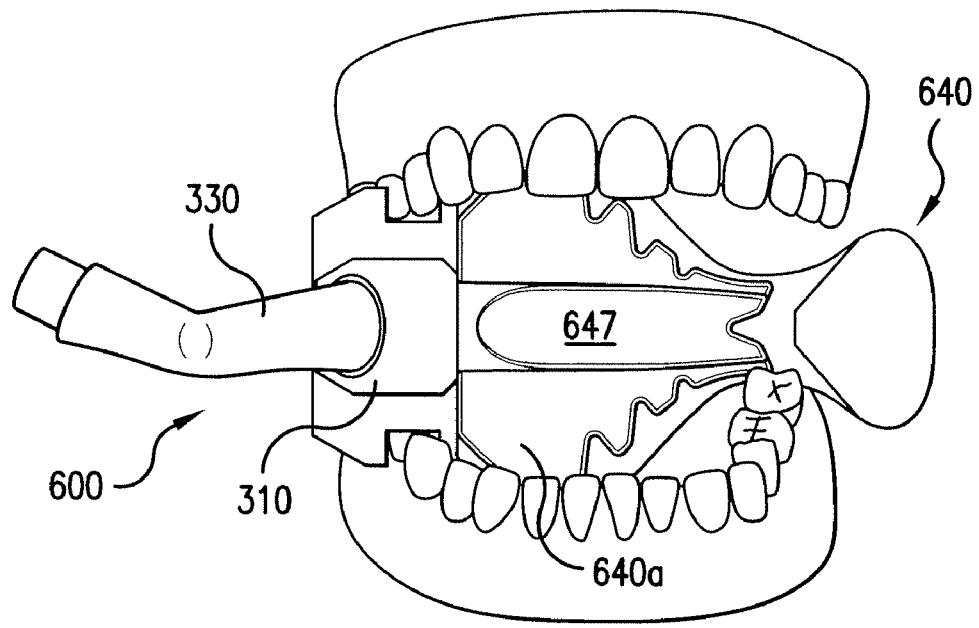
FIG. 27A is an anterior view of an intra-oral device held between a patient's upper and lower teeth.
Figure 27B:
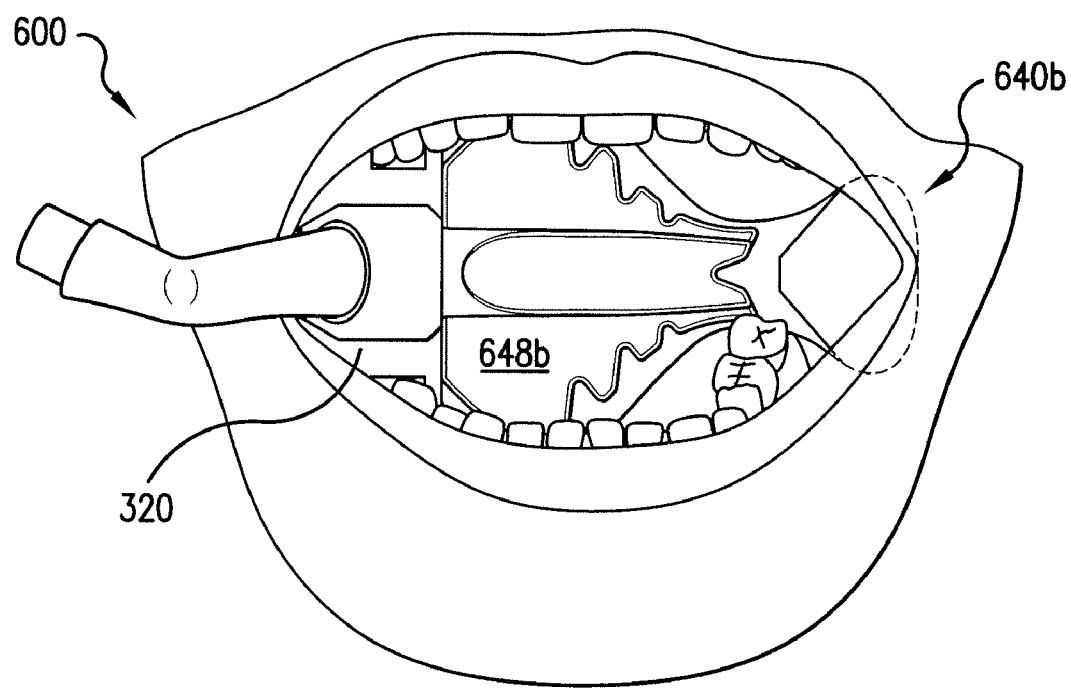
FIG. 27B shows the intra-oral device of FIG. 27A inside the patient's mouth, with the patient's cheek retracted.

FIGS. 27A and 27B show an intra-oral device 600 after placement within a patient's mouth. Specifically, FIG. 27A shows the placement of the device 600 and, more particularly, of the bite member-bite grip 310, 320 combination between the patient's upper and lower jaws without showing the patient's mouth or cheeks. FIG. 27B shows the latter and, as such, shows the distal portion of the distal flap 640b in phantom, as this portion is bent within the mouth so as to retract the patient's cheek. It is noted that, while FIGS. 27A and 27B, as well as the ensuing discussion in connection with methodology, are directed to the intra-oral device 600 and its constituent components, this is for illustrative purposes only, and the discussion may be equally applicable to one or more of the other intra-oral devices and/or components described herein.

As has been noted previously, the intra-oral device 600 may be assembled by attaching an unused bite grip 320 to a sterilized bite member 310. The autoclavable components of the device, such as, e.g., the bite member 310 and the evacuation tube 330 may be sterilized in steam autoclave at a (max) temperature of 134° C. Next, an unused tongue shield 640 is inserted into the distal end 312a of the conduit 312 of the bite member, such that the proximal edges of the posterior and anterior layers 648a, 648b are flush with the distal side 315 of the bite member 310 (see, e.g., FIG. 20). A sterilized evacuation tube 330 is then inserted into the proximal end 312b of the conduit 312, ensuring that the evacuation tube is rotated so as to be in its most anterior or forward position and such that the protrusions 313 are aligned with the indentations 335 of the evacuation tube 330. As the evacuation tube is inserted into the bite member, its distal end is configured to insert into the hollow neck 646 of the tongue shield 640 within the conduit 312. The evacuation tube 330 is then rotated to lock it in place. Finally, the proximal end of the evacuation tube is inserted directly into a HVE valve 99 (see, e.g., FIG. 25E).

Once assembled, the intra-oral device 600 may be inserted into the patient's oral cavity. Prior to doing so, however, water may be sprayed on the posterior side of the tongue shield aspirator (i.e., the side that will be in contact with the patient's tongue so as to retract it) to lubricate it. To insert the intra-oral device, the bite member-bite grip combination is positioned toward the center of the patient's mouth, and then gently inserted and moved towards a lateral position—which may, e.g., be performed with a curling, or rotating motion—within the cavity, preferably in one smooth motion. Thus, in the illustrative example shown in FIG. 27, the bite member-bite grip combination is first positioned (outside the mouth) towards the center of the mouth. With the proximal side (i.e., the left side looking at the diagrams in FIGS. 27A and 27B) of the device held with one hand, the operator then gently bends the distal side, such that the distal flap 640b curls outwards from the plane of the page in FIG. 27.

With the patient's mouth open, the bite member-bite grip combination is then inserted into the mouth and moved towards the left of the diagrams in FIG. 27, until it reaches the space between the upper and lower teeth. After the bite member-bite grip combination has been inserted into the mouth, and as it begins to be moved to a lateral position within the mouth, the rest of the device—i.e., the proximal flap, the transition section, etc., of tongue shield aspirator—follows, such that, by the time the bite member-bite grip combination is at the patient's teeth, the operator begins to release the bending pressure on the distal end of the tongue shield aspirator so as to enable it to become uncurled within the mouth.

In following the bite member-bite grip combination, as it enters the mouth, the tongue retractor portion (e.g., the proximal flap 640a) of the tongue shield aspirator folds as its top and bottom edges encounter the incisal edges of the anterior teeth, thereby gently pressing the tongue into a retracted position. The bite member-bite grip combination is now positioned behind the first mandibular bicuspid—on the right quadrant of the patient's mouth in FIG. 27—and the transition section is positioned distal to the last molar(s)—on the left quadrant of the patient's mouth in FIG. 27. The distal flap 640b is then released so as to uncurl and retract the patient's (left) cheek. With the device in position, the patient is then asked to close gently and so as to position the bite member-bite grip combination comfortably between maxillary and mandibular teeth of the mouth's left quadrant. With the HVE valve having been assembled, as described above, prior to insertion of the device, the valve may now be turned on so that treatment may be started.

It is noted that FIGS. 27A and 27B illustrate the positioning of the intra-oral device 600 in the mouth so as to prepare an obstruction-free operative space on the left side of the patient's mouth. For work to be performed on the right side of the patient's mouth, the same assembly and insertion procedures as those described above would be followed, expect that, here, the evacuation tube-HVE valve combination would be positioned to the right, and the distal flap 640b to the left, side of the diagram shown in FIG. 27 and, upon insertion into the oral cavity, the bite member-bite grip combination would be moved to the right side of the diagrams. No additional steps are required; as has been noted previously, the bite member is fully symmetrical, and the tongue shield aspirator is symmetrical about its longitudinal axis and, as such, configured for bilateral use in the mouth.

As has been discussed previously, any one or more of the tongue shield aspirators described in the present application may be adapted for manufacture in a variety of sizes, including adult and pediatric sizes. In addition, or in the alternative, any one or more of the tongue shield aspirators described in the present application may include a "one-size-fits-all" feature, whereby the periphery of the posterior layer and/or the anterior layer of the tongue shield aspirator may be trimmed for a more precise fit in the patient's mouth. In this regard, it is important to note that the shapes and sizes, including the relative sizes, of the posterior and anterior layers and the proximal and distal flaps are not limited to those described or shown. Rather, these elements may take on various shapes and/or sizes.

Figure 28A:
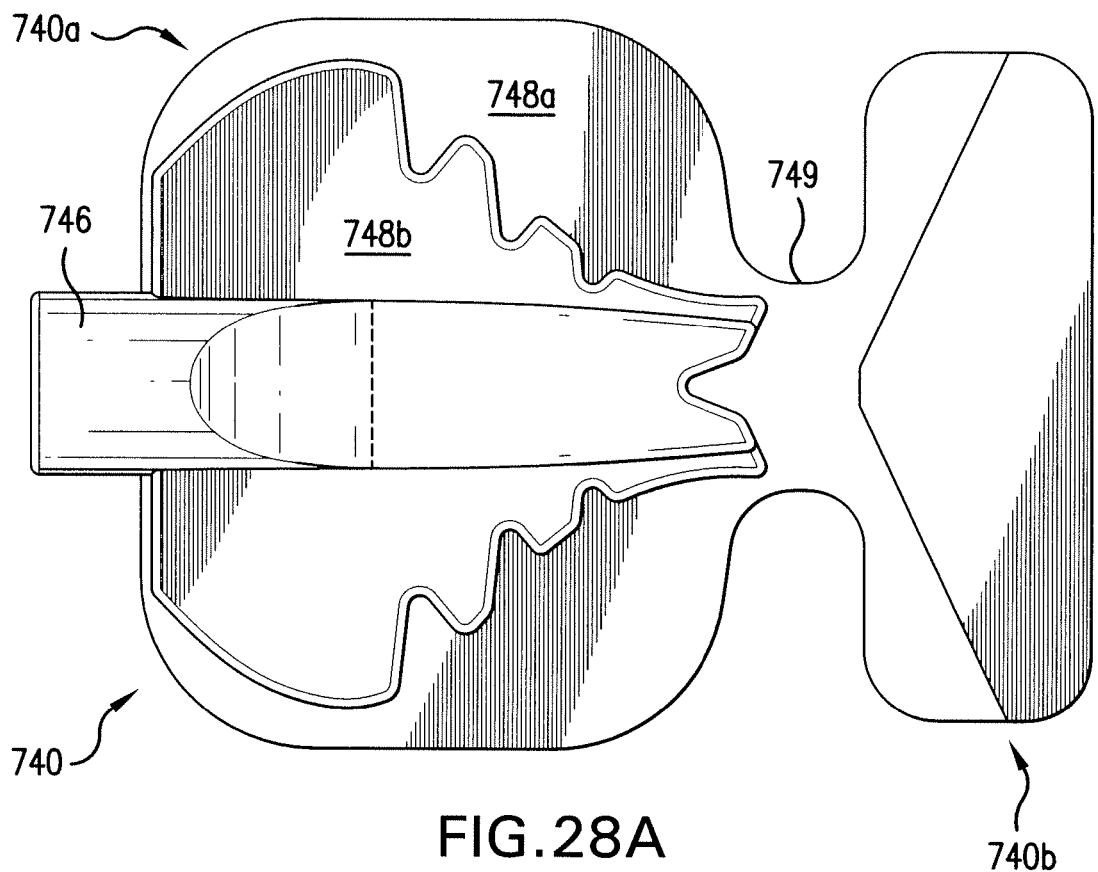
FIG. 28A is an anterior view of a tongue shield aspirator in accordance with another embodiment of the invention.
Figure 28B:
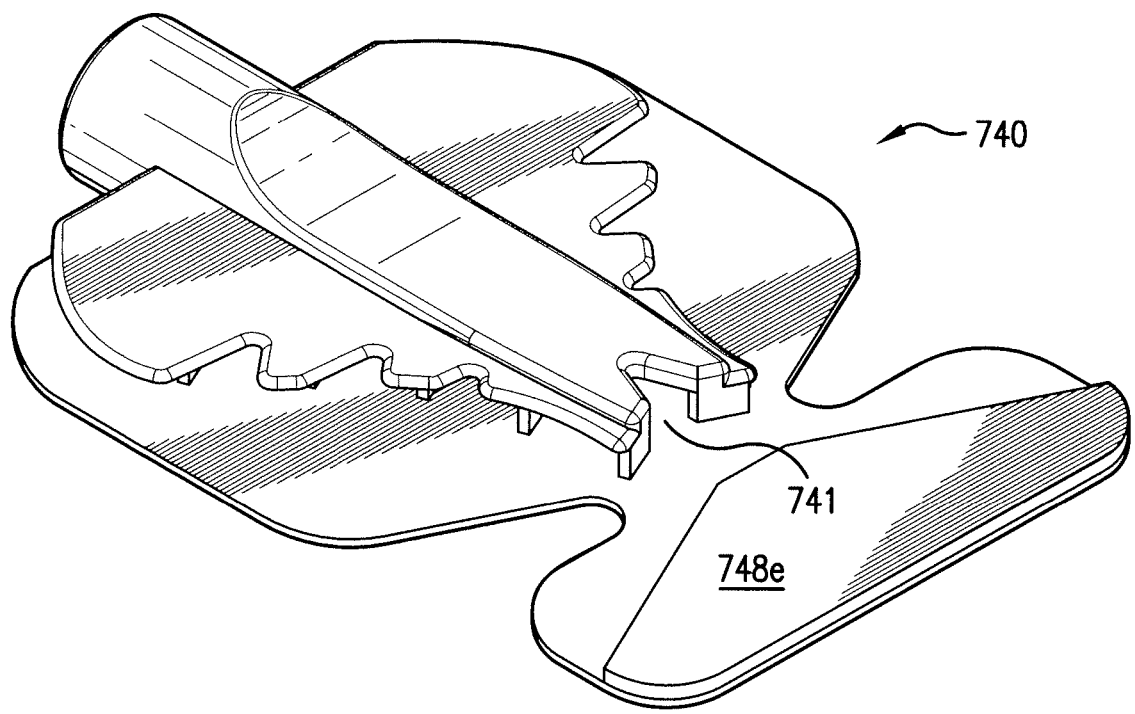
FIG. 28B is a top perspective view of the tongue shield aspirator shown in FIG. 28A.

Thus, for example, FIGS. 28A and 28B show a tongue shield aspirator 740 according to an embodiment of the invention, wherein the anterior layer 748b and neck 746 of the tongue shield aspirator 740 are identical to the anterior layer 648*b* and neck 646 of the tongue shield aspirator shown, e.g., in FIG. 26. However, the posterior layer 748*a* is now configured such that each of the proximal flap 740*a* and the distal flap 740*b* is larger in size, and of a quasi-rectangular, rather than simply an arcuate, shape. As in the embodiment shown in FIG. 26, the posterior layer 748*a* may also include a raised portion 748*e* on its distal flap 740*b* for helping direct debris and fluids toward the passageway 741. In embodiments of the invention, the proximal and distal flaps may take on various shapes and sizes.

Figure 29A:
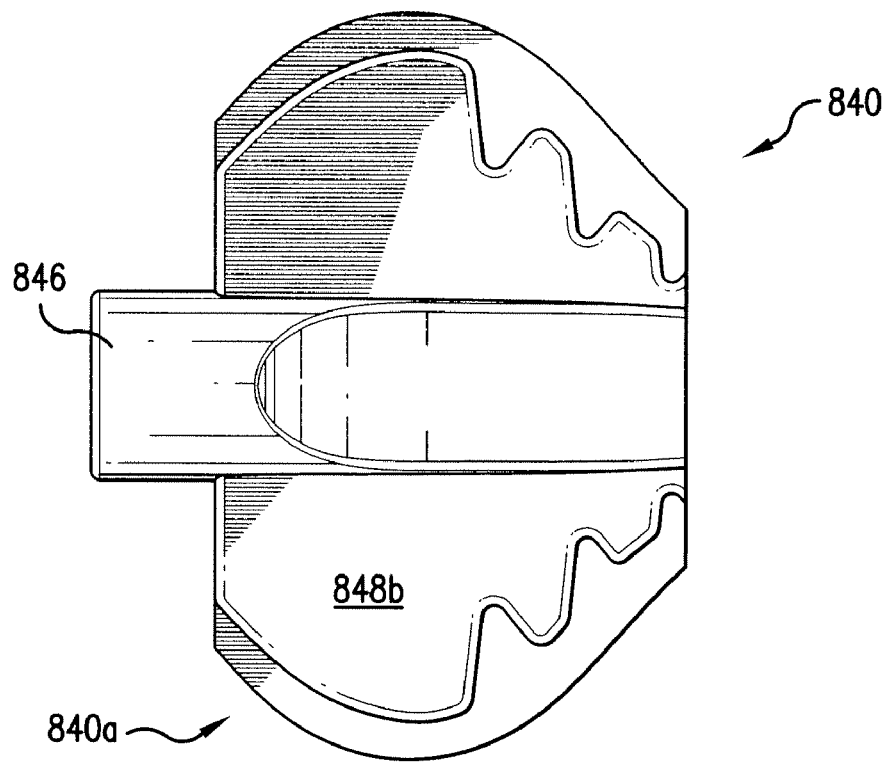
FIG. 29A is an anterior view of a tongue shield aspirator in accordance with another embodiment of the invention.
Figure 29B:
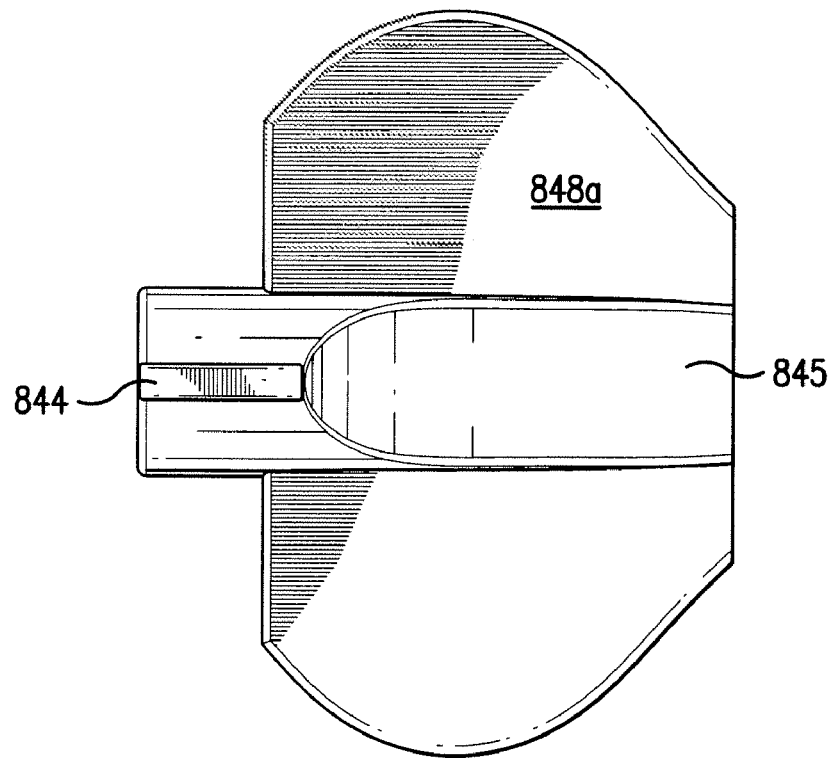
FIG. 29B is a posterior view of the tongue shield aspirator shown in FIG. 29A.
Figure 29C:
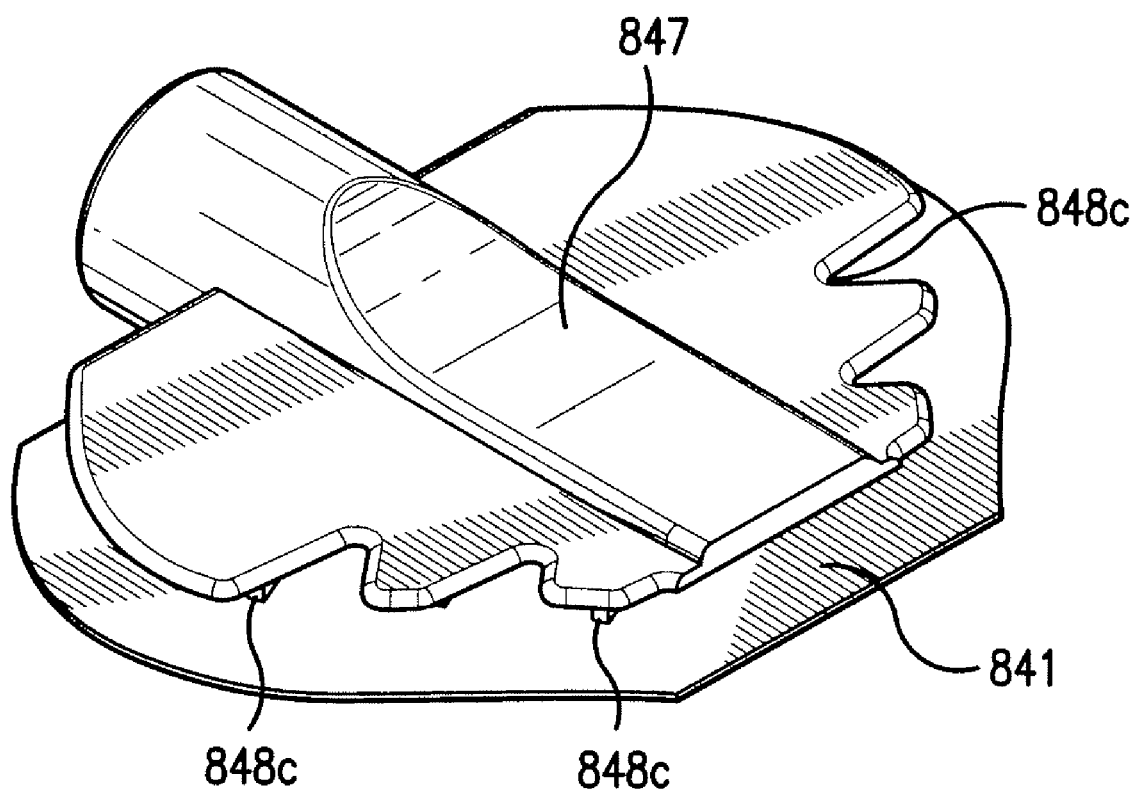
FIG. 29C is top perspective view of the tongue shield aspirator shown in FIG. 29A.

Similarly, in alternative embodiments, in addition to, or in place of, varying the shapes and/or relative sizes of the proximal and distal flaps, the above-mentioned "one-size-fits-all" feature enables not only peripheral trimming, but also shortening of the tongue shield aspirator by cutting along a line that is generally perpendicular to its the longitudinal axis and is positioned proximally to the tongue shield's distal end. Thus, for example, FIGS. 29A-29C show a the tongue shield aspirator 840 that has been trimmed, or cut, so as to include a proximal flap 840*a* only.

As shown, the tongue shield aspirator 840 includes all of the elements of, e.g., the tongue shield aspirator 640 shown in FIGS. 26 and 27, except that it has been cut proximally to the distal end of the anterior layer 648*b*. Thus, although the anterior layer 848*b* of the tongue shield aspirator 840 still includes a cut-out pattern along at least a portion of its top and bottom edges, it no longer includes a longitudinal indentation at its distal edge. The tongue shield aspirator 840 does, however, still include a hollow neck 846 which has a longitudinal projection 844 on its posterior side and is in fluid communication with the passageway 841, an anterior stiffener 847, a posterior stiffener 845, walls 848*c*, etc. It should be noted that the tongue shield aspirator may be trimmed along different points on its longitudinal axis. Thus, for example, the tongue shield aspirator may be cut at the distal end of the passageway, or at a point along the transition section, etc.

Figure 30A:
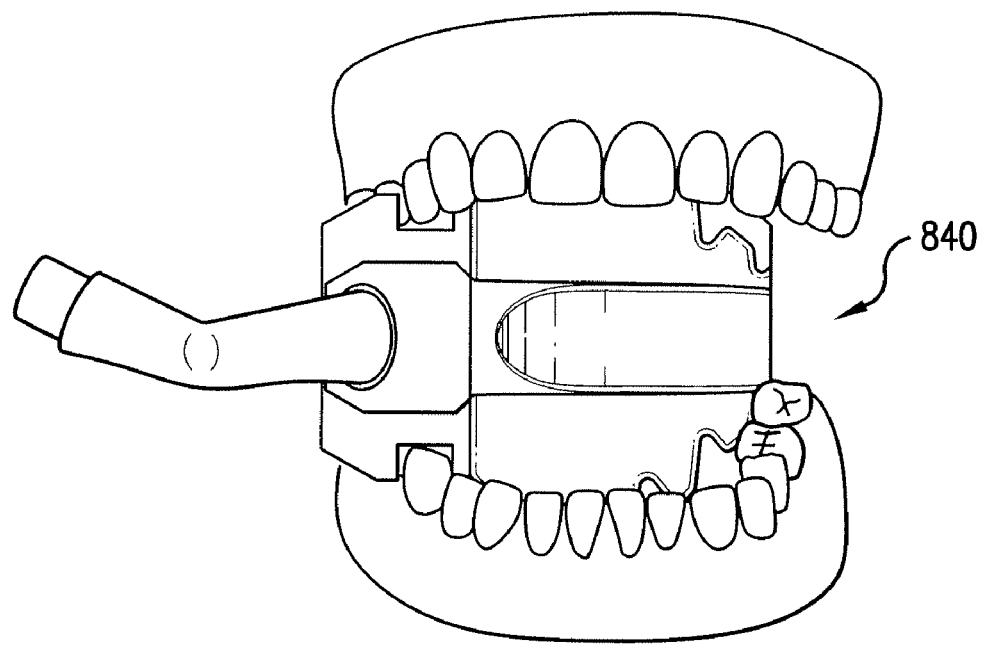
FIG. 30A is an anterior view of an intra-oral device held between a patient's upper and lower teeth.
Figure 30B:
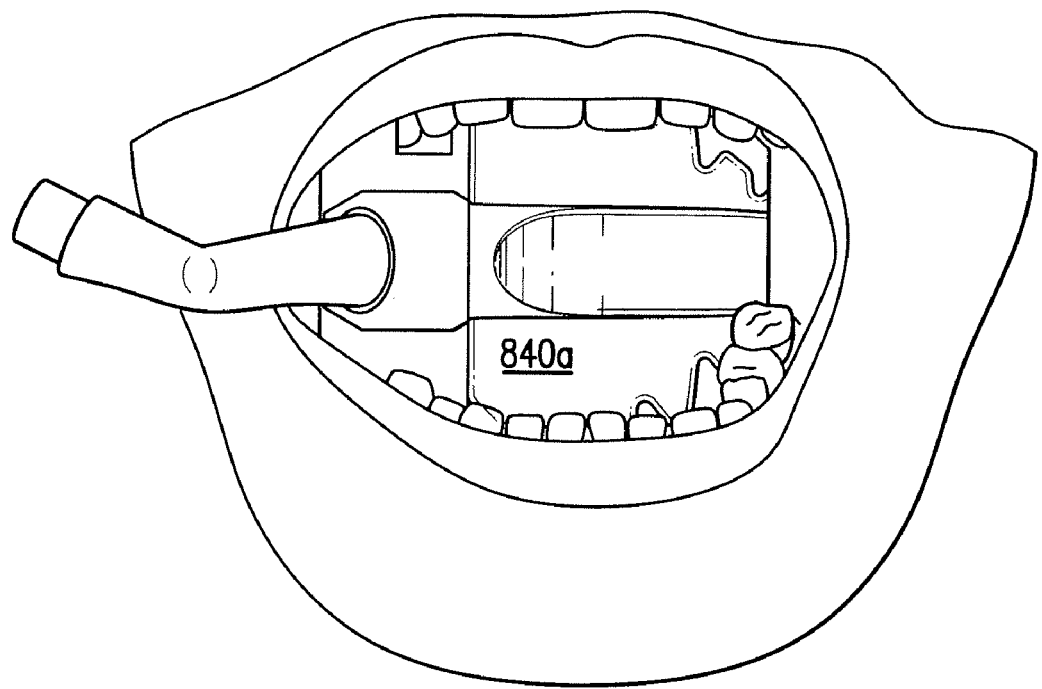
FIG. 30B shows the intra-oral device of FIG. 30A inside the patient's mouth.

FIGS. 30A and 30B show placement of the tongue shield aspirator 840 within a patient's mouth. As can be seen, this is substantially identical to the diagrams shown in FIGS. 27A and 27B, except that the tongue shield aspirator no longer includes a distal flap for retracting the patients' (left) cheek. As discussed in connection with FIG. 27, in order to prepare an operative space on the right side of the patient's mouth, the same assembly and insertion procedures as those described above would be followed, expect that, here, the evacuation tube-HVE valve combination would be positioned to the right, and the distal end of the proximal flap 840*a* to the left, side of the diagram shown in FIG. 30.

It is also important to note that one or more of the components discussed in the instant application may be adapted for use in conjunction with one or more of the other components described herein. Thus, for example, any one of the bite members discussed herein may be adapted for use with any one of the tongue shield devices discussed herein, and any one or more of the latter combination of components may be adapted for use with, e.g., any one of the evacuation tubes discussed herein, and so on. In addition, while a specific type of HVE valve 99 is described and shown in the diagrams, this is by way of illustration, and not limitation. As such, any standard-sized (e.g., ½-inch diameter) HVE may be used in conjunction with the components of the inventions described herein.

Also, as mentioned previously in connection with the tongue shield aspirator 40, although the flaps of the tongue shield aspirator of the various embodiments of the invention are described herein as being "joined" at a transition section (e.g., transition section 49), this is simply for ease of reference. In practice, any of the tongue shield aspirators described hereinabove may be manufactured as a unitary one-piece component, or the two flaps (e.g., flaps 40*a*, 40*b*) may be manufactured separately, and then joined to one another at the transition section.

While the description above refers to particular embodiments of the present invention, it will be understood that many modifications may be made without departing from the spirit and scope thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An intra-oral device comprising:
    a tongue shield aspirator including:
        a first layer configured to be in direct contact with, and retract, a patient's tongue;
        a second layer having the same length as the first layer and being spaced apart from the first layer by a plurality of walls so as to define between said layers a single axial passageway having a distal end that coincides with the respective distal edges of the first and second layers and is open so as to be in direct communication with the patient's oral cavity, said plurality of walls forming at least one upper channel extending from the passageway to a top edge of the second layer and at least one lower channel extending from the passageway to a bottom edge of the second layer so as to provide fluid communication between the passageway and the patient's oral cavity; and
        a hollow neck extending from the first and second layers opposite said respective distal edges and in fluid communication with said passageway, the passageway being straight through substantially the entire length thereof;
    a hollow evacuation tube configured to be coupled directly to a high-volume evacuation (HVE) valve; and
    a bite member defining a conduit that extends therethrough at an oblique angle, wherein, at a first end thereof configured to face the interior of the patient's oral cavity, the conduit is configured to detachably receive the neck of the tongue shield aspirator and, at a second end thereof configured to face the exterior of the patient's oral cavity, the conduit is configured to directly and detachably receive an end of the evacuation tube,
    wherein said top edge of the second layer is configured to face the patient's palate, and said distal edges of the first and second layers and the distal end of the passageway are configured to face away from the bite member.

2. The device of claim 1, further including a bite grip having an upper member configured to fit over a top side of the bite member and engageable by the patient's upper teeth and a lower member configured to fit over a bottom side of the bite member and engageable by the patient's lower teeth.

3. The device of claim 2, wherein the evacuation tube and the bite member are made of autoclavable resin, and the tongue shield aspirator and bite grip are made of a soft thermoplastic elastomer.

4. The device of claim 1, wherein the tongue shield aspirator is made of position-memory material.

5. The device of claim 1, wherein the top edge of the second layer includes an indentation proximate an upper end of the at least one upper channel, and the bottom edge of the second layer includes an indentation proximate a lower end of the at least one lower channel.

6. The device of claim 1, wherein the tongue shield aspirator mates with the bite member in a non-rotational, non-pivotable manner.

7. The device of claim 1, wherein a posterior side of the neck includes a longitudinal projection and the bite member's conduit includes a groove to matingly receive said projection so as to prevent rotation of the tongue shield aspirator.

8. The device of claim 1, wherein the evacuation tube is approximately L-shaped such that, when coupled to the bite member, it exits the patient's mouth at said oblique angle and then bends posteriorly at an angle of between about 85° and about 110°.

9. The device of claim 1, further including a locking mechanism to detachably secure the evacuation tube to the bite member.

10. The device of claim 1, said tongue shield aspirator being an open tongue shield aspirator.

11. The device of claim 1, wherein the tongue shield aspirator includes a longitudinal stiffener.

12. An intra-oral device comprising:
a tongue shield aspirator including:
a first layer having a posterior side configured to face a patient's throat, an opposite anterior side, a proximal edge, a distal edge, a bottom edge, and a top edge;
a second layer having a posterior side facing the first layer's anterior side, an anterior side configured to face away from the patient's throat, a proximal edge, a distal edge, a bottom edge, and a top edge, wherein the proximal edges of the first and second layers are substantially flush with each other, and the posterior side of the second layer is connected to the anterior side of the first layer by a plurality of walls such that the first and second layers are spaced apart from one another and define therebetween a single axial passageway, said passageway having a distal end that coincides with the respective distal edges of the first and second layers and is open so as to be directly exposed to the patient's oral cavity at said distal end; and
a hollow neck extending proximally from the proximal edges of the first and second layers and in fluid communication with said passageway, wherein the neck's proximal end constitutes the passageway's proximal end, said passageway being straight through substantially the entire length between the proximal and distal ends thereof;
a hollow evacuation tube having a first end, and a second end configured to be coupled directly to a high-volume evacuation (HVE) valve; and
a bite member configured to be disposed between the patient's upper and lower teeth and defining a conduit therethrough, wherein, at a first end of the conduit, the bite member is configured to detachably mate with the neck of the tongue shield aspirator and, at a second end of the conduit, the bite member is configured to directly and detachably mate with the first end of the evacuation tube, thereby providing fluid communication between the HVE valve and the patient's oral cavity via said evacuation tube, conduit, and passageway,
wherein said top edges of the first and second layers are configured to face the patient's palate, said proximal edges of the first and second layers are configured to face the bite member, and said distal edges of the first and second layers are configured to face away from the bite member.

13. The device of claim 12, wherein at least one of the bite member and the evacuation tube is made of autoclavable material.

14. The device of claim 13, wherein said autoclavable material is an amorphous thermoplastic polyetherimide.

15. The device of claim 12, said plurality of walls including two walls disposed above the axial passageway so as to form an upper channel extending from the passageway towards the top edge of the second layer, and two walls disposed below the axial passageway so as to form a lower channel extending from the passageway towards the bottom edge of the second layer, wherein the upper channel provides fluid communication between the passageway and an upper portion of the patient's oral cavity, and the lower channel provides fluid communication between the passageway and a lower portion of the patient's oral cavity.

16. The device of claim 15, wherein each said channel extends at an angle with respect to the axial passageway.

17. The device of claim 12, wherein the tongue shield aspirator mates with the bite member in a non-rotational, non-pivotable manner.

18. The device of claim 12, wherein the top and bottom sides of the bite member lie in respective planes that diverge from each other.

19. The device of claim 12, further including a locking mechanism to detachably secure the evacuation tube to the bite member.

20. The device of claim 19, wherein the locking mechanism includes:
a radial flange proximate the first end of the evacuation tube and having one or more radial indentations; and
one or more internal radial protrusions adjacent said second end of the bite member's conduit,
wherein the first end of the evacuation tube is longitudinally moveable within the conduit only when the one or more radial indentations are aligned with the one or more internal radial protrusions.

* * * * *